United States Patent
Oung et al.

(10) Patent No.: US 11,720,656 B2
(45) Date of Patent: Aug. 8, 2023

(54) LIVE USER AUTHENTICATION DEVICE, SYSTEM AND METHOD

(71) Applicant: NYMI INC., Toronto (CA)

(72) Inventors: Stephen Oung, Toronto (CA); Avrum Douglas Hollinger, Toronto (CA); Gregor Simeonov, Toronto (CA); Abhishek Ranjan, Toronto (CA)

(73) Assignee: NYMI INC., Toronto (CA)

( * ) Notice: Subject to any disclaimer, the term of this patent is extended or adjusted under 35 U.S.C. 154(b) by 321 days.

(21) Appl. No.: 16/956,470

(22) PCT Filed: Jan. 18, 2019

(86) PCT No.: PCT/CA2019/050066
§ 371 (c)(1),
(2) Date: Jun. 19, 2020

(87) PCT Pub. No.: WO2019/140528
PCT Pub. Date: Jul. 25, 2019

(65) Prior Publication Data
US 2020/0342086 A1 Oct. 29, 2020

(30) Foreign Application Priority Data
Jan. 19, 2018 (CA) .................................... 2992333

(51) Int. Cl.
*G06F 21/32* (2013.01)
*A61B 5/00* (2006.01)
(Continued)

(52) U.S. Cl.
CPC ............ *G06F 21/32* (2013.01); *A61B 5/0006* (2013.01); *A61B 5/681* (2013.01); *G06F 1/163* (2013.01);
(Continued)

(58) Field of Classification Search
CPC ....... G06F 21/32; G06F 1/163; A61B 5/0006; A61B 5/681; G06V 40/1365;
(Continued)

(56) References Cited

U.S. PATENT DOCUMENTS

| 5,719,950 A | 2/1998 | Osten et al. |
| 6,175,641 B1 | 1/2001 | Kallo et al. |

(Continued)

FOREIGN PATENT DOCUMENTS

| CA | 2992333 A1 | 5/2018 |
| EP | 3037036 A1 | 6/2016 |

(Continued)

OTHER PUBLICATIONS

"A Framework for Patient State Tracking by Classifying Multiscalar Physiologic Waveform Features", dated Mar. 17, 2017, downloaded from https://www.ncbi.nlm.nih.gov/pmc/articles/PMC5736792/pdf/nihms923370.pdf and attached as PDF file. (Year: 2017).*

(Continued)

*Primary Examiner* — James D Nigh
(74) *Attorney, Agent, or Firm* — Knobbe, Martens, Olson & Bear, LLP

(57) ABSTRACT

Described are various embodiments of a digital user authentication device, the device comprising: a user authentication interface operable to receive as input unique user identification data required to execute a digital user authentication process; a distinct physiological sensor operable to interface with the user to acquire a physiological signal from the user to automatically confirm a live user presence during said authentication process; and a digital data processor and computer-readable memory operable to execute computer-readable instructions to invoke said user authentication process based on said unique user identification data while confirming said live user presence based on said physiologi- (Continued)

cal signal such that a successful user authentication is only concluded upon confirmation of said live user presence during said authentication process. Various authentication, access authorization and revocation systems and processes are also described.

21 Claims, 23 Drawing Sheets

(51) Int. Cl.
G06F 1/16 (2006.01)
G06V 40/12 (2022.01)
G06V 40/40 (2022.01)
G06V 40/10 (2022.01)
H04L 9/32 (2006.01)
H04L 9/40 (2022.01)
H04W 12/33 (2021.01)
H04L 9/08 (2006.01)
H04W 12/065 (2021.01)
G06V 40/50 (2022.01)

(52) U.S. Cl.
CPC ...... *G06V 40/1365* (2022.01); *G06V 40/1388* (2022.01); *G06V 40/45* (2022.01); *G06V 40/50* (2022.01); *H04L 9/0891* (2013.01); *H04W 12/065* (2021.01); *G06V 40/15* (2022.01); *H04L 2209/80* (2013.01)

(58) Field of Classification Search
CPC .... G06V 40/1388; G06V 40/45; G06V 40/50; G06V 40/15; H04L 9/0891; H04L 9/3231; H04L 2209/80; H04L 63/0861; H04W 12/065; H04W 12/33
USPC ......................................................... 713/186
See application file for complete search history.

(56) References Cited

U.S. PATENT DOCUMENTS

| | | | |
|---|---|---|---|
| 8,485,978 B2* | 7/2013 | Linder | A61B 5/6826 600/481 |
| 8,994,498 B2* | 3/2015 | Agrafioti | G06F 21/40 340/5.82 |
| 9,032,501 B1 | 5/2015 | Martin et al. | |
| 9,189,901 B2 | 11/2015 | Agrafioti et al. | |
| 9,197,414 B1 | 11/2015 | Martin et al. | |
| 9,349,235 B2 | 5/2016 | Agrafioti et al. | |
| 9,407,634 B2 | 8/2016 | Martin et al. | |
| 9,472,033 B2 | 10/2016 | Agrafioti et al. | |
| 9,646,261 B2 | 5/2017 | Agrafioti et al. | |
| 9,832,020 B2 | 11/2017 | Martin et al. | |
| 2006/0136744 A1 | 6/2006 | Lange | |
| 2010/0113952 A1 | 5/2010 | Raguin et al. | |
| 2011/0257546 A1* | 10/2011 | Gozzini | A61B 5/332 600/509 |
| 2013/0227651 A1 | 8/2013 | Schultz et al. | |
| 2014/0085050 A1* | 3/2014 | Luna | H04W 12/33 340/5.82 |
| 2014/0165185 A1 | 6/2014 | Lange | |
| 2014/0188770 A1* | 7/2014 | Agrafioti | A61B 5/7267 706/13 |
| 2015/0028996 A1 | 1/2015 | Agrafioti et al. | |
| 2015/0074797 A1 | 3/2015 | Choi et al. | |
| 2015/0135310 A1 | 5/2015 | Lee | |
| 2016/0042219 A1 | 2/2016 | Bae et al. | |
| 2016/0050217 A1* | 2/2016 | Mare | H04W 12/06 726/4 |
| 2016/0092665 A1* | 3/2016 | Cowan | H04W 12/06 726/9 |
| 2016/0183812 A1 | 6/2016 | Zhang et al. | |
| 2016/0283703 A1* | 9/2016 | Allyn | H04L 63/0861 |
| 2016/0352727 A1 | 12/2016 | Day et al. | |
| 2016/0381012 A1* | 12/2016 | Sydir | H04W 12/33 726/7 |
| 2017/0039358 A1* | 2/2017 | Yuen | A61B 5/11 |
| 2017/0286661 A1 | 10/2017 | Sezan et al. | |
| 2018/0020927 A1 | 1/2018 | Jain et al. | |

FOREIGN PATENT DOCUMENTS

KR 1015781670000 B1 12/2015
WO 2018137662 A1 8/2018

OTHER PUBLICATIONS

"A Framework for Patient State Tracking by Classifying Multiscalar Physiologic Waveform Features", dated Mar. 17, 2017, 26 pages (Year: 2017).*
Seneviratne et al."A Survey of Wearable Devices and Challenges", IEEE Communications Surveys & Tutorials, vol. 19, No. 4, Fourth Quarter 2017 (dated Nov. 17, 2017) pp. 2573-2620 (Year: 2017).*
Supplementary European Search Report issued for EP 19741180, dated Jan. 22, 2021.
Akhtar, Z. et al., "Biometric Liveness Detection: Challenges and Research Opportunities", IEEE Security and Privacy, vol. 13, No. 5, Sep./Oct. 2015, pp. 63-72, Oct. 28, 2015 (Oct. 28, 2015).
Cornelius, C. et al.,"A Wearable System that Knows Who Wears It", Proceedings of the International Conference on Mobile Systems, Applications, and Services (MobiSys), Jun. 16-19, 2014, Bretton Woods, New Hampshire, USD, pp. 55-67, Jun. 16, 2014 (Jun. 16, 2014).
Komeili, M. etat., "Liveness Section and Automatic Template Updating Using Fusion of ECG and Fingerprint", IEEE Transactions on Information Forensics and Security, vol. 13, No. 7, Jul. 2018, pp. 1810-1822, Jul. 1, 2018 (Jan. 7, 2018).
Ojala, S. et al., "Wearable Authentication Device for Transparent Login in Nomadic Applications Environment", Proceedings of 2008 2nd International Conference on Signals, Circuits and Systems, Nov. 7-9, 2008, Monastir, Tunisia, 6 pages, Nov. 7, 2008 (Jul. 11, 2008).
Drahansky, M., "Experiments with Skin Resistance and Temperature for Liveness Detection", Proceedings of the 2008 International Conference on Intelligent Information Hiding and Multimedia Signal Processing, Aug. 15-17, 2008, Harbin, China, pp. 1075-1079, Aug. 15, 2008 (Aug. 15, 2008).
Ojala, S. et al., "Wearable Authentication Device for Transparent Login in Nomadic Applications Environment", Proceedings of the 2008 Second International Conference on Signals, Circuits and Systems, Nov. 7-9, 2008, Monastir, Tunisia, 6 pages, Nov. 7, 2008 (Jul. 11, 2008).
Written Opinion of the International Searching Authority dated Apr. 30, 2019 for International Application No. PCT/CA2019/050066, 5 pages.
International Search Report dated Apr. 30, 2019 for International Application No. PCT/CA2019/050066, 5 pages.
Extended European Search Report received in EP Patent Application No. EP20802048.7 dated Dec. 21, 2022, 8 pages.

* cited by examiner

LIVE USER AUTHENTICATION DEVICE, SYSTEM AND METHOD

CROSS-REFERENCE TO RELATED APPLICATIONS

This application is a US National Phase of International Patent Application No. PCT/CA2019/050066, filed on Jan. 18, 2019, which claims priority to Canadian patent application No. 2,992,333 filed on Jan. 19, 2018, each of which is incorporated herein by reference in its entirety.

FIELD OF THE DISCLOSURE

The present disclosure relates to user access authentication and authorization systems, and, in particular, to a live user authentication device, system and method.

BACKGROUND

Digital identity authentication and access authorization is a key capability tied to many aspects of daily life, and is becoming even more vital with increasingly personalized technology offerings. Some methods for identity authentication can add varying levels of friction to our daily lives. In some cases, the cumulative friction of authentication mechanisms causes significant difficulty and inconvenience in a user's daily life. In the case of physical items, such as keys and cards, users may be carrying an ever-increasing load in their pockets and bags, having to dig out various items throughout the day. In the case of passwords and Personal Identification Numbers (PINs), user's online accounts and smart devices may require them, but remembering them while also making them sufficiently secure has become an elusive goal. Furthermore, these items, physical or digital, may be stolen or copied.

Modern biometric devices have promised a world of automatic and seamless identification; however, the practical realities result in trade-offs between security/accuracy and convenience. Existing biometric devices can be compromised. Vulnerabilities such as using a picture of a person to fool facial recognition or lifting and molding of fingerprints to fool a fingerprint scanner pose significant threats, necessitating additional layers of security, thereby diminishing the promise of biometrics.

On the other hand, references such as United States Patent Application Publication No. US 2014/0188770 A1 and U.S. Pat. No. 8,994,498 disclose biometric devices and systems in which biometric data can be captured and stored in the form of a user's electrocardiogram (ECG) so to perform subsequent user authentications on that basis. These techniques, while potentially robust in circumventing some of the challenges noted above, can present some drawbacks in the level of computational complexity and accuracy required to execute full ECG-based biometric authentication, and/or slow market acceptance or adoption of such novel authentication mechanisms.

This background information is provided to reveal information believed by the applicant to be of possible relevance. No admission is necessarily intended, nor should be construed, that any of the preceding information constitutes prior art or forms part of the general common knowledge in the relevant art.

SUMMARY

The following presents a simplified summary of the general inventive concept(s) described herein to provide a basic understanding of some aspects of the disclosure. This summary is not an extensive overview of the disclosure. It is not intended to restrict key or critical elements of embodiments of the disclosure or to delineate their scope beyond that which is explicitly or implicitly described by the following description and claims.

A need exists for a user authentication device, system and method that overcome some of the drawbacks of known techniques, or at least, provides a useful alternative thereto. Some aspects of this disclosure provide examples of such systems and methods, such as a live user authentication device, system and/or method.

In accordance with one aspect, there is provided a digital user authentication device to authenticate an authorized user, the device comprising: a wearable user authentication interface to be worn by the authorized user and operable to receive as input, via an authorized user finger contact, unique user identification data required to execute a digital user authentication process, wherein said wearable user authentication interface is operable to capture a user finger image via said authorized user finger contact as input for said unique user identification data; a distinct physiological sensor operable to interface with the authorized user via a same user finger contact and a distinct physiological interface formed at a distinct wearable user contact location, to simultaneously acquire, via said same user finger contact and said distinct physiological interface upon the device being worn by said authorized user, a physiological signal from the authorized user to automatically confirm a live user presence during said authentication process; a digital data processor and computer-readable memory operable to execute computer-readable instructions to invoke said user authentication process based on said unique user identification data while confirming said live user presence based on said physiological signal such that a successful user authentication is only concluded upon confirmation of said live user presence during said authentication process, wherein said digital data processor and computer-readable memory are further operable to invoke comparison of said physiological signal with a generic physiological signal profile to confirm said live user presence.

In accordance with another aspect, there is provided a digital user authentication system for authenticating an authorized user, the system comprising: a wearable wireless digital user authentication device comprising: a wearable user authentication interface to be worn by the authorized user and operable to receive as input, via an authorized user finger contact, unique user identification data required to execute a digital user authentication process, wherein said wearable user authentication interface is operable to capture a user finger image via said authorized user finger contact as input for said unique user identification data; a distinct physiological sensor operable to interface with the authorized user via a same user finger contact and a distinct physiological interface formed at a distinct wearable user contact location, to simultaneously acquire, via said same user finger contact and said distinct physiological interface upon the device being worn by said authorized user, a physiological signal from the authorized user to automatically confirm a live user presence during said authentication process; a digital data processor and computer-readable memory operable to execute computer-readable instructions to invoke said user authentication process based on said unique user identification data while confirming said live user presence based on said physiological signal such that a successful user authentication is only concluded upon confirmation of said live user presence during said authentication process, wherein said digital data processor and computer-readable memory are further operable to invoke comparison of said physiological signal with a generic physiological signal profile to confirm said live user presence; and a wireless communication interface operable to communicate authenticated user signal to a wireless access point once successfully authenticated; and a wireless access point operable to wirelessly receive said authenticated user signal from said wireless digital user authentication device to authenticate the authorized user based on said successful authentication.

In accordance with another aspect, there is provided a computer-implemented digital user authentication process, comprising: receiving via an authorized user finger contact as input at a wearable user authentication device, said device to be worn by an authorized user, unique user identification data to invoke a digital user authentication process, wherein said wearable user authentication interface is operable to capture a user finger image via said authorized user finger contact as input for said unique user identification data; receiving simultaneously as further input via a same user finger contact and a distinct physiological interface formed at a distinct wearable user contact location of said wearable user authentication device a physiological signal to automatically confirm a live user presence of said authorized user during said authentication process; and using one or more digital data processors, invoking said user authentication process based on said unique user identification data while confirming said live user presence based on said physiological signal such that a successful user authentication is only concluded upon confirmation of said live user presence during said authentication process, wherein said live user presence is confirmed upon successfully comparing said physiological signal with a generic physiological signal profile within a designated level of confidence.

In accordance with another aspect, there is provided a digital user authentication device to authenticate an authorized user, the device comprising: a wearable biometric sensor to be worn by the authorized user and operable to receive as input, via an authorized user finger contact, unique user identification data required to execute a digital user authentication process; a distinct physiological sensor operable to interface with the authorized user via a same user finger contact and a distinct physiological interface formed at a distinct wearable user contact location, to simultaneously acquire, via said same user finger contact and said distinct physiological interface upon the device being worn by the authorized user, a physiological signal from the authorized user to automatically confirm a live user presence during said authentication process; a digital data processor and computer-readable memory operable to execute computer-readable instructions to invoke said user authentication process based on said unique user identification data while confirming said live user presence based on said physiological signal such that a successful user authentication is only concluded upon confirmation of said live user presence during said authentication process, wherein said digital data processor and computer-readable memory are further operable to invoke comparison of said physiological signal with a generic physiological signal profile to confirm said live user presence.

In accordance with another aspect, there is provided a digital user authentication system for authenticating an authorized user, the system comprising: a wearable wireless digital user authentication device to be worn by the authorized user and comprising: a wearable biometric sensor operable to receive as input, via an authorized user finger contact, unique user identification data required to execute a digital user authentication process; a distinct physiological sensor operable to interface with the authorized user via a same user finger contact and a distinct physiological interface formed at a distinct wearable user contact location, to simultaneously acquire, via said same user finger contact and said distinct physiological interface upon the device being worn by said authorized user, a physiological signal from the authorized user to automatically confirm a live user presence during said authentication process; a digital data processor and computer-readable memory operable to execute computer-readable instructions to invoke said user authentication process based on said unique user identification data while confirming said live user presence based on said physiological signal such that a successful user authentication is only concluded upon confirmation of said live user presence during said authentication process, wherein said digital data processor and computer-readable memory are further operable to invoke comparison of said physiological signal with a generic physiological signal profile to confirm said live user presence; and a wireless communication interface operable to communicate authenticated user signal to a wireless access point once successfully authenticated; and a wireless access point operable to wirelessly receive said authenticated user signal from said wireless digital user authentication device to authenticate the authorized user based on said successful authentication.

In accordance with another aspect, there is provided a digital user authentication device, the device comprising: a user authentication interface operable to receive as input unique user identification data required to execute a digital user authentication process; a distinct physiological sensor operable to interface with the user to acquire a physiological signal from the user to automatically confirm a live user presence during said authentication process; a digital data processor and computer-readable memory operable to execute computer-readable instructions to invoke said user authentication process based on said unique user identification data while confirming said live user presence based on said physiological signal such that a successful user authentication is only concluded upon confirmation of said live user presence during said authentication process.

In accordance with another aspect, there is provided a digital user authentication system for accessing a designated resource, the system comprising: a wireless digital user authentication device comprising: a user authentication interface operable to receive as input unique user identification data required to execute a digital user authentication process; a distinct physiological sensor operable to interface with the user to acquire a physiological signal from the user to automatically confirm a live user presence during said authentication process; a digital data processor and computer-readable memory operable to execute computer-readable instructions to invoke said user authentication process based on said unique user identification data while confirming said live user presence based on said physiological signal such that a successful user authentication is only concluded upon confirmation of said live user presence during said authentication process; and a wireless communication interface operable to communicate with a wireless access point to wirelessly authorize the user authenticated access to a resource operatively associated with said wireless access point once successfully authenticated; and a wireless access point operatively associated with the designated resource and operable to wirelessly receive data from said wireless digital user authentication device to authorize user authenticated access to the designated resource based on said successful authentication.

In accordance with another aspect, there is provided a digital user authentication system for providing authorized authenticated user access to a designated resource, the system comprising: a wireless access point operatively associated with the designated resource and operable to wirelessly receive user resource access data from a wireless digital user authentication device to authorize user authenticated access to the designated resource; a wireless digital user authentication device comprising: a wireless communication interface operable to communicate said user resource access data to said wireless access point to gain the authorized authenticated user access to the designated resource; a physiological sensor operable to interface with the user to acquire a physiological signal from the user to automatically confirm a live user presence during the authorized access; a digital data processor and computer-readable memory operable to execute computer-readable instructions to: confirm said live user presence based on said physiological signal so to maintain the authorized access; and otherwise invoke revocation of the authorized access via said access point upon identifying a designated lapse in said physiological signal.

In accordance with another aspect, there is provided a wireless digital user authentication device operable to provide authorized user access, the device comprising: a wireless communication interface operable to communicate data in providing for the authorized user access; a physiological sensor operable to interface with the user to acquire a physiological signal from the user to automatically confirm a live user presence during the authorized user access; a digital data processor and computer-readable memory operable to execute computer-readable instructions to: confirm said live user presence based on said physiological signal so to maintain the authorized user access; and otherwise invoke revocation of the authorized access upon identifying a designated lapse in said physiological signal.

In accordance with another aspect, there is provided a computer-implemented digital user access authorization process, comprising: receiving as input at a wearable user authentication device unique user identification data to invoke a digital user authentication process; receiving as further input at said wearable user authentication device a physiological signal to automatically confirm a live user presence during said authentication process; and using one or more digital data processors, invoking said user authentication process based on said unique user identification data while confirming said live user presence based on said physiological signal such that a successful user authentication is only concluded upon confirmation of said live user presence during said authentication process.

Other aspects, features and/or advantages will become more apparent upon reading of the following non-restrictive description of specific embodiments thereof, given by way of example only with reference to the accompanying drawings.

BRIEF DESCRIPTION OF THE FIGURES

Several embodiments of the present disclosure will be provided, by way of examples only, with reference to the appended drawings, wherein:

FIGS. 19A to 19C are illustrative ECG signals acquired using a collocated finger and wrist probe pair of a wearable authentication device, in which a user compliance with a prescribed same user ECG contact configuration is incrementally reduced resulting in a decreasing signal quality, whereas

Figure 1:
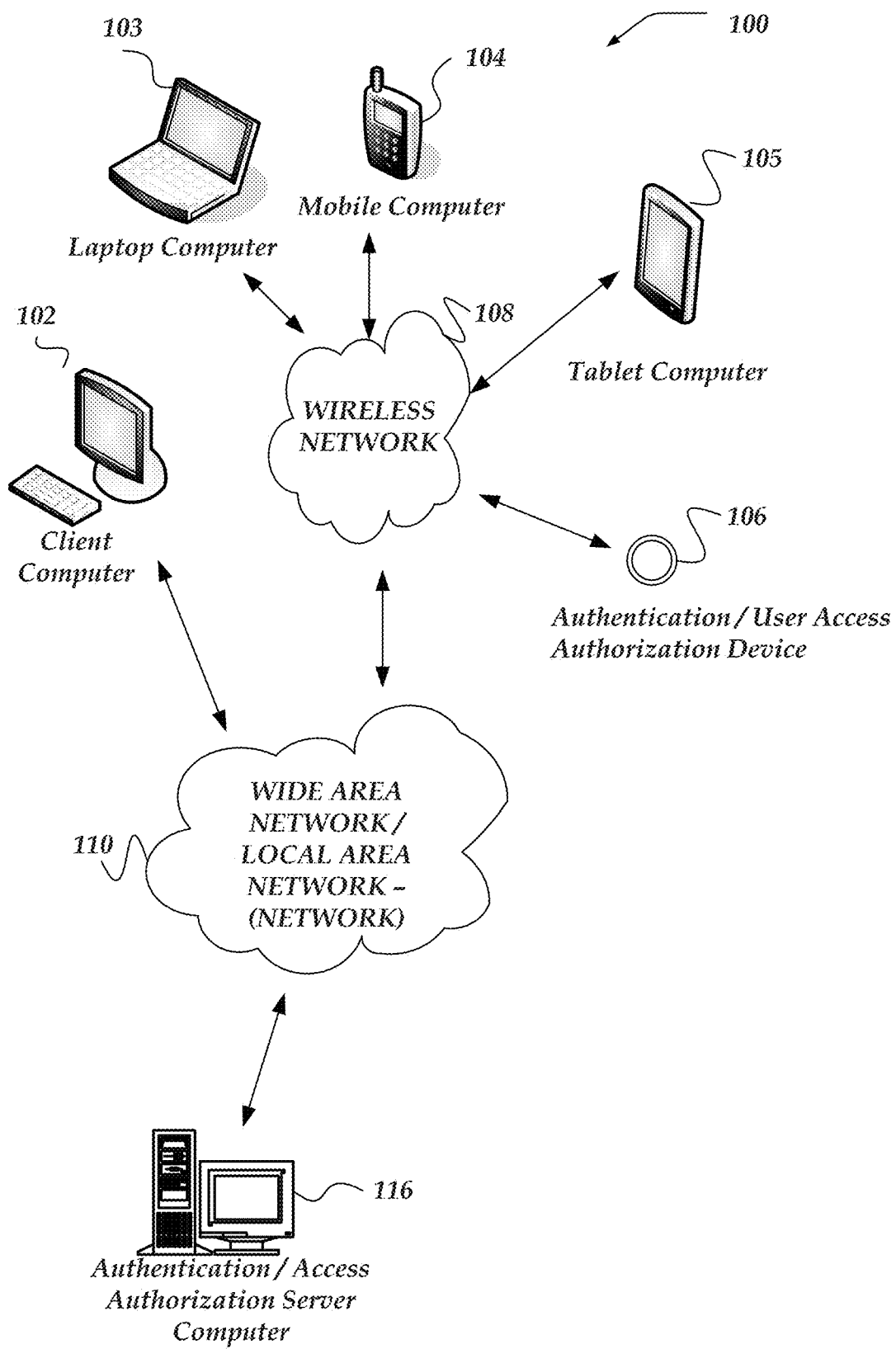
FIG. 1 is a component diagram for an environment in which embodiments of the disclosure may be practiced.

Elements in the several figures are illustrated for simplicity and clarity and have not necessarily been drawn to scale. For example, the dimensions of some of the elements in the figures may be emphasized relative to other elements for facilitating understanding of the various presently disclosed embodiments. Also, common, but well-understood elements that are useful or necessary in commercially feasible embodiments are often not depicted in order to facilitate a less obstructed view of these various embodiments of the present disclosure.

DETAILED DESCRIPTION

Various implementations and aspects of the specification will be described with reference to details discussed below. The following description and drawings are illustrative of the specification and are not to be construed as limiting the specification. Numerous specific details are described to provide a thorough understanding of various implementations of the present specification. However, in certain instances, well-known or conventional details are not described in order to provide a concise discussion of implementations of the present specification.

Various apparatuses and processes will be described below to provide examples of implementations of the system disclosed herein. No implementation described below limits any claimed implementation and any claimed implementations may cover processes or apparatuses that differ from those described below. The claimed implementations are not limited to apparatuses or processes having all of the features of any one apparatus or process described below or to features common to multiple or all of the apparatuses or processes described below. It is possible that an apparatus or process described below is not an implementation of any claimed subject matter.

Furthermore, numerous specific details are set forth in order to provide a thorough understanding of the implementations described herein. However, it will be understood by those skilled in the relevant arts that the implementations described herein may be practiced without these specific details. In other instances, well-known methods, procedures and components have not been described in detail so as not to obscure the implementations described herein.

In this specification, elements may be described as "configured to" perform one or more functions or "configured for" such functions. In general, an element that is configured to perform or configured for performing a function is enabled to perform the function, or is suitable for performing the function, or is adapted to perform the function, or is operable to perform the function, or is otherwise capable of performing the function.

It is understood that for the purpose of this specification, language of "at least one of X, Y, and Z" and "one or more of X, Y and Z" may be construed as X only, Y only, Z only, or any combination of two or more items X, Y, and Z (e.g., XYZ, XY, YZ, ZZ, and the like). Similar logic may be applied for two or more items in any occurrence of "at least one . . . " and "one or more . . . " language.

Unless defined otherwise, all technical and scientific terms used herein have the same meaning as commonly understood by one of ordinary skill in the art to which this invention belongs.

Throughout the specification and claims, the following terms take the meanings explicitly associated herein, unless the context clearly dictates otherwise. The phrase "in one of the embodiments" or "in at least one of the various embodiments" as used herein does not necessarily refer to the same embodiment, though it may. Furthermore, the phrase "in another embodiment" or "in some embodiments" as used herein does not necessarily refer to a different embodiment, although it may. Thus, as described below, various embodiments may be readily combined, without departing from the scope or spirit of the innovations disclosed herein.

In addition, as used herein, the term "or" is an inclusive "or" operator, and is equivalent to the term "and/or," unless the context clearly dictates otherwise. The term "based on" is not exclusive and allows for being based on additional factors not described, unless the context clearly dictates otherwise. In addition, throughout the specification, the meaning of "a," "an," and "the" include plural references. The meaning of "in" includes "in" and "on."

As used in the specification and claims, the singular forms "a", "an" and "the" include plural references unless the context clearly dictates otherwise.

The term "comprising" as used herein will be understood to mean that the list following is non-exhaustive and may or may not include any other additional suitable items, for example one or more further feature(s), component(s) and/or element(s) as appropriate.

The terms "physiological," "physiological data," or "physiological signal" as used herein are understood to mean any signal that can be obtained via a sensor or device when operatively interfacing with a user to confirm a live user presence. Non-limiting examples of physiological signals are heart rate, galvanic skin response, temperature, electrocardiogram (ECG), photoplethysmogram (PPG), electromyogram, electroencephalogram, transient otoacoustic emissions, phonocardiogram, perspiration, or a combination thereof. A live user presence can also be confirmed using any combination of the above or other physiological parameters, as can other physiological signals and/or sensors be considered alone or in combination to produce this result.

The terms "biometric," "biometric data," or "biometric signal" as used herein are understood to mean any signal that can be obtained from a user that can uniquely identify the user, including, but not limited to, one or more unique physiological signals or signatures that can be processed to uniquely identifier the user. Non-limiting examples of biometric signals are gait, heart rate, galvanic skin response, temperature, fingerprint, voice or voiceprint, body electrical characteristic, body thermal characteristic, iris pattern, vein pattern, eye vein pattern, facial or other anatomical structure, electrocardiogram (ECG), photoplethysmogram (PPG), electromyogram, electroencephalogram, transient otoacoustic emissions, phonocardiogram, DNA, one or more chemical markers, one or more biochemical markers, skin-color variation or discolouration, perspiration, or a combination thereof. A unique identity of a user can also be obtained by observing patterns or combinations of one or more biometric characteristic. For example a person may have a unique heart rate at a particular temperature and with a particular amount of sweat. In this way, two or more biometric observations can be combined or fused to obtain a multi-modal unique biometric profile. This is especially useful in situations wherein one particular biometric is not sufficient as a standalone identifier. In one example, perspiration and gait can be combined or fused to provide a unique biometric profile for a user. Information from sources that are stand-alone identifiers can also be combined in order to increase accuracy and/or security. In another example, a multi-modal biometric system may fuse fingerprints with iris and face characteristics.

The terms "access point" and "resource" are used interchangeably herein to refer to any logical or physical gateway, device, or application that requires authorization and/or authentication, such as for security or personalization purposes, and is otherwise locked or inaccessible to the user. Some non-limiting examples of physical access points are electronically locked doors, parking transceivers, smart environment technologies, vehicle doors and transit systems. Some non-limiting examples of logical access points are password, PIN, passcode or otherwise digitally protected electronic devices (e.g. smartphone, desktop computer, laptop, tablet, workstation, onboard vehicular device, etc.) or accounts, proof of payment systems, point of sale stations, automated bank teller machines, library checkout systems, and hotel and airport check-in stations. Further, access points may be considered a generic term for applications, computers, terminals, devices, or the like, that are enabled to communicate using the protocols described herein. For example, a wireless access point may be operatively associated with a network application to identify, monitor or track an authenticated user presence without necessarily invoking a further action in response to such recognized user presence. Namely, while some embodiments may encompass an access point for the purposes of authenticating a user presence in order to grant the user authenticated access to a particular resource, user presence authentication may not be limited to such applications, but may also include embodiments where a user's authenticated presence is recognized, monitored and/or tracked for other purposes, such as for advertising, analyzing user traffic an/or usage of designated physical spaces, law enforcement, etc. For simplicity, the terms "access point" and "resource" will be used interchangeably herein to refer not only to the computational device or application (e.g. physical hardware, firmware and/or software application) being accessed and operated to implement or provide for user presence authentication and/or access authorizations, but also any one or more resources that are operatively associated therewith, whereby a resources may include, but is not limited to: a physical space, room, zone or area contained or otherwise restricted by an electronically controlled gateway, door, gate or entryway; physical or computational workstation, device, equipment and/or tool for manufacturing, testing, verification, simulation, development, research, experimentation, development, assembly, etc.; physical or digital library, directory, repository and/or other classified or restricted information repository; and/or the like.

The term "access control signal" as used herein refers to a signal sent by an access control device, such as a user authentication device (UAD) to a physical or logical access point and/or resource that may enable the user to unlock, interface and/or access the access point/resource. The control signal may be a binary encoded sequence or user identifier transmitted wired or wirelessly using but not limited to Bluetooth (e.g. BLE), near field communication, ultra-wide band, RFID, or Wifi. The control signal may include, represent or correspond with a biometric, non-biometric, physiological and/or non-physiological signal depending on the application and/or context at hand.

The term "finger" as used herein refers to any digit attached to a hand or foot, including a thumb or a toe.

The term "encryption" as used herein is understood to refer to actions that change (information) from one form to another especially to hide its meaning. Further, in some embodiments, encryption as used herein may include employing pseudorandom transformations that produce pseudorandom outputs in the sense that a cipher text may be distinguishable from a completely random sequence of bits of the same length without revealing anything about the plaintext. For example, consider adding one or more zeros at the end of every encryption output. In at least one of the various embodiments, encryption may include applying pseudo-random function information, where the key of the pseudorandom function may be stored locally on a mobile device.

The terms "authorized authentication device" and "user authentication device" as used herein refer to devices and/or access points that may be arranged to include specialized applications for enrolling/registering a mobile device with a user. Authorized authentication devices (AADs) may be arranged to store keys, encrypted biometric user profiles, or the like. In some embodiments, implementation of at least some of the AAD functionality may be incorporated and/or otherwise embedded within the functions of a portable device, such as embedded within a wearable authentication/user access authorization device or the like, and/or distributed between such portable/wearable devices and/or one or more network-accessible servers, client computers, access points or the like. In some of the examples provided herein, a user authentication device or "UAD" is defined as a portable or wearable device operable to execute onboard user authentication procedures to thereby activate the UAD to broadcast or otherwise communicate or distribute an authenticated user status or identity for implementing/processing authenticated user presence or access privileges with one or more access points/resources.

The following briefly describes various embodiments in order to provide a basic understanding of some aspects of the herein described technology. This brief description is not intended as an extensive overview. It is not intended to identify key or critical elements, or to delineate or otherwise narrow the scope. Its purpose is merely to present some concepts in a simplified form as a prelude to the more detailed description that is presented later.

The systems and methods described herein provide, in accordance with different embodiments, different examples of a user access authorization system and method, and physiological user sensor and authentication device therefor.

For example, different embodiments as contemplated herein allow for digital user authentication and/or access authorization on the basis of both user authentication and confirmation of a live user presence, for example, as confirmed via an acquired physiological signal or like data that can be used to confirm that the authenticated user is in fact present during authentication and/or during active authorized user access. For example, in one embodiment, a digital authentication device may be configured to receive as input unique user authentication data, such as a personal identification number (PIN), username and/or password, passphrase, or like input, or again acquire or otherwise receive as input biometric data uniquely identifying the user (e.g. fingerprint, finger-vein or like finger image-based biometry, iris scan, voice recognition, facial recognition, unique physiological signature—ECG, heart rate, gait, perspiration, PPG vein recognition, body temperature, or the like), which data can be used to digitally authenticate the user. Such authentication may be required in different contexts, such as for gaining access to one or more digital and/or physical resources via an operatively associated access point, implementing authenticated user presence monitoring or tracking, or like considerations as introduced above and further detailed below.

In combination with user authentication, the authentication device may further include one or more same and/or distinct physiological sensors or like components operable to interface with the user (e.g. via a direct or indirect user contact, such as a skin contact or like interface operable in contact with or in close proximity to the user's skin or body) to acquire a physiological signal to automatically confirm a live user presence during authentication. Exemplary physiological signals may include, but are not limited to static and/or time-variable signals such as ECG, heart rate, perspiration, body temperature, or the like.

In such embodiments, the user may then, and only then, successfully complete the authentication process, or again, may only gain full authorized access to certain resources, attributes, features and/or functions, commonly referred to herein as resources for simplicity, upon successful live user presence authentication.

As further detailed below, the provision of multimodal access authentication and authorization may provide various features, functions and advantages in deterring unauthorized or otherwise illegitimate access to certain resources, for example. For instance, the illegitimate use of a user's authentication data, be it in the form of a stolen PIN or password, or lifted biometric data, could be thwarted in the absence of a legitimate physiological signal providing adequate live user presence confirmation. Namely, the authentication device would not only require adequate input of the authentication data, but also adequate use and configuration (e.g. within the context of a wearable authentication device) to acquire appropriate physiological signals. In some further examples, the operation of a biometric sensor in gaining authentication access may be intrinsically coupled with operation of physiological sensor. For example, a touch sensitive biometric sensor (e.g. fingerprint reader) could double as one of the contact points for implementation of a two-contact physiological sensor (e.g. ECG and/or like hear monitors, etc.), or again act as a concurrent optical probe for other types of physiological sensors. These and other such considerations will become more apparent to the skilled artisan upon reading the following non-limiting examples of illustrative embodiments.

In some same or further embodiments, a live user presence as confirmed by an onboard physiological sensor may be required to maintain authorized access to a given resource, for instance, whereby digitally authenticated and/or authorized access can be revoked upon failure to maintain live user presence confirmation. Such confirmation may be probed, accessed or otherwise monitored continuously, or again through routine scheduled, random or otherwise intermittent physiological signal processing. Accordingly, an authentication device, such as a wearable or like device, could see its associated authentication status revoked upon the device being removed, for example, from the authenticated user.

In yet some further or other such embodiments, access authorizations may also or alternatively be invoked/revoked as a function of a user proximity to an authorizing access point. For example, a live authenticated user may have its access authorization revoked upon distancing themselves from a given access point or associated resource. This may be particularly beneficial where an otherwise authorized access to a given resource could be maintained in the absence of the authorized user allowing for unauthorized users to gain illegitimate access to such a resource. Ultimately, access authorization could be regained upon the authorized user returning within a predefined range of the authorizing access point in question.

In one or more of the various embodiments, different secondary features may be employed to gain and/or maintain authenticated access authorizations, such that in response to sensing one or more access points, for example, an authorized authentication device may be employed to provide access to the one or more access points, and/or resources associated therewith, until the authenticated user is determined to be unverified based on the one or more secondary features. In one or more of the various embodiments, providing access to the one or more access points or associated resources, may be delayed until one or more required physical gestures or actions may be performed by the user to confirm access by the user to the one or more access points, for example.

In one or more of the various embodiments, the authentication device may include a band that is adapted for encircling one or more of a wrist, finger, toe, foot, arm, waste, chest, head or neck of the user, for example, though other wearable configurations, such as but not limited to a patch, skin probe, or other wearable device, should be considered to fall within the general scope and nature of the present disclosure, as will be readily appreciated by the skilled artisan.

Illustrative Operating Environment

FIG. 1 shows components, in accordance with one illustrative embodiment, of an environment in which embodiments of the invention may be practiced. Not all of the components may be required to practice different embodiments of the invention, and variations in the arrangement and type of the components may be made without departing from the general spirit or scope of the present disclosure. As shown, system 100 of FIG. 1 includes local area networks (LANs)/wide area networks (WANs)-(network) 110, wireless network 108, client computers 102-105, authentication/access authorization device 106 (generally referred to herein as user authentication device (UAD) 106, which may include, but is not limited to, a mobile, wireless, portable wearable device and/or the like, for example), authentication/access authorization server computer 116 (generally referred to herein as authentication server 116), or the like.

At least one embodiment of client computers 102-105 is described in more detail below in conjunction with FIG. 2. In one embodiment, at least some of client computers 102-105 may operate over one or more wired and/or wireless networks, such as networks 108, and/or 110. Generally, client computers 102-105 may include virtually any computer capable of communicating over a network to send and receive information, perform various online activities, offline actions, or the like. In one embodiment, one or more of client computers 102-105 may be configured to operate within a business or other entity to perform a variety of services for the business or other entity. For example, client computers 102-105 may be configured to operate as a server, client application, media player, mobile telephone, game console, desktop computer, access point, or the like. However, client computers 102-105 are not constrained to these services and may also be employed, for example, as for end-user computing in other embodiments. It should be recognized that more or less client computers (as shown in FIG. 1) may be included within a system such as described herein, and embodiments are therefore not constrained by the number or type of client computers employed.

Computers that may operate as client computer 102 may include computers that typically connect using a wired or wireless communications medium such as personal computers, multiprocessor systems, microprocessor-based or programmable electronic devices, network PCs, or the like. In some embodiments, client computers 102-105 may include virtually any portable computer capable of connecting to another computer and receiving information such as, laptop computer 103, mobile computer 104, tablet computers 105, or the like. However, portable computers are not so limited and may also include other portable computers such as cellular telephones, display pagers, radio frequency (RF) devices, infrared (IR) devices, Personal Digital Assistants (PDAs), handheld computers, wearable computers, integrated devices combining one or more of the preceding computers, or the like. As such, client computers 102-105 typically range widely in terms of capabilities and features. Moreover, client computers 102-105 may access various computing applications, including a browser, or other web-based application.

A web-enabled client computer may include a browser application that is configured to receive and to send web pages, web-based messages, and the like. The browser application may be configured to receive and display graphics, text, multimedia, and the like, employing virtually any web-based language, including a wireless application protocol messages (WAP), and the like. In one embodiment, the browser application is enabled to employ Handheld Device Markup Language (HDML), Wireless Markup Language (WML), WMLScript, JavaScript, Standard Generalized Markup Language (SGML), HyperText Markup Language (HTML), eXtensible Markup Language (XML), JavaScript Object Notation (JSON), or the like, to display and send a message. In one embodiment, a user of the client computer may employ the browser application to perform various activities over a network (online). However, another application may also be used to perform various online activities.

One embodiment of Client computers 102-105 are described in more detail below in conjunction with FIG. 2. Briefly, however, Client computers 102-105 also may include at least one other client application that is configured to receive and/or send content between another computer. The client application may include a capability to send and/or receive content, or the like. The client application may further provide information that identifies itself, including a type, capability, name, and the like. In one embodiment, client computers 102-105 may uniquely identify themselves through any of a variety of mechanisms, including an Internet Protocol (IP) address, a phone number, Mobile Identification Number (MIN), an electronic serial number (ESN), or other device identifier. Such information may be provided in a network packet, or the like, sent between other client computers, server computer 116, device 106, or other computers.

Client computers 102-105 may further be configured to include a client application that enables an end-user to log into an end-user account that may be managed by another computer, such as server computer 116, or the like. Such an end-user account, in one non-limiting example, may be configured to enable the end-user to manage one or more online activities, including in one non-limiting example, project management, system administration, configuration management, search activities, social networking activities, browse various websites, communicate with other users, or the like.

One embodiment of device 106 is described in more detail below in conjunction with FIG. 4. Briefly, however, device 106 can be any device that can be worn or otherwise carried by a user and is capable of obtaining authentication data to invoke an authentication process, in this illustrated example, via server 116. As introduced above and as will be detailed below in accordance with some embodiments, authentication data may include manually entered data and/or biometric data acquired or otherwise input by the user to seek authentication and, in some implementations, certain access authorizations.

As noted above, some embodiments of device 106 will further include one or more physiological sensors and/or proximity detection mechanisms to provide secondary authentication and/or authorization measures to gain and/or maintain authentication/authorization in use.

Non-limiting examples of suitable wearable authentication devices may include, but are not limited to, a wristband, wristwatch, bracelet, necklace, ring, belt, glasses, clothing, hat, anklet, headband, chest harness, patch, skin probe or earring(s), to name a few, or any other wearable item that is capable of obtaining a biometric signal. The device 106 can also be incorporated into clothing. In another embodiment, the device 106 may comprise more than one biometric and/or physiological sensors, to be used alone and/or in combination, to carry out user authentication and/or live user presence confirmation. Device 106 may be arranged to communicate with one or more of client computer 102-105 over a network, such as wireless network 108. Further, device 106 may be arranged to communicate with access points, enabling user access to secure locations and secured electronic devices as well as customization of a user experience.

As will be appreciated by the skilled artisan, some of the features and/or functions noted above with respect to client computers 102-105 may be interchangeably applied to the functions and features of the herein described embodiments of portable device 106. For instance, while client computers are distinctly illustrated herein in one particular embodiment, some embodiments may further or alternatively contemplate portable and/or wearable client computers, as can other embodiments be considered to implement the features and functions of there herein described embodiments.

Wireless network 108 is configured to couple client computers 102-105 and/or and authentication device 106 with network 110. Wireless network 108 may include any of a variety of wireless sub-networks that may further overlay stand-alone ad-hoc networks, and the like, to provide an infrastructure-oriented connection for client computers 102-105 and/or authentication device 106. Such sub-networks may include mesh networks, Bluetooth, Wireless LAN (WLAN) networks, cellular networks, and the like. In one embodiment, the system may include more than one wireless network.

Wireless network 108 may further include an autonomous system of terminals, gateways, routers, and the like connected by wireless radio links, and the like. These connectors may be configured to move freely and randomly and organize themselves arbitrarily, such that the topology of wireless network 108 may change rapidly.

Wireless network 108 may further employ a plurality of access technologies including 2nd (2G), 3rd (3G), 4th (4G) 5th (5G) generation radio access for cellular systems, WLAN, Bluetooth, Wireless Router (WR) mesh, and the like. Access technologies such as 2G, 3G, 4G, 5G, and future access networks may enable wide area coverage for mobile computers, such as client computers 102-105, and authentication device 106 with various degrees of mobility. In one non-limiting example, wireless network 108 may enable a radio connection through a radio network access such as Global System for Mobil communication (GSM), General Packet Radio Services (GPRS), Enhanced Data GSM Environment (EDGE), code division multiple access (CDMA), time division multiple access (TDMA), Wideband Code Division Multiple Access (WCDMA), High Speed Downlink Packet Access (HSDPA), Long Term Evolution (LTE), and the like. In essence, wireless network 108 may include virtually any wireless communication mechanism by which information may travel between client computers 102-105, authentication device 106, and another computer, network, a cloud-based network, a cloud instance, or the like.

Network 110 is configured to couple network computers with other computers, including, authentication server computer 116, client computers 102-105, authentication device 106 through wireless network 108, or the like. Network 110 is enabled to employ any form of computer readable media for communicating information from one electronic device to another. Also, network 110 can include the Internet in addition to local area networks (LANs), wide area networks (WANs), direct connections, such as through a universal serial bus (USB) port, other forms of computer-readable media, or any combination thereof. On an interconnected set of LANs, including those based on differing architectures and protocols, a router acts as a link between LANs, enabling messages to be sent from one to another. In addition, communication links within LANs typically include twisted wire pair or coaxial cable, while communication links between networks may utilize analog telephone lines, full or fractional dedicated digital lines including T1, T2, T3, and T4, and/or other carrier mechanisms including, for example, E-carriers, Integrated Services Digital Networks (ISDNs), Digital Subscriber Lines (DSLs), wireless links including satellite links, or other communications links known to those skilled in the art. Moreover, communication links may further employ any of a variety of digital signaling technologies, including without limit, for example, DS-0, DS-1, DS-2, DS-3, DS-4, OC-3, OC-12, OC-48, or the like. Furthermore, remote computers and other related electronic devices could be remotely connected to either LANs or WANs via a modem and temporary telephone link. In one embodiment, network 110 may be configured to transport information of an Internet Protocol (P).

Additionally, communication media typically embodies computer readable instructions, data structures, program modules, or other transport mechanism and includes any information delivery media. By way of example, communication media includes wired media such as twisted pair, coaxial cable, fiber optics, wave guides, and other wired media and wireless media such as acoustic, RF, infrared, and other wireless media.

One embodiment of authentication server computer 116 is described in more detail below in conjunction with FIG. 3. Briefly, however, authentication server computer 116 includes virtually any network computer capable of performing actions for storing, authenticating, processing of biometric information, users, access points, or the like.

Although FIG. 1 illustrates authentication server computer 116 as a single computer, the innovations and/or embodiments are not so limited. For example, one or more functions of authentication server computer 116 may be distributed across one or more distinct network computers. Moreover, authentication server computer 116 is not limited to a particular configuration such as the one shown in FIG. 1. Thus, in one embodiment, authentication server computer 116 may be implemented using a plurality of network computers and/or client computer. In other embodiments, development computer may operate as a plurality of network computers within a cluster architecture, a peer-to-peer architecture, cloud or virtualized architecture, or the like. Further, in at least one of the various embodiments, authentication server computer 116 may be implemented using one or more cloud instances in one or more cloud networks.

Described herein, in accordance with some embodiments, is a system, method and device that authenticates a user while confirming that the user being authenticated is a genuine living human being. This system may also, or alternatively, seek to confirm a live user presence during authenticated/authorized usage, confirm proximity of such user to a given access point or associated resource during use (i.e. within a designated authorization zone, area or distance threshold), and/or evaluate other secondary user authorization parameters. In the herein illustrated embodiment, the system is centred around a wearable authentication device that authenticates the wearer based on available authentication data, which may include biometric data, while confirming, based on an acquired physiological signal, that the wearer is in fact a living human being. Some embodiments further allow for confirmation that the same user (i.e. the wearer) is both the source of the physiological signal and the authentication data, for instance, within the context of biometric authentication. In yet other embodiments, such live user presence, proximity and/or other related provisions may not be implemented, for instance, in reduced security environments and/or to reduce or limit complexity of the implemented authentication devices/systems.

In one embodiment, once authenticated, the wearable authentication device synchronizes with a pre-initialized authorized registration application to authorize the wearable authentication device to wirelessly communicate a pre-authenticated user identity to other devices and systems. In another embodiment, once authenticated, the wearable authentication device activates and privately broadcasts the user's identification to other devices and systems.

In yet other embodiments, authentication and/or physiological data is communicated or otherwise transferred to a trusted computation device, such as authentication server 116, for remote processing, thereby reducing a computational load on the wearable device. This enables logical and physical access by the user at one or more access points as a result of a single user authorization.

In contrast, traditional access systems, including biometric access systems, may be subject to hacking and/or misuse. For example, hackers may lift a fingerprint and create a fingerprint mold, which can be applied to a fingerprint sensor, in order to gain access. Hackers may also take a picture of a fingerprint, and hold it in front of a scanner. Similarly, a user of an authentication device that authenticates once, and then pre-authorizes access for a defined period of time, may be worn by a person without authorization while a person with authorization authenticates the device. Other drawbacks naturally exist, such as maintaining authorized access activations when a user removes the authentication device and/or leaves or moves away from the restricted access area or resource. Such possibilities may be unacceptable to security conscious institutions, resulting in additional layers of security being added, e.g. re-occurring user authentication, or using out of band mechanisms.

The herein-described embodiments provide a compelling security solution to at least some of these typical drawbacks by significantly reducing if not eliminating concerns about hacking and misuse of an authentication/authorization device. For example, in one illustrative embodiment where a biometric authentication sensor, such as a fingerprint reader, shares a contact point with a complementary physiological sensor, such as an ECG, even if a hacker were to lift a fingerprint, create a fingerprint mold, and attach or otherwise embed the fingerprint mold onto a glove while touching biometric authentication sensor, an analysis of the physiological sensor would determine that the user is not a live, in-the-flesh, human being, and so the authentication device would not authenticate the user. Furthermore, following from the same illustrative example, misuse of the authentication device, e.g. authenticating a device worn by another individual, is also prevented, as the physiological sensor could be configured to fail to take a reading unless the device was both worn and authenticated by the same user (e.g. an electrocardiogram or galvanic skin response does not exist across two people). Accordingly the authentication device would not authenticate, even if the biometric feature (e.g. a fingerprint) is a match. In addition, at least some of the presently described embodiments allow for faster access control since the user does not require authentication every time she needs to access a physical or logical system. As noted above, other features, advantages and benefits of the herein described embodiments, such as live user confirmation during and/or post-authentication, user proximity metrics, and/or other such features and advantages, will be readily apparent to the skilled artisan from the present disclosure.

Figure 18:
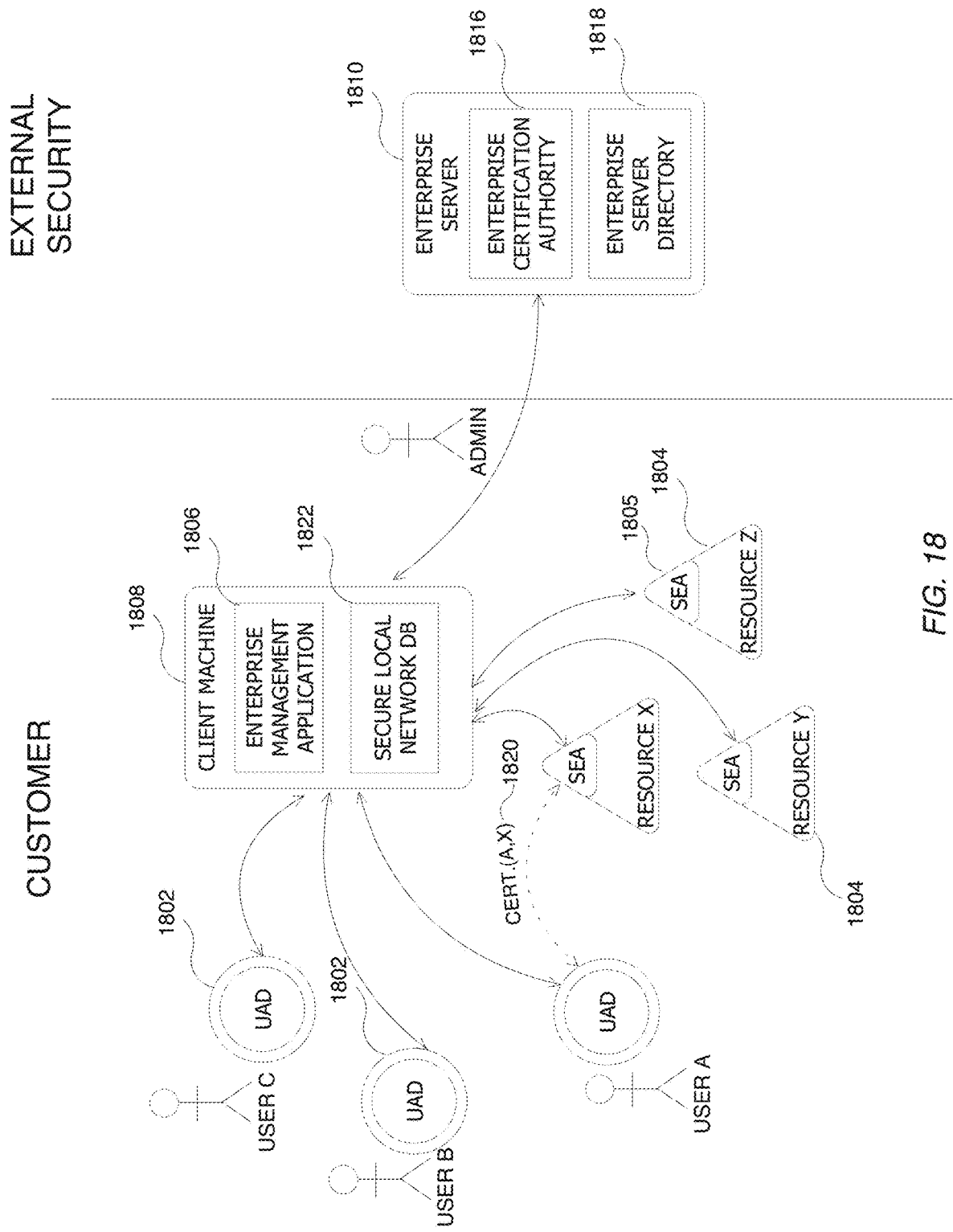
FIG. 18 is a high level system diagram illustrating various user authentication devices (UAD) operable to authenticate a user presence and/or gain access to distinct network-application enabled resources, in accordance with one embodiment.

With reference to FIG. 18, and in accordance with one embodiment, an illustrative high-level system architecture for managing authenticated user identities, authenticating user presence and/or access authorizations, will now be described. In this example, a set of end users are provided with a corresponding set of portable (wearable) user authentication devices (UAD) 1802 to be used to authenticate each end user (e.g. via PIN, password, onboard biometric authentication, etc.) for the purposes of communicating an authenticated user identity, for example, in authenticating a user presence and, in some further examples, gaining user access to one or more customer resources 1804 accordingly. Various measures to ensure secure user authentication, live user presence, prevent fraud, collusion or the like are illustratively introduced above and further described below, as are other complementary/alternative means for securely authenticating the user via onboard and/or communicatively accessible authentication and status broadcast resources.

Following onboard authentication in this example, once a UAD is active, it may be used to securely authenticate the user, for example, to gain authenticated access to certain authorized resources 1804 whose access is at least in part operatively controlled by a security-enabled (network) application 1805 operating locally or distributively to communicate with nearby UADs 1802 via a related access point or like communication path. For example, a given UAD 1802 may be logically linked to a particular user to perform onboard user authentication to activate the UAD 1802 and thus actively or selectively communicate or broadcast a user-authenticated status or authenticated user identity. For example, an actively authenticated or pre-authorized UAD may transact with one or more instances of a security enabled (network) application 1805 that can be operated to recognize, monitor and/or track an authenticated user presence, for example, to grant authenticated user access to one or more corresponding resources 1804 operatively associated therewith. For example, the network application 1805 may be operated to securely identify the authenticated user (e.g. using one or more (mutual) user/device/application authentication procedures) in providing authenticated access to the corresponding resource if so authorized. For simplicity, the following examples will relate to a system for granting authenticated user access privileges to authenticated users based on successful user identification, authentication and communications relating thereto between a given UAD and network application (instance).

Accordingly, each end user (User A, B, and C) may be attributed one or more customer access privileges or authorizations (e.g. to Resource X, Y and/or Z) to be implemented via their respective UAD 1802. To do so, respective digital certificates may be issued to accommodate such diversified access privileges; namely User A may seek to enrol a user-specific certificate to access Resource X (e.g. certificate (A,X) 1820)), User B may seek to enrol respective user-specific certificates to respectively access each of Resources Y and Z (but not X), and User C may seek to enrol respective user-specific certificates for each resource along with possibly a higher level authorization certificate to access the enterprise management application (EMA) 1806. Each certificate can then be used to successfully negotiate access to its corresponding resource via the resources' respective security-enabled application (SEA) instances 1805 (or EMA 1806).

In the illustrated embodiment, an external enterprise security services system is implemented for the purposes of providing customer security services in which multiple user authentication devices can be used to routinely authenticate authorized end users and manage user access privileges accordingly. For example, and with reference to the illustrative embodiment of FIG. 18, end user certificate enrolment, processing and related provisions are implemented via an external (standalone) CA 1816, enterprise directory 1818 and related sources, for example, to reduce customer impact and touch points in outsourcing management of such security resources (which external resources can be used to concurrently provide security management services to various customers interfacing therewith). In this embodiment, an enterprise management application 1806 operates on a customer/client machine (e.g. local network infrastructure) 1808 that interfaces with an enterprise server 1810 operated by the external security services provider to process certificate enrolment requests, optionally among other UAD enterprise setup procedures, and related security provisions and procedures. The enterprise management application 1806 may not only interface with the various UADs for the purposes of enterprise setup, processing and maintenance, but also optionally to provide administrative functions in linking respective instances of the security-enabled applications 1805, for example, for software/firmware update, synchronization and/or resource sharing, e.g. via secure local network database 1822 or the like. Access to a local or server-based enterprise directory or database may also be facilitated through a centralized management hub or application, as can other system architectures and/or configurations be considered.

Illustrative Client Computer

Figure 2:
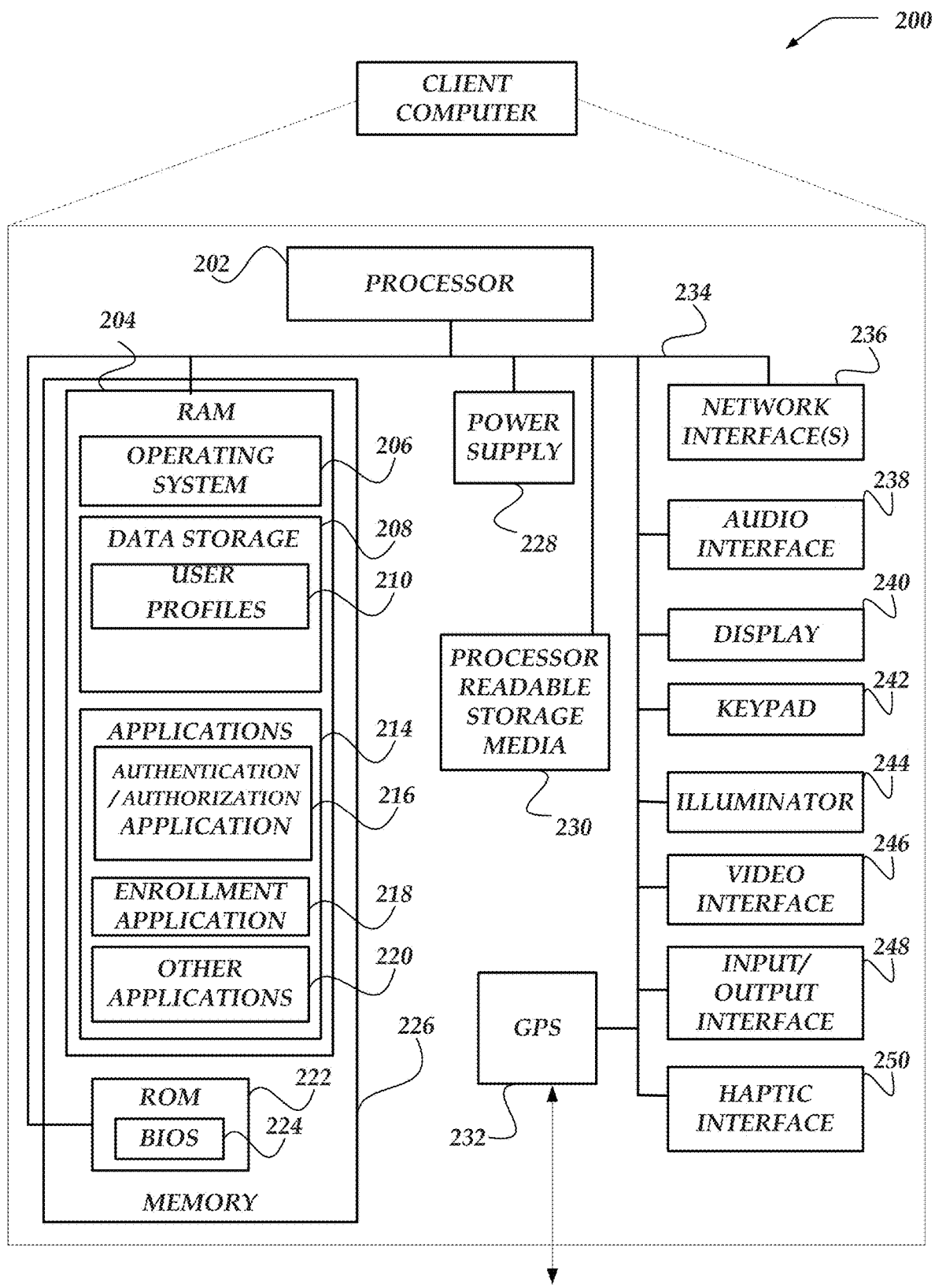
FIG. 2 is a diagram of an exemplary client computer that may be included in a system in accordance with at least one of the various embodiments.

FIG. 2 shows one embodiment of client computer 200 that may be included in a system in accordance with at least one of the various embodiments. Client computer 200 may include many more or less components than those shown in FIG. 2. However, the components shown are sufficient to disclose an illustrative embodiment for practicing different embodiments of the present invention. Client computer 200 may represent, for example, one embodiment of at least one of client computers 102-105 of FIG. 1.

As shown in the figure, client computer 200 includes a processor 202 in communication with a mass memory 226 via a bus 234. In some embodiments, processor 202 may include one or more central processing units (CPU). Client computer 200 also includes a power supply 228, one or more network interfaces 236, an audio interface 238, a display 240, a keypad 242, an illuminator 244, a video interface 246, an input/output interface 248, a haptic interface 250, and a global positioning system (GPS) receiver 232.

Power supply 228 provides power to client computer 200. A rechargeable or non-rechargeable battery may be used to provide power. The power may also be provided by an external power source, such as an alternating current (AC) adapter or a powered docking cradle that supplements and/or recharges a battery, or directly powering the unit.

Client computer 200 may optionally communicate with a base station (not shown), or directly with another computer. Network interface 236 includes circuitry for coupling client computer 200 to one or more networks, and is constructed for use with one or more communication protocols and technologies including, but not limited to, GSM, CDMA, TDMA, GPRS, EDGE, WCDMA, HSDPA, LTE, user datagram protocol (UDP), transmission control protocol/Internet protocol (TCP/IP), short message service (SMS), WAP, ultra-wide band (UWB), IEEE 802.16 Worldwide Interoperability for Microwave Access (WiMax), session initiated protocol/real-time transport protocol (SIP/RTP), or any of a variety of other wireless communication protocols. Network interface 236 is sometimes known as a transceiver, transceiving device, or network interface card (NIC).

Audio interface 238 is arranged to produce and receive audio signals such as the sound of a human voice. For example, audio interface 238 may be coupled to a speaker and microphone (not shown) to enable telecommunication with others and/or generate an audio acknowledgement for some action.

Display 240 may be a liquid crystal display (LCD), gas plasma, light emitting diode (LED), organic LED, AMOLED, PMOLED, or any other type of display used with a computer. Display 240 may also include a touch sensitive screen arranged to receive input from an object such as a stylus or a digit from a human hand.

Keypad 242 may comprise any input device arranged to receive input from a user. For example, keypad 242 may include a push button numeric dial, or a keyboard. Keypad 242 may also include command buttons that are associated with selecting and sending images.

Illuminator 244 may provide a status indication and/or provide light. Illuminator 244 may remain active for specific periods of time or in response to events. For example, when illuminator 244 is active, it may backlight the buttons on keypad 242 and stay on while the client computer is powered. Also, illuminator 244 may backlight these buttons in various patterns when particular actions are performed, such as dialing another client computer. Illuminator 244 may also cause light sources positioned within a transparent or translucent case of the client computer to illuminate in response to actions.

Video interface 246 is arranged to capture video images, such as a still photo, a video segment, an infrared video, or the like. For example, video interface 246 may be coupled to a digital video camera, a web-camera, or the like. Video interface 246 may comprise a lens, an image sensor, and other electronics. Image sensors may include a complementary metal-oxide-semiconductor (CMOS) integrated circuit, charge-coupled device (CCD), or any other integrated circuit for sensing light.

Client computer 200 also comprises input/output interface 248 for communicating with external devices, such as a headset, or other input or output devices not shown in FIG. 2. Input/output interface 248 can utilize one or more communication technologies, such as USB, infrared, Bluetooth™, ultrasound, WiFi, ultra-wideband, or the like.

Haptic interface 250 is arranged to provide tactile feedback to a user of the client computer. For example, the haptic interface 250 may be employed to vibrate client computer 200 in a particular way when another user of a computer is calling. In some embodiments, haptic interface 250 may be optional.

Client computer 200 may also include GPS transceiver 232 to determine the physical coordinates of client computer 200 on the surface of the Earth. GPS transceiver 232, in some embodiments, may be optional. GPS transceiver 232 typically outputs a location as latitude and longitude values. However, GPS transceiver 232 can also employ other geo-positioning mechanisms, including, but not limited to, triangulation, assisted GPS (AGPS), Enhanced Observed Time Difference (E-OTD), Cell Identifier (CI), Service Area Identifier (SAI), Enhanced Timing Advance (ETA), Base Station Subsystem (BSS), or the like, to further determine the physical location of client computer 200 on the surface of the Earth. It is understood that under different conditions, GPS transceiver 232 can determine a physical location within millimeters for client computer 200; and in other cases, the determined physical location may be less precise, such as within a meter or significantly greater distances. In one embodiment, however, client computer 200 may through other components, provide other information that may be employed to determine a physical location of the computer, including for example, a Media Access Control (MAC) address, IP address, or the like.

Mass memory 226 includes a Random Access Memory (RAM) 204, a Read-only Memory (ROM) 222, and other storage means. Mass memory 226 illustrates an example of computer readable storage media (devices) for storage of information such as computer readable instructions, data structures, program modules or other data. Mass memory 226 stores a basic input/output system (BIOS) 224, or the like, for controlling low-level operation of client computer 200. The mass memory also stores an operating system 206 for controlling the operation of client computer 200. It will be appreciated that this component may include a general-purpose operating system such as a version of UNIX, or LINUX™, or a speialized client communication operating system such as Microsoft Corporation's Windows Mobile™ Apple Corporation's iOS™, Google Corporation's Android™, or the like. The operating system may include, or interface with a Java virtual machine module that enables control of hardware components and/or operating system operations via Java application programs.

Mass memory 226 further includes one or more data storage 208, which can be utilized by client computer 200 to store, among other things, applications 214 and/or other data. For example, data storage 208 may also be employed to store information that describes various capabilities of client computer 200. The information may then be provided to another computer based on any of a variety of events, including being sent as part of a header during a communication, sent upon request, or the like. Data storage 208 may also be employed to store social networking information including address books, buddy lists, aliases, user profile information, user credentials, or the like. Further, data storage 208 may also store messages, web page content, or any of a variety of user generated content.

At least a portion of the information stored in data storage 208 may also be stored on another component of client computer 200, including, but not limited to processor readable storage media 230, a disk drive or other computer readable storage devices (not shown) within client computer 200. Further, at least a portion of data storage 208 may be used to store user (e.g. authentication, authorization and/or biometric) profile information 210 for one or more users and/or one or more authentication devices.

Processor readable storage media 230 may include volatile, non-transitive, non-transitory, non-volatile, removable, and non-removable media implemented in any method or technology for storage of information, such as computer- or processor-readable instructions, data structures, program modules, or other data. Examples of computer readable storage media include RAM, ROM, Electrically Erasable Programmable Read-only Memory (EEPROM), flash memory or other memory technology, Compact Disc Read-only Memory (CD-ROM), digital versatile disks (DVD) or other optical storage, magnetic cassettes, magnetic tape, magnetic disk storage or other magnetic storage devices, or any other physical medium which can be used to store the desired information and which can be accessed by a computer. Processor readable storage media 230 may also be referred to herein as computer readable storage media and/or computer readable storage device.

Applications 214 may include computer executable instructions which, when executed by client computer 200, transmit, receive, and/or otherwise process network data. Network data may include, but is not limited to, messages (e.g. SMS, Multimedia Message Service (MMS), instant message (IM), email, and/or other messages), audio, video, and enable telecommunication with another user of another client computer. Applications 214 may include, for example, user (e.g. biometric) authentication application 216, enrollment application 218, other applications 220, or the like.

Other applications 220 may include a web browser. The web browser may include virtually any application configured to receive and display graphics, text, multimedia, messages, and the like, employing virtually any web based language. In one embodiment, the browser application is enabled to employ HDML, WML, WMLScript, JavaScript, SGML, HTML, XML, and the like, to display and send a message. However, any of a variety of other web-based programming languages may be employed. In one embodiment, the browser may enable a user of client computer 200 to communicate with another network computer, such as authentication server computer 116 as shown in FIG. 1.

Other applications 220 may additionally include, but are not limited to, calendars, search programs, email clients, IM applications, SMS applications, voice over Internet Protocol (VOIP) applications, contact managers, task managers, transcoders, database programs, word processing programs, software development tools, security applications, spreadsheet programs, games, search programs, and so forth.

Illustrative Network Computer

Figure 3:
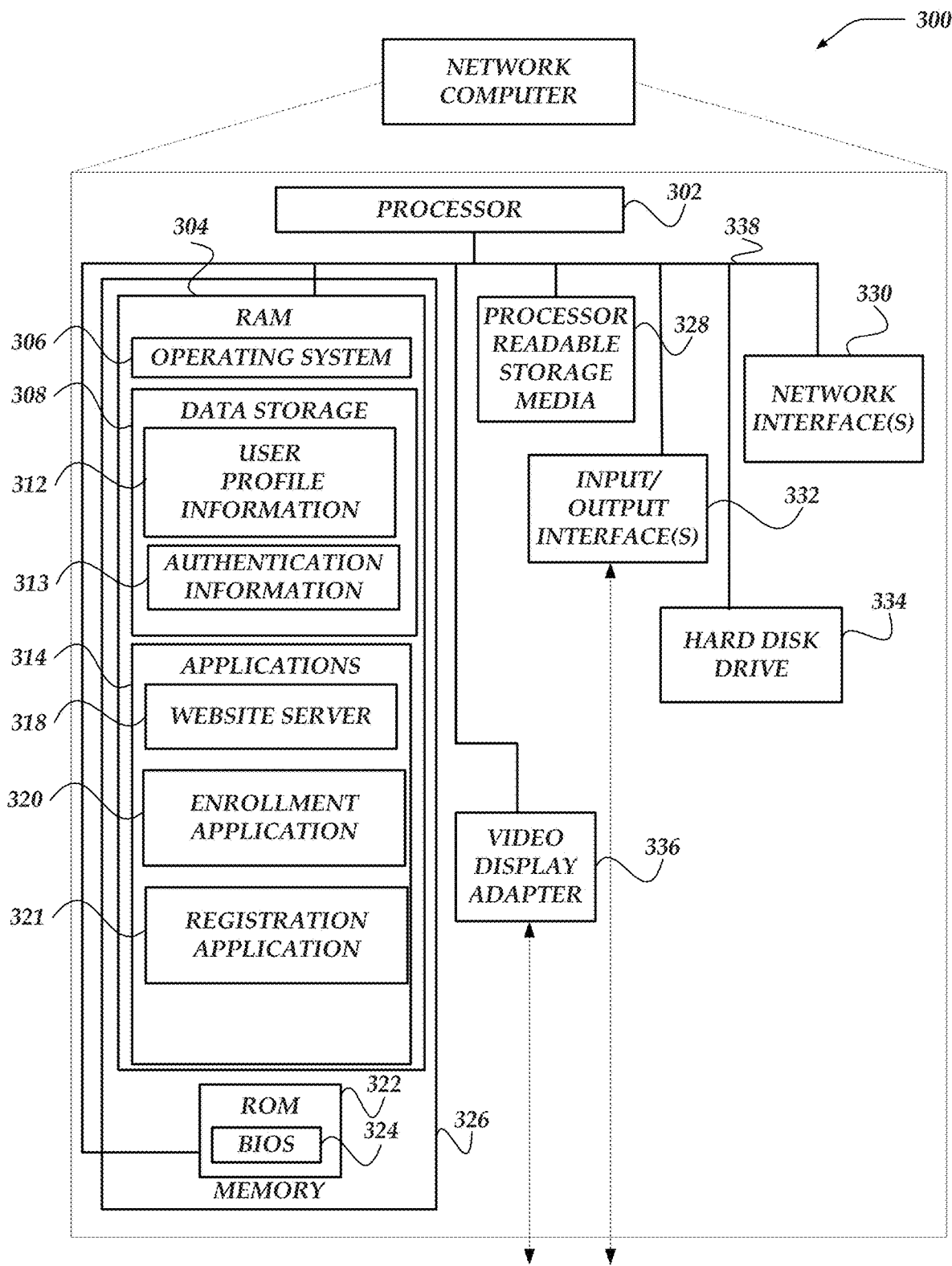
FIG. 3 is a diagram of an exemplary network computer that may be included in a system in accordance with at least one of the various embodiments.

FIG. 3 shows one embodiment of a network computer 300, according to one embodiment of the invention. Network computer 300 may include many more or less components than those shown. The components shown, however, are sufficient to disclose an illustrative embodiment for practicing the invention. Network computer 300 may be configured to operate as a server, client, peer, a host, cloud instance, or any other computer. Network computer 300 may represent, for example authentication server computer 116, and/or other network computers.

Network computer 300 includes processor 302, processor readable storage media 328, network interface unit 330, an input/output interface 332, hard disk drive 334, video display adapter 336, and memory 326, all in communication with each other via bus 338. In some embodiments, processor 302 may include one or more central processing units.

As illustrated in FIG. 3, network computer 300 also can communicate with the Internet, or other communication networks, via network interface unit 330, which is constructed for use with various communication protocols including the TCP/IP protocol. Network interface unit 330 is sometimes known as a transceiver, transceiving device, or network interface card (NIC).

Network computer 300 also comprises input/output interface 332 for communicating with external devices, such as a keyboard, or other input or output devices not shown in FIG. 3. Input/output interface 332 can utilize one or more communication technologies, such as USB, infrared, NFC, Bluetooth, or the like.

Memory 326 generally includes RAM 304, ROM 322 and one or more permanent mass storage devices, such as hard disk drive 334, tape drive, optical drive, and/or floppy disk drive. Memory 326 stores operating system 306 for controlling the operation of network computer 300. Any general-purpose operating system may be employed. Basic input/output system (BIOS) 324 is also provided for controlling the low-level operation of network computer 300.

Although illustrated separately, memory 326 may include processor readable storage media 328. Processor readable storage media 328 may be referred to and/or include computer readable media, computer readable storage media, and/or processor readable storage device. Processor readable storage media 328 may include volatile, nonvolatile, non-transitory, non-transitive, removable, and non-removable media implemented in any method or technology for storage of information, such as computer readable instructions, data structures, program modules, or other data. Examples of processor readable storage media include RAM, ROM, EEPROM, flash memory or other memory technology, CD-ROM, digital versatile disks (DVD) or other optical storage, magnetic cassettes, magnetic tape, magnetic disk storage or other magnetic storage devices, or any other media which can be used to store the desired information and which can be accessed by a computer.

Memory 326 further includes one or more data storage 308, which can be utilized by network computer 300 to store, among other things, applications 314 and/or other data. For example, data storage 308 may also be employed to store information that describes various capabilities of network computer 300. The information may then be provided to another computer based on any of a variety of events, including being sent as part of a header during a communication, sent upon request, or the like. Data storage 308 may also be employed to store messages, web page content, or the like. At least a portion of the information may also be stored on another component of network computer 300, including, but not limited to processor readable storage media 328, hard disk drive 334, or other computer readable storage medias (not shown) within network computer 300.

Data storage 308 may include a database, text, spreadsheet, folder, file, or the like, that may be configured to maintain and store user account identifiers, user profiles, email addresses, IM addresses, and/or other network addresses; or the like. Data storage 308 may further include program code, data, algorithms, and the like, for use by a processor, such as processor 302 to execute and perform actions. In one embodiment, at least some of data store 308 might also be stored on another component of network computer 300, including, but not limited to processor-readable storage media 328, hard disk drive 334, or the like.

Data storage 308 may include user (e.g. authentication, authorization and/or biometric) profile information 312. In at least one of the various embodiments, user profile information 312 may include information, such as, one or more files, that include authentication (e.g. biometric) data for one or more users, or the like, used for authentications of wearable authentication devices. Also, in at least one of the various embodiments, data storage 308 may include authentication information 313 that may include information about users, access points, access control lists, or the like.

Applications 314 may include computer executable instructions, which may be loaded into mass memory and run on operating system 306. Examples of application programs may include transcoders, schedulers, calendars, database programs, word processing programs, Hypertext Transfer Protocol (HTTP) programs, customizable user interface programs, IPSec applications, encryption programs, security programs, SMS message servers, IM message servers, email servers, account managers, and so forth. Applications 314 may also include, enrollment application 320 for enrolling and/or activating authentication devices. Application mat also include registration application 321 for authenticating users by employing biometric information, authentication devices, additional conditions, or the like.

Website server 318 may represent any of a variety of information and services that are configured to provide content, including messages, over a network to another computer. Thus, website server 318 can include, for example, a web server, a File Transfer Protocol (FTP) server, a database server, a content server, email server, or the like. Website server 318 may provide the content including messages over the network using any of a variety of formats including, but not limited to WAP, HDML, WML, SGML, HTML, XML, Compact HTML (cHTML), Extensible HTML (xHTML), or the like.

Illustrative Authentication Device

In at least one of the various embodiments, a wearable authentication device, such as, authentication device 106 may be any device that may be employed, typically, worn or held, by a user and is capable of receiving authentication data as input, such as for example, offering a user input interface for the manual input of authentication data (username, password, code, PIN, etc.) and/or being operable to obtain a biometric signal or like input. Non-limiting examples of wearable authentication devices are a wristband, wristwatch, bracelet, necklace, ring, belt, glasses, clothing, hat, anklet, headband, chest harness or earring(s), or, in the context of a biometric device, any other item that is capable of obtaining a biometric signal. The wearable authentication device can also be incorporated into clothing. In another embodiment, the wearable authentication device may comprise multiple input interfaces so to access distinct authentication inputs (e.g. combined manual and biometric inputs, multiple biometric inputs, etc.).

While wearable authentication devices are contemplated in the illustrated embodiments, for at least one of the various embodiments, authentication devices within the scope of these innovations are not limited exclusively to wearable devices. In at least one of the various embodiments, authentication devices in non-wearable form factors may be considered to be within the scope of the innovations described herein. For example, a fixed authentication device embedded in a chair, desk, handle bar, or the like, or combination thereof. Likewise, authentication devices that may be held rather than worn are also contemplated to be within the scope of the innovations described herein. However, in the interest of clarity and brevity most of the discussion and examples presented herein are described in terms of wearable authentication devices. One of ordinary skill in the art will appreciate the other authentication device form factors are within the scope of these innovations and are envisaged.

In at least one of the various embodiments, a user of a wearable authentication device may be authenticated with one or more biometric technologies or sensors that may capture biometric signals and/or data that represent biometric features that may be employed to uniquely identify the user. The uniqueness of a biometric feature may be directly related to the underlying inter-individual differences in a population. Some non-limiting examples of biometric data that may be employed to uniquely identify a user are gait, heart rate, galvanic skin response, temperature, fingerprint, voice or voiceprint, body electrical characteristic, body thermal characteristic, iris pattern, vein pattern, eye vein pattern, facial or other anatomical structure, electrocardiogram, photoplethysmogram, electromyogram, electroencephalogram, transient otoacoustic emissions, phonocardiogram, DNA, one or more chemical markers, one or more biochemical markers, skin-color variation or discoloration, or perspiration. In at least one of the various embodiments, authentication is performed by the authentication device. However, additionally or alternatively, authentication may be performed by an authorized registration application.

In at least one of the various embodiments, a physiological feature is also captured, not to identify a user (although this is also contemplated, with various degrees of weight given based on the uniqueness of the physiological signal for use as a secondary biometric feature type), but to determine whether the authentication data was received from a genuine living human being, and/or to determine whether the genuine living human from whom the authentication data was captured is wearing the authentication device.

For example, in some embodiments, an authentication process invoked by or via the device will be satisfied upon confirming authentication of the input authentication data and concurrent live user presence via the device's physiological feature. Such live user presence confirmation may further or alternatively persist during use to confirm live user presence in maintaining user authorizations and otherwise revoke such authorizations if the physiological input is lost (e.g. if the device is removed from the user, or, vice-versa).

In some embodiments, as noted above, the user authentication interface and physiological sensor will be configured so to concurrently with the user during authentication, for example, where authentication data input requires user contact (e.g. fingerprint and/or data input) and where such contact invariably results in user contact with a complementary physiological sensor (e.g. probe, interface and/or contact thereof). It will, however, be appreciated that such concurrent user contact need not necessarily proceed through a common interface but rather, may require authentication and physiological interfaces to be closely disposed or arranged to facilitate concurrent or sequential contact. In some embodiments, a physiological signal may further require two concurrent physical contact points by a same genuine user, for example in the context of a ECG, which can be achieved in some embodiments, through a finger input interface and wrist interface in a wristband or likewise configured device.

For example, because an electrocardiogram requires two points of contact across the heart to be detected, an electrocardiogram (ECG) is used in at least one of the various embodiments to validate that a fingerprint (e.g. authenticating biometric data) is being captured by a wearer of an authentication device (e.g. as opposed to a fingerprint from a person standing next to the wearer). The ECG may also be used to defeat a replay attack by validating that the fingerprint is captured from a genuine living person, as opposed to a fingerprint mold intended to fool the authentication device. Both validations are accomplished by positioning one of the ECG sensors proximate to (e.g. adjacent to, on top of, around the bezel of, as part of, etc.) the fingerprint sensor, such that, in one embodiment, both biometric and physiological features are captured concurrently, from the same finger. Additionally or alternatively, authentication and physiological features may be captured sequentially, such that within a defined period of time chosen to prevent another person from substituting their finger, or in parallel. Additionally or alternatively, authentication and physiological features may be captured within a defined period of time such that the wearable authentication device has not detected the removal of the finger between captures. It will be appreciated that while biometric authentication is considered in the above-noted examples, other authentication mechanisms may also be considered to concurrently or sequentially benefit from physiological user presence confirmation. For instance, a user input interface for receiving as input manually entered authentication data (e.g. touch sensitive screen or interface) may double as or be juxtaposed to a physiological probe so to provide a similar effect.

Following from the above example, in one or more of the various embodiments, a second ECG sensor is positioned so as to contact the wrist of the wearer. In this way, an ECG signal is enabled to travel from the heart, through one arm, through one of the ECG sensors, out the other ECG sensor, through the other arm, and back to the heart. Without this electrical connection—e.g. if another person is providing the fingerprint or manual input, such that the ECG does not flow through the fingerpath of the user touching the authentication interface—the authentication device will determine that the authentication data is not being provided by the wearer of the authentication device. Similarly, if the electrical connection is distorted or in any way modified by the use of a fingerprint mold, for example, the ECG sensor will determine that the fingerprint is not being provided by the wearer of the authentication device.

Throughout this disclosure, and particularly with reference to the illustrative example presented above, for clarity and brevity, authentication features are predominantly discussed as biometric features, and more predominantly fingerprints, and physiological features are predominantly discussed as ECGs, but other types of authentication, and particularly biometric features may be considered, such as but not limited to finger-veins and galvanic skin responses, to name a few. For instance, in the context of the illustrative example provided above, biometric authentication feature may be any feature that is captured based on contact with the user, whereas a physiological feature may be any feature that can be captured, at least in part, using the same body part as is used to capture the biometric feature, and which can determine if the wearable authentication device is worn by the owner of that same body part. While fingerprint and ECG are discussed in greater detail below as options for providing authentication and live user presence confirmation, such examples should not be considered to limit the general scope and nature of the present disclosure, but rather, merely serve as one example consistent with various embodiments of the present disclosure.

In at least one of the various embodiments, the wearable authentication device may include an onboard power source to enable the authentication device to perform the required functions, such as obtaining the authentication and/or physiological signals, transmitting and receiving these and related control signals, and in some embodiments, maintaining a detector for detecting the removal of the wearable authentication device, for example, such as an electronic continuity detector. Any power source known to the skilled person is acceptable, with non-limiting examples being battery, photovoltaic, kinetic, or microgenerator, thermal, piezo-electric generator, inductive charging, and wireless power transfer.

The wearable authentication device includes one or more radios/transceivers for transmitting and receiving communications. The one or more radios/transceivers may transmit and receive communications from systems installed at access points, e.g. transmitting authorization to gain access to one or more access points.

In one example, the wearable authentication device may incorporate a wireless connectivity module such as Bluetooth 4.0 Low Energy (BLE), Near-Field Communications (NFC), WiFi, or other wireless technology capable of transmitting and receiving functions. In one embodiment, a BLE radio may be used because it may consume significantly less power when communicating in short bursts. In this way, a battery or other power source used to power the wearable authentication device may have an extended life, in some cases on the order of multiple weeks.

In at least one of the various embodiments, the radios and/or transceivers may be used to transmit data during initialization and authentication, identify the user, and to establish a unique user profile associated with the user and the wearable authentication device. The same or other the radios and/or transceivers included in a wearable authentication device may also transmit and receive motion data, time of flight, signal strength, and proximity data in order to be aware of local access points. In at least one of the various embodiments, the radios and/or transceivers may also be used to receive a positive authentication message that puts the wearable device into an authenticated state, as well as to prompt the user of notification events.

In at least one of the various embodiments, the wearable authentication device may be arranged to include proximity sensors for sensing an access point (physical or logical), or an authorized application. In one embodiments, a feature of the Bluetooth 4.0 standard which may be used by radios and/or transceivers included in the authentication device. Also, in at least one of the various embodiments, the wearable authentication device may be configured to transmit a beacon signal along with the transmitting signal strength. Accordingly, the receiving device may use this information, along with the received signal strength, to estimate the proximity of the wearable authentication device. Non-limiting exemplary uses of the proximity data may include: only unlocking a device when the proximity is within a specified range, i.e., a door lock is only unlocked when the authorized user is within a certain distance, such as 50 cm; a "digital leash" which warns the user when a paired device is no longer within a certain proximity; revoke authorized access to a given resource upon the device moving beyond a designated authorization distance, zone or area, or the like.

In at least one of the various embodiments, in addition to being used to confirm that the person providing the fingerprint is wearing the wearable authentication device, as described above in one example, the wearable authentication device may utilize ECG biometric authentication as a secondary, confirmatory form of biometric authentication in addition to the primary authentication mechanism, e.g. fingerprint, finger-vein, etc. In at least one of the various embodiments, ECG biometric authentication technology may use unique features of a user's electrocardiogram (ECG) to create a highly personalized biometric signature for that individual. Like other biometric characteristics, the ECG is universal, unique for every individual, and permanent over time. An ECG may be recorded for every living user, with no exclusion criteria. In addition, studies have shown that even though aspects of the ECG signal may get distorted with time and aging, the overall diacritical characteristics are observable. In the case of ECG, the uniqueness of the biometric feature is a result of several parameters of the cardiac function that control the waveforms. Electrophysiological variations of the myocardium such as the heart mass orientation and exact position, or the timing of depolarization and repolarization add to the idiosyncratic properties of every person's ECG waveforms.

In at least one of the various embodiments, one or more well-known ECG biometrics algorithms may analyze the overall pattern of the signal waveform rather than specific characteristics of the heart-beats and are therefore referred to as "fiducial-independent". One of the core algorithms is referred to as the AC/LDA (Autocorrelation/Linear Discriminant Analysis) and has become a standard for the comparison of fiducial dependent and independent algorithms.

In at least one of the various embodiments, a number of mechanisms for initiation of ECG capture and authentication may be used. For example, the authentication device may be arranged to automatically sense when a top electrode is touched, such as using an embedded "lead on/off" detection system, optionally with notification of the lead status to the user. Additionally or alternatively, ECG capture is initiated in response to capturing primary authentication data, such as a fingerprint.

In at least one of the various embodiments, when biometric authentication is initiated through fingerprint, one or more images of a finger are captured and stored in a biometric profile 210. In one or more of the various embodiments, when authentication is performed by the registration application, the one or more images of the finger are transmitted to the registration application for processing and stored in biometric profile information 312. Similarly, once ECG capture and liveness validation are initiated, the single-channel filtered ECG data may be processed by the wearable authentication device and/or transmitted to the registration application for processing. In another embodiment, the images of the finger and ECG capture and liveness validation are processed and stored on the device.

Using a function within the registration application, biometric/user enrollment may be initiated, wherein the user touches the wearable authentication device, and then a biometric feature (e.g. a fingerprint, finger-vein) and an ECG are captured and processed by the wearable authentication device, and/or are transmitted to the registration application. This process may take as little as about 1 second and up to a few seconds, a minute, or a few minutes depending on the level of interaction with the user with the wearable authentication device and the type of authentication signals being obtained.

In at least one of the various embodiments, the user (e.g. biometric) profile may be created in a number of different ways. In one way, the biometric signal may be transmitted to a cloud service, where the processing is performed on the cloud servers to generate the biometric profile. Alternatively, the biometric signal may be processed on the registration application to generate the biometric profile.

In at least one of the various embodiments, once the biometric profile is created, it may be associated with a user and stored within a cloud service. Also, in at least one of the various embodiments, the biometric profile may be transmitted to the registration application or stored locally just on the device. In at least one of the various embodiments, the biometric profile may be stored on a wearable authentication device that is arranged to include the processing power required to authenticate the user. In another alternative, the processing for the creation of the biometric profile may be performed on the registration application or in the wearable authentication device itself.

In at least one of the various embodiments, the wearable authentication device may include one or more of: a CPU or system on a chip (SOC) which acts as the controller, a wireless transceiver, an antenna, audible and haptic feedback, and a user interface. The controller may be operative for controlling the overall operation of the wearable authentication device. The controller functionality may be implemented within, for example, one or more digital processing devices within the wearable authentication device. The wireless transceiver is operative for supporting wireless communication between the wearable authentication device and one or more other wireless entities including the AAD and wireless access points. In one embodiment, separate transceivers are provided within the wearable authentication device to support wireless communication between the wearable authentication device and other systems or devices. The wireless transceiver may also be coupled to one or more antennas to facilitate the transmission and reception of wireless signals. Any type of antenna(s) may be used including, for example, a dipole antenna, a patch antenna, a helical antenna, an antenna array, trace antenna, and/or others, including combinations of the above.

In at least one of the various embodiments, a user interface may be operative for providing an interface between a user and the wearable authentication device. The user interface of a authentication device may include structures such as, for example, a keyboard, a liquid crystal display (LCD), light emitting diode (LED), active-matrix organic light-emitting diode (AMOLED), passive-matrix organic light-emitting diode (PMOLED), capacitive touch screen, a speaker, a microphone, mouse, stylus, one or more physical or electronic buttons, and/or any other form of device or structure that enables a user to input information or commands to the wearable authentication device or receive information or a notification from the device.

In one embodiment, the controller may first determine if the wearable authentication device (and, therefore, the user) is within a predetermined distance or proximity to an access point. In one example, if the wearable authentication device is within proximity of an access point and the wearable authentication device transmits a control signal to the access point indicating that the user has been authenticated, the receiver at the access point may automatically enable access to the user. If the wearable authentication device later goes outside the predetermined distance from the access point, the access point may be locked. In one example, if the access point is a security protected desktop computer and the preauthorized user wearing their preauthorized wearable authentication device temporarily leaves her desk to go to lunch, the computer will automatically lock so that no one else may use it in the user's absence. Similarly, if the access point is a smartphone and the smartphone is inadvertently left somewhere by the user, or is stolen, the smartphone will automatically lock up and thus be unusable by an unauthorized party in possession thereof. When the user wearing the preauthorized wearable authentication device again comes within a predetermined distance of the smartphone, the smartphone will simply be unlocked without having to repeat the automatic log in procedure, assuming that the wearable authentication device remains preauthorized.

In at least one of the various embodiments, the wearable authentication device, no matter which type of authentication data is used for authentication, should be able to maintain contact with the user (e.g. via onboard physiological sensor) such that in the case that the wearable device is removed from the user, the wearable device will require re-initialization prior to authorizing access control. The purpose of maintaining contact of the wearable authentication device with the user is to ensure that an authorized authentication device cannot be transferred to a different user without requiring reauthorization. Accordingly, although skin or body contact is not required at all times while the wearable device is in its authenticated state, the wearable device should be on the user in such a way that removal of the wearable will put the wearable device back to its unauthenticated state. In the unauthenticated state, the wearable authentication device is not enabled to transmit a control signal to an access point. The security of at least some of the herein described embodiments depends on ensuring that removal of the wearable device from the user is reliably detected. Accordingly, the wearable authentication device may be arranged such that removal from the user's body may be easily detected.

In one particular embodiment, as a complement to or in the absence of a physiological sensor, the wearable device may comprise a sensored adjustable and/or openable clasp to assist the user with putting on and removing the wearable device while monitoring removal of the device form the user in authenticated use. For example, removal of the wearable device may be sensed by the wearable authentication device, for example, by opening the clasp, or again by cutting the band, or generally severing an electrical conduit such as an electronic continuity detector. One exemplary electronic continuity detector that may be used to detect device removal comprises a simple circuit within the wearable device that runs around the entire wrist and is broken when the clasp is opened or the band is cut. Other types of device removal detection may be used, for example, including disruption in skin contact detection by way of conductivity, heat flux, galvanic skin response or motion, or periodic or continuous biometric signal detection. Yet other non-limiting examples of device removal detection embodiments may include pulse detection, skin temperature detection, ambient temperature detection, blood flow detection, pressure detection, ambient light detection, electromagnetic field detection, respiration detection, heart rate detection, electrocardiogram detection, photoplethysmogram detection, electromyogram detection, electroencephalogram detection, near infra-red detection, skin-color detection, close magnetic contact detection, and mechanical switch detection.

In at least one of the various embodiments, additional sensors may be incorporated into the device to obtain additional biometric or environmental readings. Some non-limiting examples of an additional sensor are motion sensor, proximity sensor, barometric sensor, pressure sensor, thermometer, microphone, near infrared sensor, light sensor, GPS sensor, capacitive sensor, gyroscope, manometer, camera, humidity sensor, hall sensor, galvanic skin sensor, photoplethysmogram sensor, electroencephalogram sensor, electromyogram sensor, blood flow sensor, bioimpedance sensor, otoacoustic emission sensor, optical sensor, altimeter sensor or UV light sensor. These additional sensors may provide one or more contextual signals such as the location of the wearable device and/or proximity to trusted environments.

In at least one of the various embodiments, a wearable authentication device may comprise one or more motion sensors that may be used for a variety of purposes, including but not limited to, user input (e.g., tap detection), activity tracking (e.g., pedometer, sports, fitness, etc.), gesture recognition, or the like. In one embodiment, a wearable authentication device may incorporate a six-axis motion sensor using an integrated accelerometer and gyroscope or a 9-axis motion sensor using integrated accelerometer, gyroscope, and magnetometer application-specific integrated circuit (ASIC). Embedded motion sensors may also be utilized for simple gesture recognition to indicate user intent, such as for example gestures may be used to distinguish between user intents to unlocking different locks on an automobile, such as, the driver door, passenger door, the trunk, or the like. In this way, computational requirements on the wearable authentication device may be kept at a minimum.

In at least one of the various embodiments, the wearable authentication device may be arranged to include notification devices and procedures to alert the user of one or more notification events. Some non-limiting examples of these include one or more notification LEDs and/or a vibration motor. A notification event may be an event detected by the wearable authentication device that the user should be aware of. These events may include: when the wearable device has been put into an authenticated state; when the wearable authentication device is communicating with other devices; when the wearable device is sensing motion; and/or when some event has occurred on a paired device, such as receiving an email or text. A paired device may be any device or system that interacts with the wearable authentication device.

In at least one of the various embodiments, the wearable device may also comprise other components such as a display screen, input devices (such as, for example, button, switch, keypad or touchscreen), timepiece/timers, tracking or global positioning (GPS) detector activity, or physiology or emotion tracking. In at least one of the various embodiments, authentication device may be arranged to indicate proximity to other devices. In at least one of the various embodiments, wearable authentication devices may be arranged to include additional electronics for storing data for access and use not related to the presently described security system.

Figure 4A:
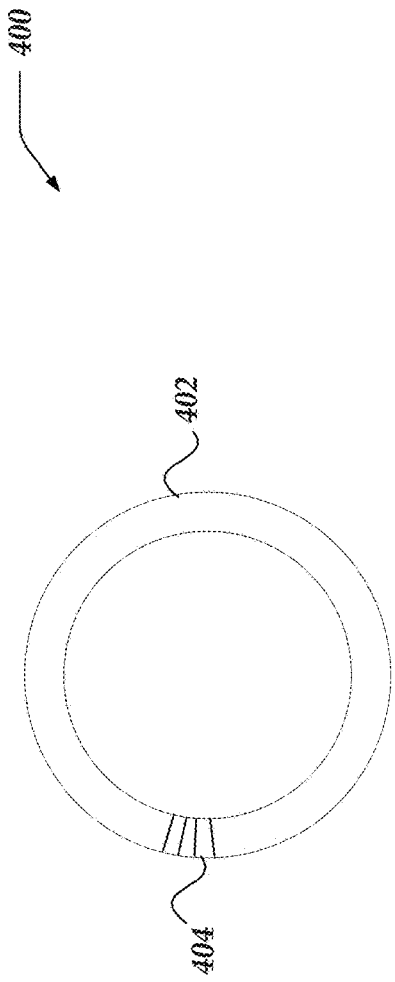
FIG. 4A and FIG. 4B are schematic physical and logical diagrams, respectively, of a wearable user authentication/access authorization device, in accordance with at least one of the various embodiments.
Figure 4B:
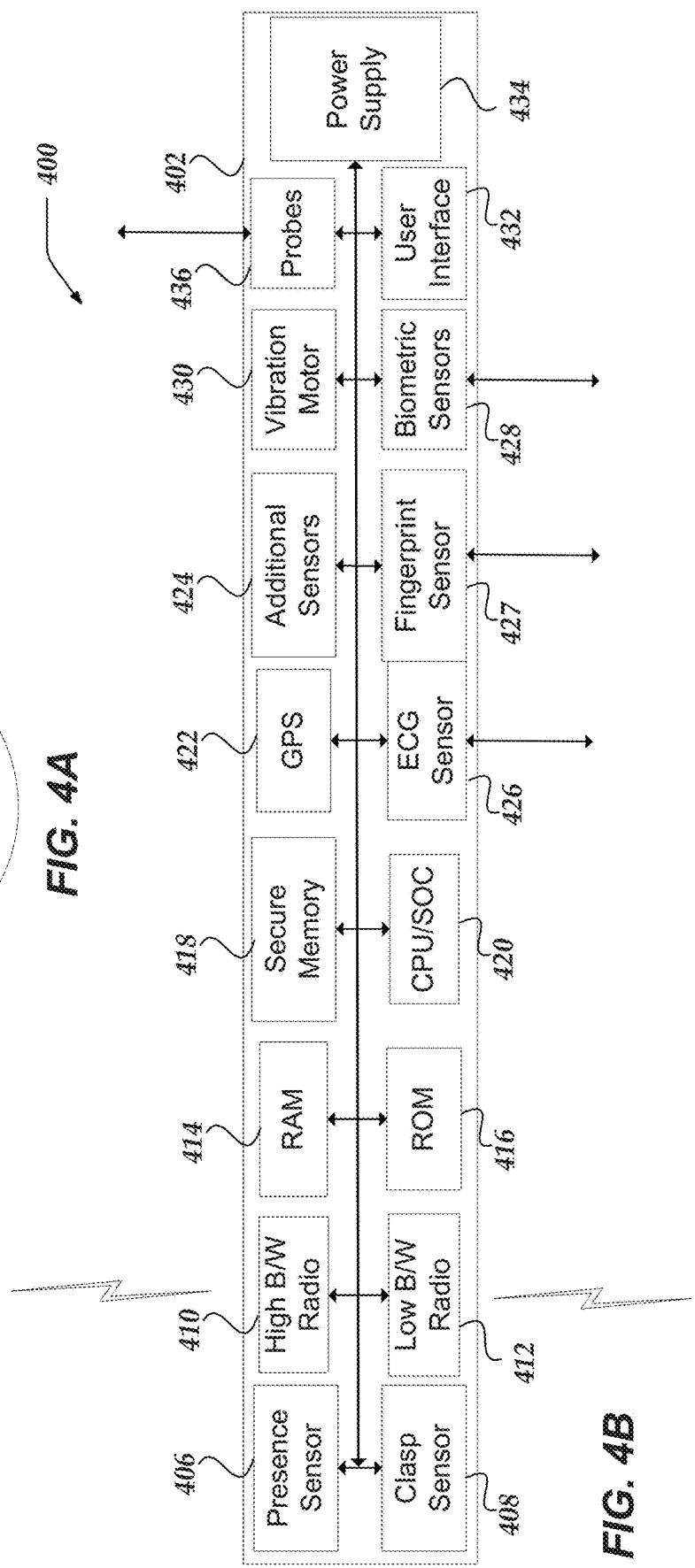

FIG. 4A and FIG. 4B are schematic physical and logical diagrams, respectively, of a wearable user authentication/access authorization device, in accordance with at least one of the various embodiments.

FIG. 4A illustrates authentication device 400 that is arranged as a wearable wristband/bracelet. In at least one of the various embodiments, wristband 402 may be arranged to include various hardware components, probes, sensors, and software for capturing authentication (e.g. biometric) and/or physiological signals from its wearer; making a determination whether authentication data was captured from a live person wearing the wearable wristband/bracelet based on a captured physiological feature; communication with a registration application or access point; authentication of a wearer, or the like, as discussed above. Further, in at least one of the various embodiments, wristband 402 may include an adjustable clasp mechanism, such as, clasp 404, for detecting if a wearer removes wristband 402 from his or her wrist. For example, in at least one of the various embodiments, if an authentication device detects that the clasp is opened, it may automatically de-authenticate itself.

FIG. 4B schematically illustrates some of the various components that may be comprised in an authentication device in accordance with at least one of the various embodiments. In at least one of the various embodiments, wristband 402 may include one or more presence sensors, such as, presence sensor 406, presence sensors may be arranged to determine if authentication device 402 is in the presence of a wearer, registration application, access point, or the like, or combination thereof. Also, in at least one of the various embodiments, authentication device 402 may include one or more radios or transceivers, such as, high bandwidth radio 410 and low bandwidth radio 412. These radios may enable a authentication device to communicate with other computer or devices, such as, access points, authentication servers, or the like, or combination thereof.

In at least one of the various embodiments, clasp sensor 408, may be arranged to determine if the clasp, or other securing mechanism, is opened or closed. In at least one of the various embodiments, an opened clasp may indicate that the authentication device may be separated from its authenticated user. Accordingly, for example, the authentication device may be arranged to automatically reset or otherwise de-authenticate itself if clasp sensor 408 indicates that the authentication device is removed from the wearer. Further, removal of the wearable device may be sensed by the wearable authentication device for example, by opening the clasp, cutting the band, or generally severing an electrical conduit such as an electronic continuity detector. One exemplary electronic continuity detector that may be used to detect device removal comprises of a simple circuit within the wearable device that runs around the entire wrist and is broken when the clasp is opened or the band is cut. Other types of device removal detection may be used, for example, including disruption in physiological signal such as skin contact detection by way of conductivity, heat flux, galvanic skin response or motion, or periodic or continuous biometric signal detection. Yet other non-limiting examples of device removal detection embodiments include physiological tests such as pulse detection, skin temperature detection, blood flow detection, pressure detection, electromagnetic field detection, respiration detection, heart rate detection, electrocardiogram detection, photoplethysmogram detection, electromyogram detection, electroencephalogram detection, near infra-red detection, skin-color detection, close magnetic contact detection, and/or non-physiological tests such as mechanical switch detection, ambient temperature detection, ambient light detection, etc.

In at least one of the various embodiments, as discussed above, authentication device 402 may be arranged to communicate with various devices, such as, access points, authentication servers and cloud services, or the like, or combination thereof. In at least one of the various embodiments, high bandwidth radio 410 may include radios for communication using high bandwidth mechanisms such as Wi-Fi, or the like. Low bandwidth radio 412 may represent components for communicating using low-power, shorter range radio systems such as, Bluetooth, Bluetooth Low Energy, NFC, RFID, or the like, or combination thereof. Further, in at least one of the various embodiments, these radios may be coupled to one or more antennas to facilitate the transmission and reception of wireless signals. Any type of antenna(s) may be used including, for example, a dipole antenna, a patch antenna, a helical antenna, an antenna array, trace antenna, and/or others, including combinations of the above.

In at least one of the various embodiments, RAM 414 may be non-volatile and/or volatile random access memory for storing information for operation of authentication device 402. In at least one of the various embodiments, all or portions of the contents of RAM 414 may be erased if the authentication device is removed of its wearer. Likewise, in at least one of the various embodiments, ROM 416 may contain data and/or instructions for the operation of the authentication device. In at least one of the various embodiments, ROM 416 may be "flashable," enabling it to be updated with system updates provided by a registration application or a biometric server service.

In at least one of the various embodiments, secure memory 418 may be a hardened tamper resistant memory device that is resistant to physical tampering. In at least one of the various embodiments, sensitive information such as cryptographic keys, biometric profiles derived from captured biometric features, and the like may be stored in secure memory 418.

In at least one of the various embodiments, authentication device 402 may be arranged to include CPU or System-on-a-Chip (SOC) for controller the operations of the authentication device. The performance capability of CPU/SOC 420 may vary depending on how much processing authentication device 402 is intended to perform.

In at least one of the various embodiments, GPS transceiver 422 may represent the radios, hardware, and instructions (e.g., software) for receiving geo-location. GPS transceiver 422 may determine the physical coordinates of authentication device 402 on the surface of the Earth. GPS transceiver 422 typically outputs a location as latitude and longitude values. However, GPS transceiver 422 may also employ other geo-positioning mechanisms, including, but not limited to, triangulation, assisted GPS (AGPS), Enhanced Observed Time Difference (E-OTD), Cell Identifier (CI), Service Area Identifier (SAI), Enhanced Timing Advance (ETA), Base Station Subsystem (BSS), or the like, to further determine the physical location of authentication device 402 on the surface of the Earth. It is understood that under different conditions, GPS transceiver 422 may determine a physical location within millimeters for authentication device 402; and in other cases, the determined physical location may be less precise, such as within a meter or significantly greater distances.

In at least one of the various embodiments, additional sensors 424 represent one or more sensor systems including, additional sensors such as accelerometers, motion sensors, proximity sensors, barometric sensors, pressure sensors, thermometers, microphones, near infrared sensors, light sensors, capacitive sensors, gyroscopes, manometers, cameras, humidity sensors, hall sensors, galvanic skin sensors, photoplethysmogram sensors, electroencephalogram sensors, electromyogram sensors, blood flow sensors, bioimpedance sensors, otoacoustic emission sensors, optical sensors, altimeter sensors, UV light sensors, or the like.

In at least one of the various embodiments, as discussed above, authentication device 402 may be arranged to include a variety of biometric and/or physiological sensors and probes for detecting, sensing, and/or sampling a variety of biometric and/or physiological signals from the wearer. ECG sensors 426 represent one or more sensors for detecting, sensing, and/or sampling ECG information as described above. Fingerprint sensor 427, depicted adjacent to ECG sensor 426 to indicate a physical proximity on the physical device, represents a sensor for scanning fingerprints, as described above. Likewise, biometric sensors 428 represent one or more sensors for detecting, sensing, and/or sampling other biometric information as described above. In some embodiments, sensors may be comprised of one or more probes, contacts, or the like. In some embodiments, one or more probes or contacts, represented by probes 436, may be used for to collect signals for more than one sensor.

In at least one of the various embodiments, ECG sensor 426 may be adjacent to, surrounding, internal to, integrated with, and/or otherwise close enough to fingerprint sensor 427 that a user may easily place a finger on probes for both sensors at the same time. In another of the various embodiments, probes for ECG sensor 426 may be located next to/integrated with one or more probes for fingerprint sensor 427 such that it is difficult if not impossible to selectively activate one sensor but not the other, and such that it is difficult if not impossible for two fingers, each from different people, to individually be captured by the different sensors.

In one or more of the various embodiments, one or more probes or other components may be shared by two or more sensors. For example, in some embodiments, a sensor for detecting body temperature, heart rate, ECGs, or the like, may be arranged to share the same probe.

In at least one of the various embodiments, biometric sensor 402 may be arranged to include a variety of components for interacting with the wearer. Vibration motor 430 may enable the authentication device to vibrate to notify the wearer of various changes in state, or the like (as discussed above). Likewise, user interface 432 may comprise elements that enable a user to provide input to the authentication device or for receiving output from the authentication device as discussed above, including biometric data that may be employed to uniquely identify a user, such as gait, heart rate, galvanic skin response, temperature, fingerprint, voice or voiceprint, body electrical characteristic, body thermal characteristic, iris pattern, vein pattern, eye vein pattern, facial or other anatomical structure, electrocardiogram, photoplethysmogram, electromyogram, electroencephalogram, transient otoacoustic emissions, phonocardiogram, DNA, one or more chemical markers, one or more biochemical markers, skin-color variation or discolouration, perspiration, or the like. Also, in at least one of the various embodiments, user interface 432 may include a key pad, buttons, LED's microphone (for voice commands), or the like, or combination thereof.

Also, in at least one of the various embodiments, power source 434 may be arranged to provide power of operating authentication device 402. Power source 434 may include various batteries, storage cells, power adapters, chargers, or the like, as well as, power sources such as, photovoltaic, kinetic, or microgenerator, thermal, piezo-electric generator, inductive charging, and wireless power transfer or the like, or combination thereof.

One or ordinary skill in the art will appreciate that authentication device 402 is a non-limiting example of an authentication device that is in accordance at least one of the various embodiments. Even though authentication device 402 represents a wristband wearable authentication device, authentication devices within the scope of these innovation may be arranged in other form factors, such as those discussed above.

Further, in at least one of the various embodiments, some or all of components described in FIG. 4B and/or elsewhere in this paper may be implemented in hardware, including, dedicated (custom) hardware, ASICs, FPGAs, or the like. Likewise, these components or portions thereof may be implemented in whole or in part using software.

Figure 5A:
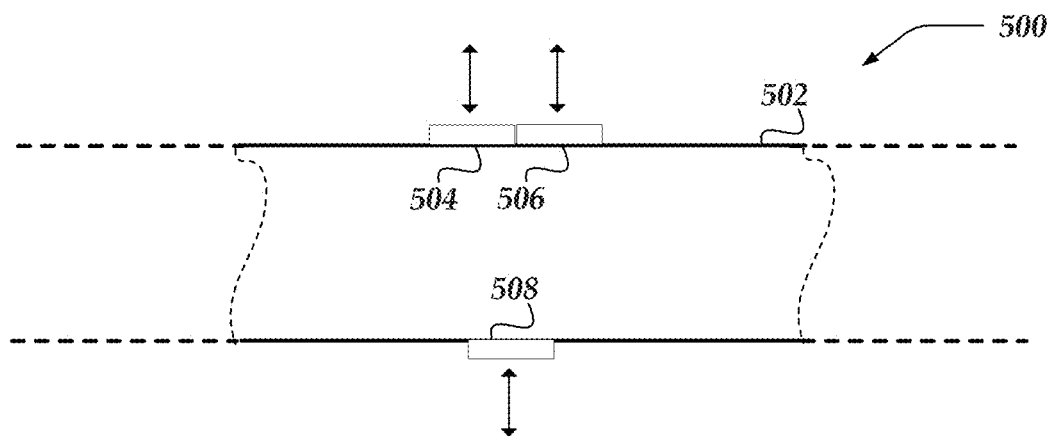
FIG. 5A is a logical schematic diagram of a biometric device showing sensors for fingerprint scanning and electrocardiogram signal capturing in accordance with at least one of the various embodiments.

FIG. 5A illustrates a logical schematic of authentication device 500 showing sensors for fingerprint scanning and ECG signal capturing in accordance with at least one of the various embodiments. In at least one of the various embodiments, authentication device section 502 represents a side cross-section that highlights one arrangement for capturing fingerprints and ECG signals. In at least one of the various embodiments, fingerprint sensors in a authentication device may be arranged to receive signals from one or more probes, such as probe 504. Probe 504 may be a camera, scanner, or other device or component capable of capturing an signals that correspond to a fingerprint. ECG sensors may be arranged to uses probes, such as probe 506 and probe 508 that may be probe contacts (e.g., electrodes, conductive contacts, or the like) arranged to capture ECG signals upon direct contact of a user's skin. In at least one of the various embodiments, probe 504 and probe 506 are arranged to enable the user to touch with a finger of his or her opposite hand (the hand not wearing the authentication device). In at least one of the various embodiments, probe 508 is arranged to contact the skin of the user's wrist that is wearing the authentication device. Accordingly, a circuit may be made from one hand to the other, enabling ECG signals to be captured through the probes and provided to one or more sensors, concurrent with a fingerprint of the same finger being captured. Note, one of ordinary skill in the art will appreciate that other probes or sensor arrangements may be employed. Further, more or fewer probes or sensors may be arranged in different positions—however, the arrangement disclosed in FIG. 5B is at least sufficient for practicing the innovations described herein.

Figure 5B:
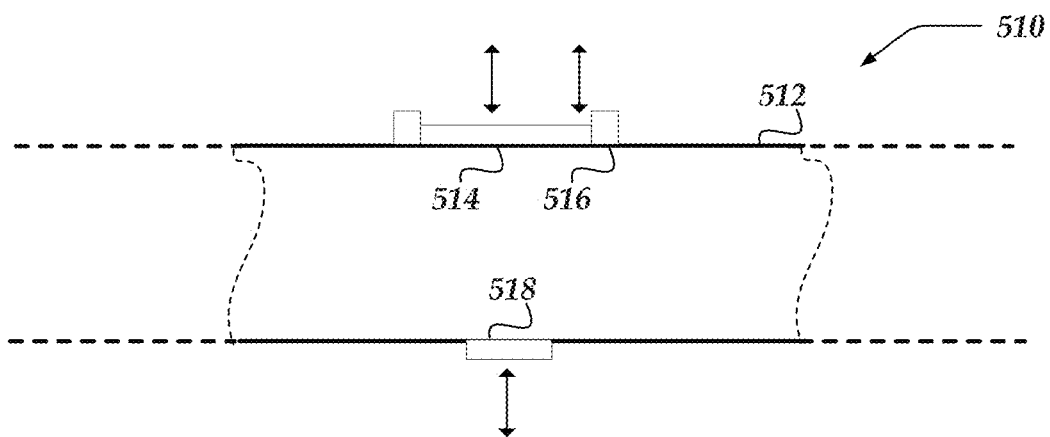
FIG. 5B is a logical schematic diagram of a biometric device showing another arrangement of sensors for fingerprint scanning and electrocardiogram signal capturing in accordance with at least one of the various embodiments.

FIG. 5B illustrates a logical schematic of authentication device 510 showing another arrangement of probes for fingerprint scanning and ECG signal capturing in accordance with at least one of the various embodiments. In at least one of the various embodiments, authentication device section 512 represents a side cross-section that highlights one arrangement for capturing fingerprints and ECG signals. In at least one of the various embodiments, a fingerprint sensor, such as, fingerprint sensor 427, may be arranged to receive signals from one or more probes, such as probe 514 which may be a camera, scanner, or other device capable of capturing an image of a fingerprint. Probe 516 represents a contact (e.g., conductive metal ring or bezel) arranged to capture ECG signals upon direct contact of a user's skin. In some embodiments, probe 516 may be positioned to contact a user's finger while that finger is in contact with probe 514.

In at least one of the various embodiments, because probe 514 and probe 516 are arranged to enable the user to simultaneously contact both probes with the same finger of his or her opposite hand (the hand not wearing the authentication device). Accordingly, while the user's fingertip is in contact with both probes at the same time, probe 514 captures the user's fingerprint information and probe 516 acts as an conductive contact.

In at least one of the various embodiments, probe 518 is arranged to contact the skin of the user's wrist that is wearing the authentication device. Accordingly, a circuit may be made from one hand to the other, enabling ECG signals to be captured through the probes and provided to an ECG sensor, such as, ECG sensor 426, concurrent with a fingerprint of the same finger being captured. Note, one of ordinary skill in the art will appreciate that other sensor arrangements may be employed. Further, more or fewer sensors may be arranged in different positions—however, the arrangement disclosed in FIG. 5B is at least sufficient for practicing the innovations described herein.

Figure 5C:
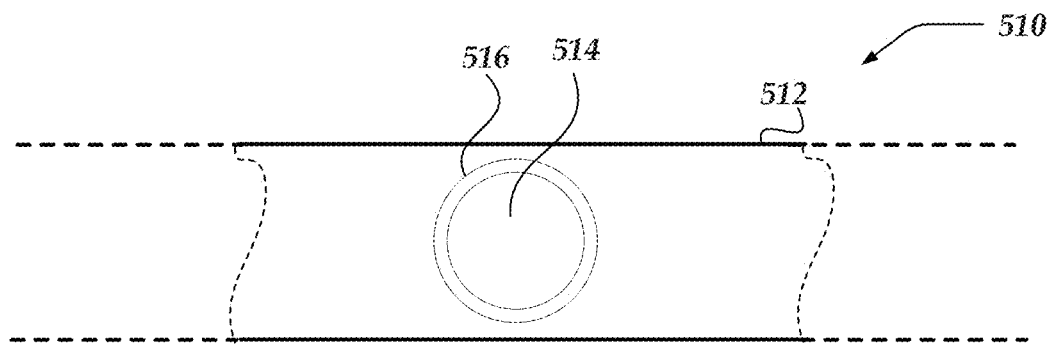
FIG. 5C is a logical schematic diagram of a biometric device showing a top view of the embodiment of FIG. 5B for fingerprint scanning and electrocardiogram signal capturing.

FIG. 5C illustrates a logical schematic of authentication device 510 showing a top view of the arrangement of sensors for fingerprint scanning and ECG signal capturing in accordance with at least one of the various embodiments. In at least one of the various embodiments, authentication device section 512 represents a top view of device 510 that highlights one arrangement for capturing fingerprints and ECG signals. In at least one of the various embodiments, a fingerprint sensor, such as, fingerprint sensor 427, may be arranged to receive signals from one or more probes, such as, probe 514. The one or more probes may include a camera, scanner, or other device capable of capturing an image of a fingerprint. Probe 516 represents a conductive contact (e.g., conductive metal ring or bezel) arranged to capture ECG signals upon direct contact of a user's skin. In some embodiments, probe 516 may be positioned to contact a user's finger while that finger is in contact with probe 514.

In at least one of the various embodiments, because probe 514 and probe 516 are arranged to enable the user to simultaneously contact both probes with the same finger of his or her opposite hand (the hand not wearing the authentication device). Accordingly, while the user's fingertip is in contact with both probes at the same time, probe 514 captures the user's fingerprint information and probe 516 acts as an conductive contact.

In at least one of the various embodiments, probe 518 (not visible in FIG. 5C) is arranged to contact the skin of the user's wrist that is wearing the authentication device. Accordingly, a circuit may be made from one hand to the other, enabling ECG signals to be captured through the probes, concurrent with a fingerprint of the same finger being captured. Note, one of ordinary skill in the art will appreciate that other sensor or probe arrangements may be employed. Further, more or fewer probes or sensors may be arranged in different positions—however, the arrangement disclosed in FIG. 5C is at least sufficient for practicing the innovations described herein.

Again, one or ordinary skill in the art will appreciate that authentication devices 502/512 are non-limiting examples of authentication devices that are in accordance at least some of the various embodiments. Even though authentication devices 502/512 represent wristband wearable authentication devices, authentication devices within the scope of these innovations may be arranged in other form factors, such as those discussed above.

Further, in at least one of the various embodiments, some or all of components described in FIG. 4B and/or elsewhere in this paper as it relates to the embodiments shown in FIGS. 5A-5C may also be implemented in hardware, including, dedicated (custom) hardware, ASICs, FPGAs, or the like. Likewise, these components or portions thereof may be implemented in whole or in part using software, firmware and/or combinations thereof.

As noted above, in at least one of the various embodiments, a wearable device may be arranged to omit features and components related to biometric sensors, biometric signals, or the like. In such embodiments, the preauthorization and/or authentication of the device may be based on non-biometric security factors. However, in the interest of brevity, the term biometric device is used throughout this description even though some wearable devices may be arranged to omit biometric features for authentication and/or preauthorization.

Illustrative Operation

FIGS. 6-15 represent an illustrative operation of various functions, features and processes contemplated by the embodiments described herein. For simplicity, these examples will consider embodiments relying on biometric authentication though other authentication mechanisms may be considered in combination therewith, or as an alternative thereof, as described above. In at least one of the various embodiments, processes 600, 700, 800, 900, 1000, 1100, 1200, 1300, 1400, and 1500 described in conjunction with FIGS. 6-15 or portions thereof may be implemented by and/or executed on a single computer or device, such as client computer 200 of FIG. 2, network computer 300, authentication device 402, or the like. In other embodiments, these processes or portions of process thereof may be implemented by and/or executed on a plurality of network computers, such as network computer 300 of FIG. 3 or in a cloud/cloud service environment. Further, in at least one of the various embodiments, the processes described in conjunction with FIGS. 6-15 may be operative in authentication devices such as those described above and at least on authentication devices as described in conjunction with FIG. 4A, FIG. 4B, and FIG. 5.

Figure 6:
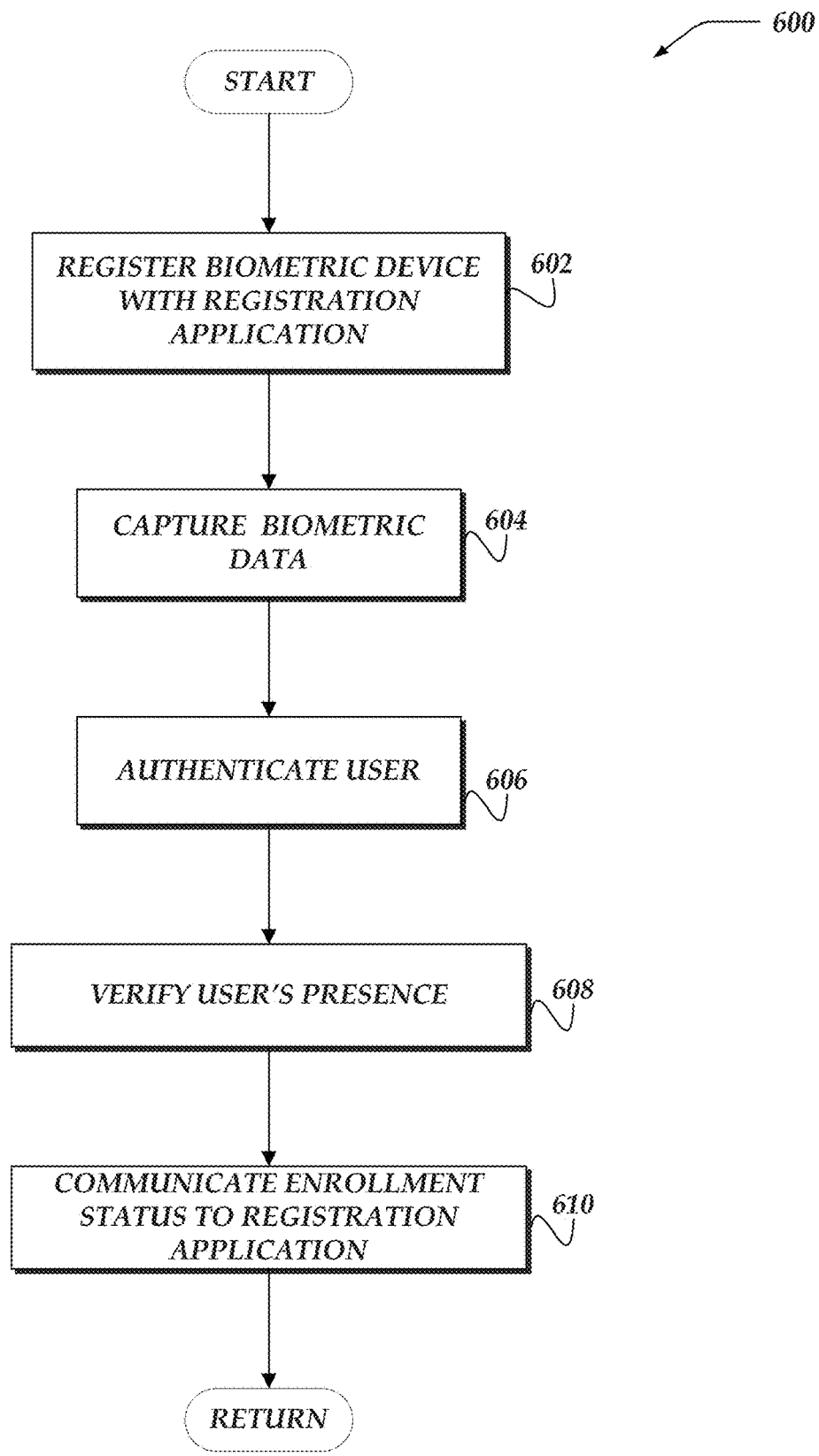
FIG. 6 is a flowchart for a process for enrolling an authentication device, such as a biometric device as contemplated in this example, in accordance with at least one of the various embodiments.

FIG. 6 shows an overview flowchart for process 600 for enrolling an authentication device in accordance with at least one of the various embodiments. In at least one of the various embodiments, enrolment or initialization of the user is performed when the user first uses the wearable authentication device. After a start block, at block 602, in at least one of the various embodiments, an authentication device may be paired or registered with a registration application.

At block 604, in at least one of the various embodiments, biometric signals used to generate a biometric profile are captured from the user. For example, primary biometric signals from a fingerprint scanner may be captured and stored. Additionally, physiological and/or secondary biometric signals, such as ECG signals, may be captured while the fingerprint is being captured. The ECG may then be analyzed, as discussed below with regard to FIG. 7, to validate that the captured fingerprint came from a genuine live user. In some embodiments, biometric signals may be stored by the system in respective user profiles on or more network-accessible computers or servers so to allow for execution of a network-mediated authentication process upon receipt of biometric data from a wearable authentication device. In other embodiments, biometric data may be stored exclusively on each given user authentication device so to invoke an onboard user authentication process.

At block 606, in at least one of the various embodiments, the authentication device may employ one or more biometric signals and/or biometric data to authenticate the user.

At block 608, in at least one of the various embodiments, the authentication device may perform one or more actions to verify the presence of a genuine user. In one or more of the various embodiments, the user's presence may be verified using one or more physiological and/or secondary biometric signals, such as an ECG, or other physiological sensors, to verify the presence of the user. In some examples, other user identification and/or authentication may also be captured and stored in the user's network and/or onboard profile.

At block 610, in at least one of the various embodiments, enrolment status may be communicated from the authentication device to the registration application. Next, control may be returned to a calling process.

In at least one of the various embodiments, additional authentication factors may be employed during enrollment for high security applications. An optional motion sensor in the wearable device may enable, for example, recognition of secret hand gestures. Passwords, PINs, voice commands or other deterministic user inputs may be used as additional authentication mechanisms. Once authenticated, the wearable device may be considered preauthorized and may stay in the preauthorized mode until it is separated from the user. In at least one of the various embodiments, the registration application that is performing the enrollment actions may be configured to collect one or more of the additional authentication factors.

Figure 7:
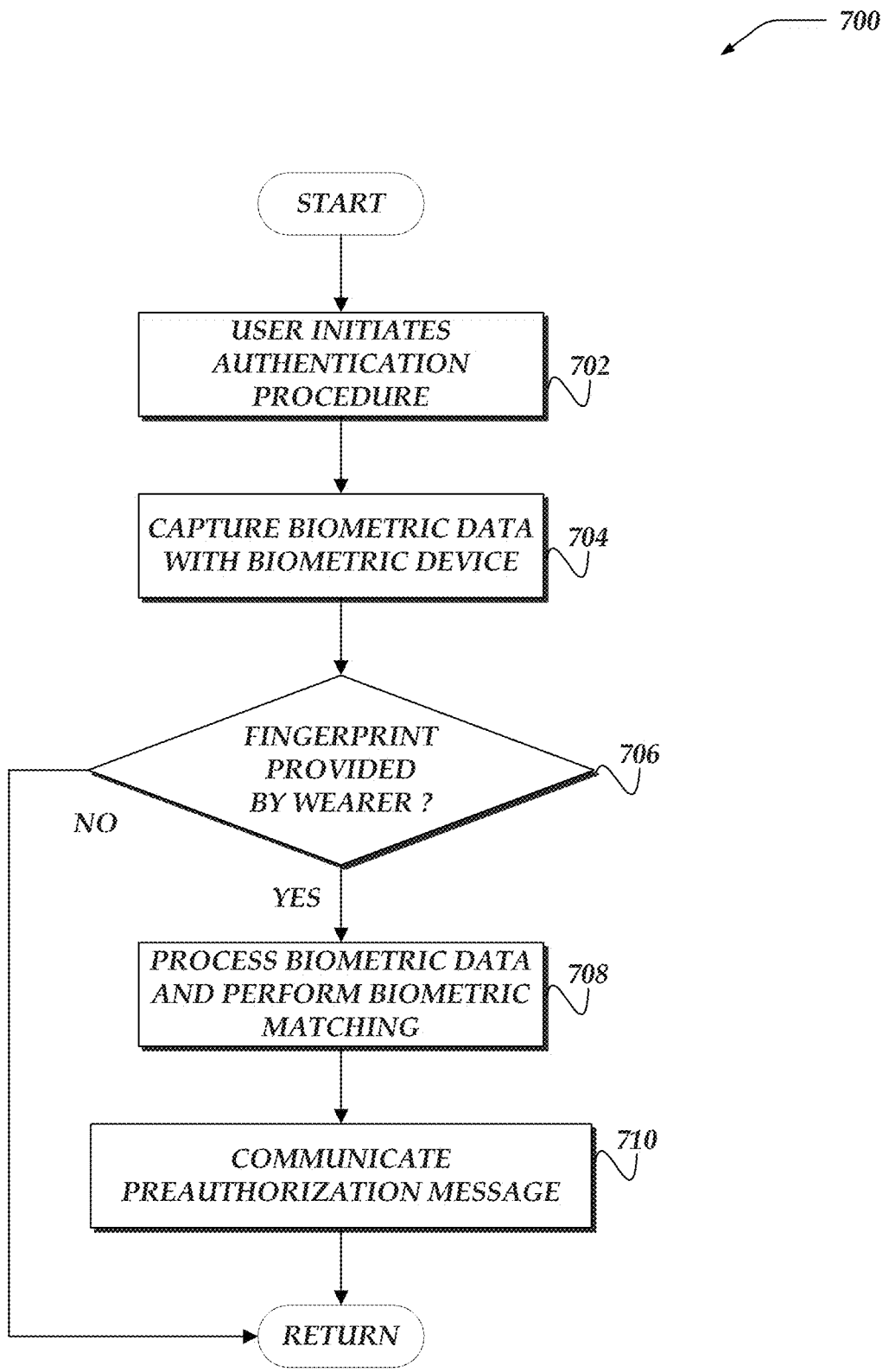
FIG. 7 is a flowchart for a biometric device authentication process to achieve device pre-authorization in a multimodal user access authorization process, in accordance with one embodiment.

FIG. 7 shows an overview flowchart for process 700 for multimodal authentication to confirm presence of a genuine user. After a start block, at block 702, in at least one of the various embodiments, a user may initiate a procedure for preauthorizing an authentication device.

At block 704, in at least one of the various embodiments, biometric data may be captured using the authentication device. A biometric signal of one or more biometric features of the user may be captured by the wearable device. In at least one of the various embodiments, a primary biometric feature is captured at the same time as a physiological signal is captured, where a same finger used to capture the primary biometric feature is used to capture the physiological feedback. However, as discussed above, different timings and orderings of biometric/physiological feature capture are similarly contemplated.

At decision block 706, in at least one of the various embodiments, the secondary physiological feature(s) are analyzed to determine if a finger from a genuine living human user was provided to the primary biometric scanner for capture. In one embodiment, while the fingerprint is being captured, an ECG is captured from the same location on the wearable authentication device and compared to one or more stored ECG profiles. If, within a given level of confidence, the ECG biometric feature is determined to match one or more of the stored ECG profiles, then because the fingerprint was captured in the same place and at the same time, the wearable authentication device (or a registration application) determines that a genuine living human provided the fingerprint, and process continues at block 708. However, if the ECG is determined to be attenuated, missing, or corrupted, such as if a hacker is attempting to use a mold of a lifted fingerprint, the process continues to the return block. As discussed above, the stored ECG profiles are not necessarily, or even often, a user-specific ECG profile stored in a user's biometric profile. Rather, stored ECG profiles may be generic, synthetic, and/or representative ECG profiles, as the ECG comparison may be used to determine liveness, not identity. Accordingly, a user-agnostic comparison may be invoked to satisfy a live authenticated user requirement based on a satisfaction that the biometric sensor (e.g. finger image-based sensor) is effectively collocated with a physiological live user sensor probe (e.g. ECG probe, and that a valid ECG signal can, generally, only be successfully acquired when the ECG circuit is completed by a same finger invoking the biometric sensor and another wearable contact location on the same user. In doing so, complex signal analysis procedures (e.g. spatio-temporal signal classifiers, etc.) typically required for full ECG biometry based on stored user-specific ECG waveforms, for example, can be avoided in favour of a computationally streamlined live user profile validity and confirmation procedure based on a generic (user-agnostic) profile.

Moreover, comparison with a generic (ECG) profile may take various forms and invoke various profile parameters, features or the like. For example, different degrees of accuracy and/or levels of confidence may be required depending on the application at hand, levels of security required, likelihood of fraud or collusion anticipated and/or other availability of other security or authentication means that may be provided concurrently with the herein described attributes. For example, in one particular example, a live user ECG signal acquired through the UAD may be compared with a stored generic ECG signal to identify certain similarities and/or distinctions such as, an expected signal amplitude (e.g. to identify unduly attenuated signals), a reasonable pulsatile signal frequency range, rate, completeness, peak to peak consistency, and/or shape (e.g. to distinguish signals truly captured from a same user between two opposed body contact points as intended, such as opposed hand/wrist contacts, from a signal captured between contact points from two distinct users or some unintended combination of user contacts/touch points), or like features and/or parameters.

Figure 19A:
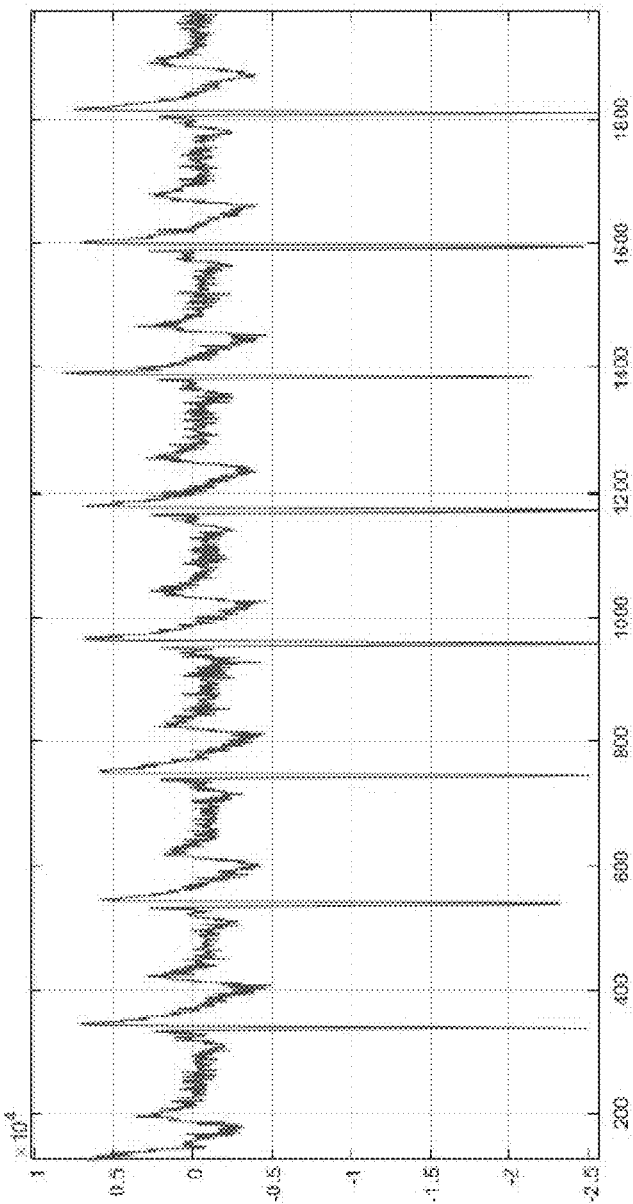
Figure 19B:
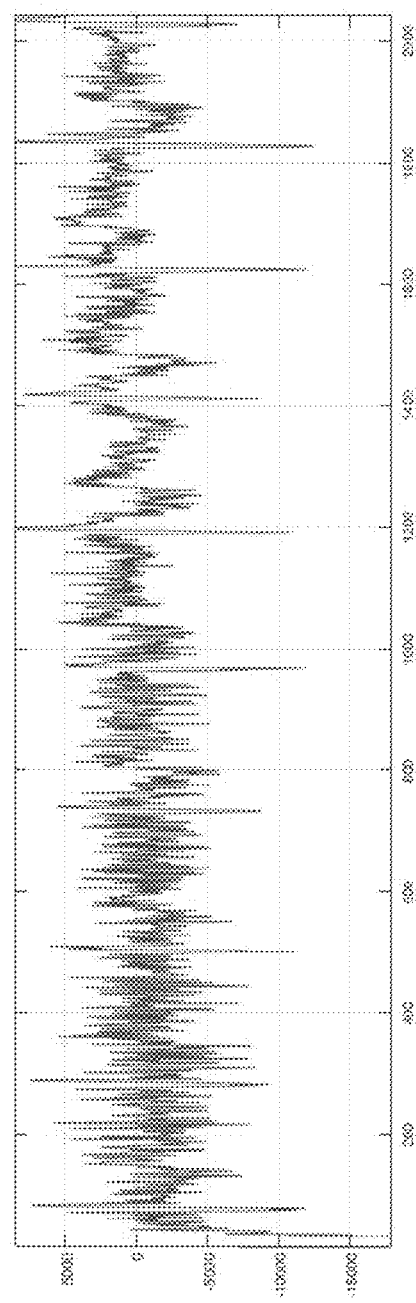
Figure 19C:
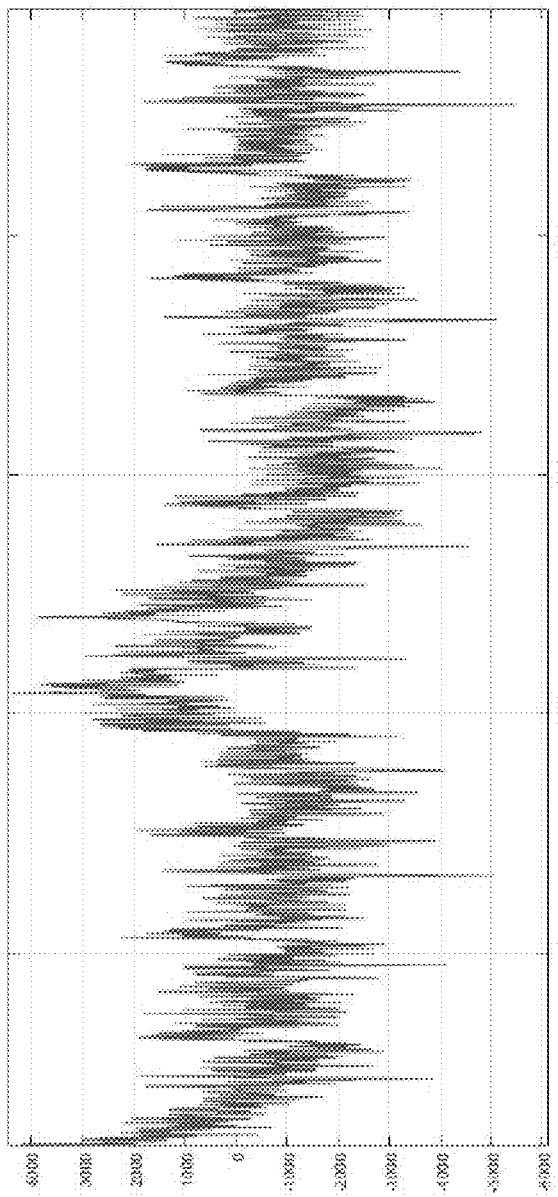
Figure 19D:
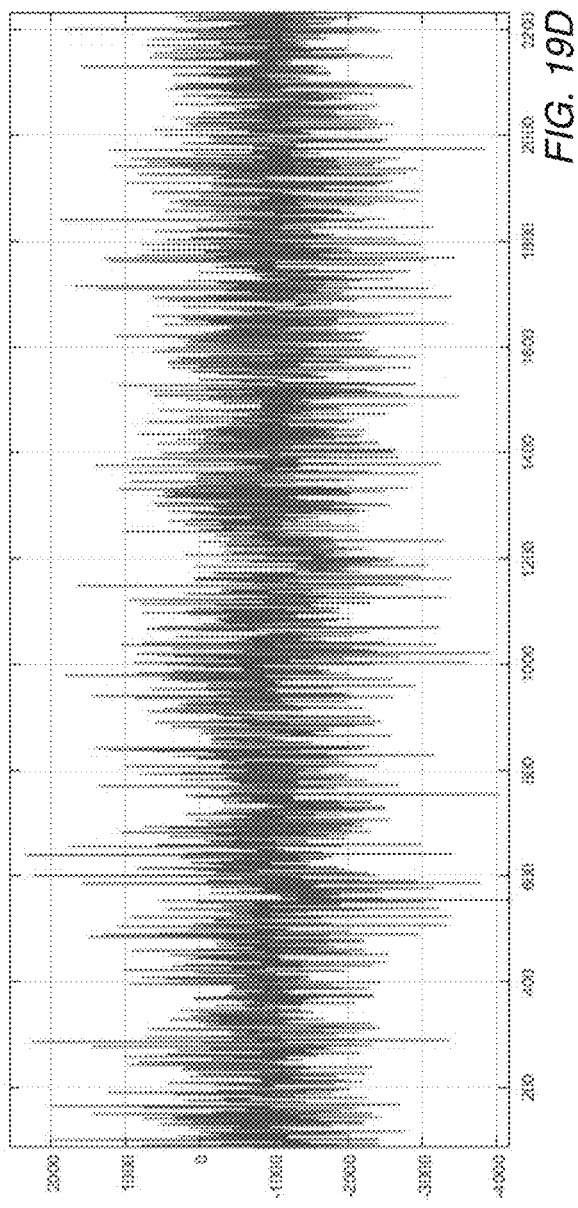
FIG. 19D is an illustrative ECG signal in which the probe pair is triggered by different users resulting in the acquisition of a non-compliant ECG signal, in accordance with one embodiment.

For example, and with reference to FIGS. 19A to 19C, different ECG signals acquired from a same user are illustrated in which the user completed an ECG acquisition circuit by interfacing with a first ECG finger probe (i.e. collocated with a fingerprint sensor) with a finger of one hand, and with a second ECG wrist probe with a wrist of the opposite hand. This particular configuration is similar to that proposed above within the context of a wearable wristband embodiment. In each of FIGS. 19A to 19C, a pulsatile waveform is observed, however, a general quality of this waveform is shown to decrease and thus become harder to recognize as a truly authentic ECG profile. This may be, for example, due to an increased misalignment or decreased contact quality of the user's finger and/or wrist as compared to what was intended by design. For example, when an authentication band is worn by an unauthorized user, an authorized user could still attempt to provide its fingerprint on a collocated fingerprint scanner while the unauthorized user awkwardly completes the ECG circuit through collocated finger and wrist contacts. Given this awkward arrangement, an ECG signal of lesser quality may be captured and thus fail to successfully compare to a generic profile. On the other hand, should the ECG signal rather result from contacts with different users (e.g. authorized user finger on collocated finger probe and unauthorized user wrist contact), a much noisier signal may be acquired, as shown for example at FIG. 19D.

Figure 20A:
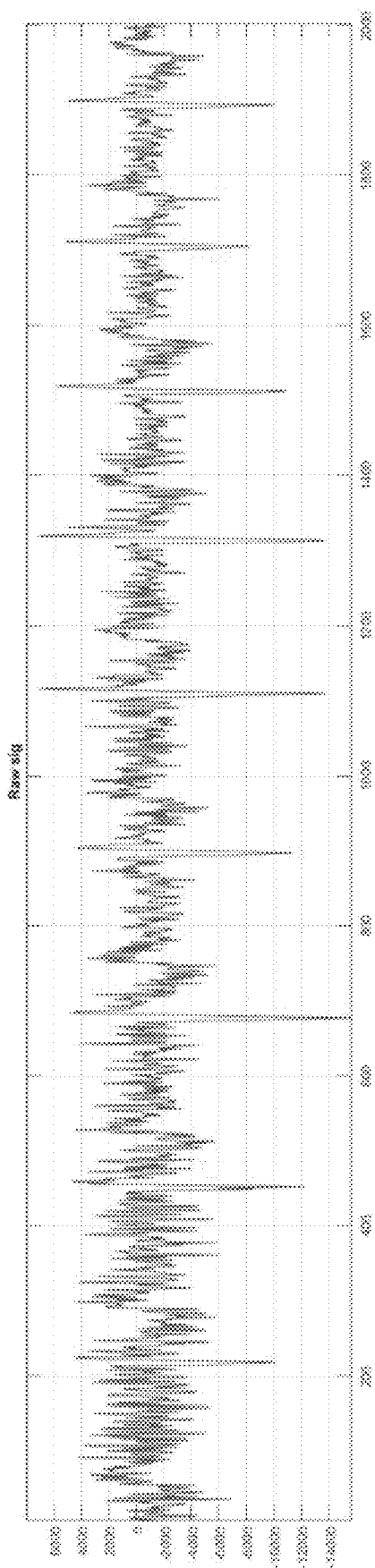
FIGS. 20A and 20B are illustrative live and generic ECG signals showing a high degree of agreement indicative of live user authentication compliance.
Figure 20B:
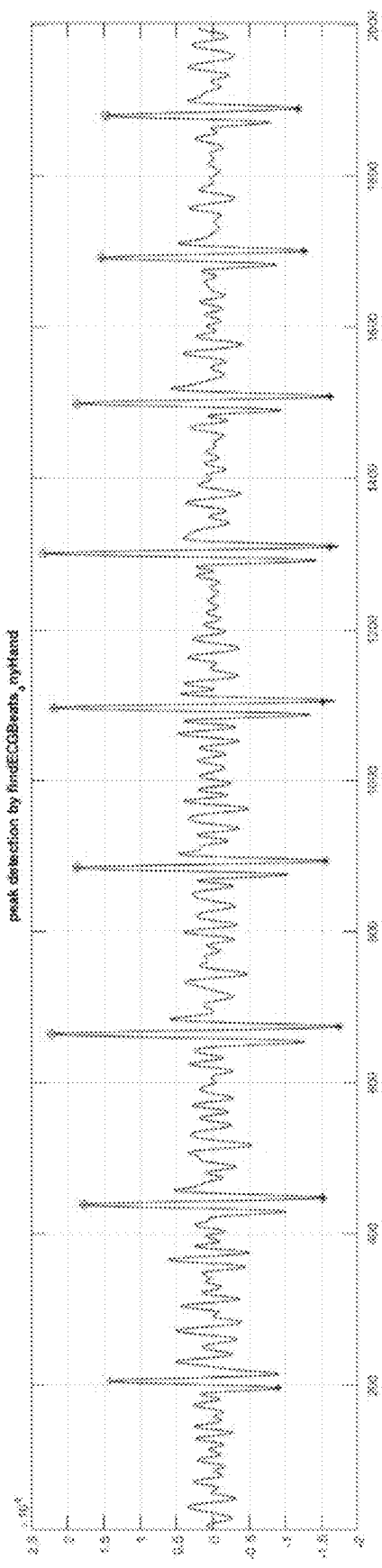
Figure 21A:
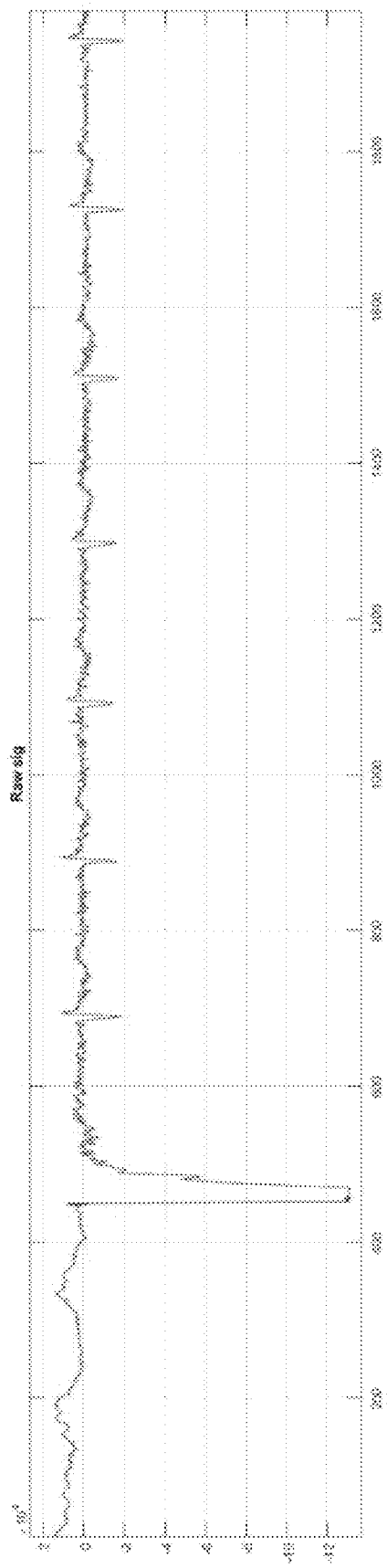
FIGS. 21A and 21B are illustrative live and generic ECG signals showing a sufficient degree of agreement to confirm likely live user authentication compliance.
Figure 21B:
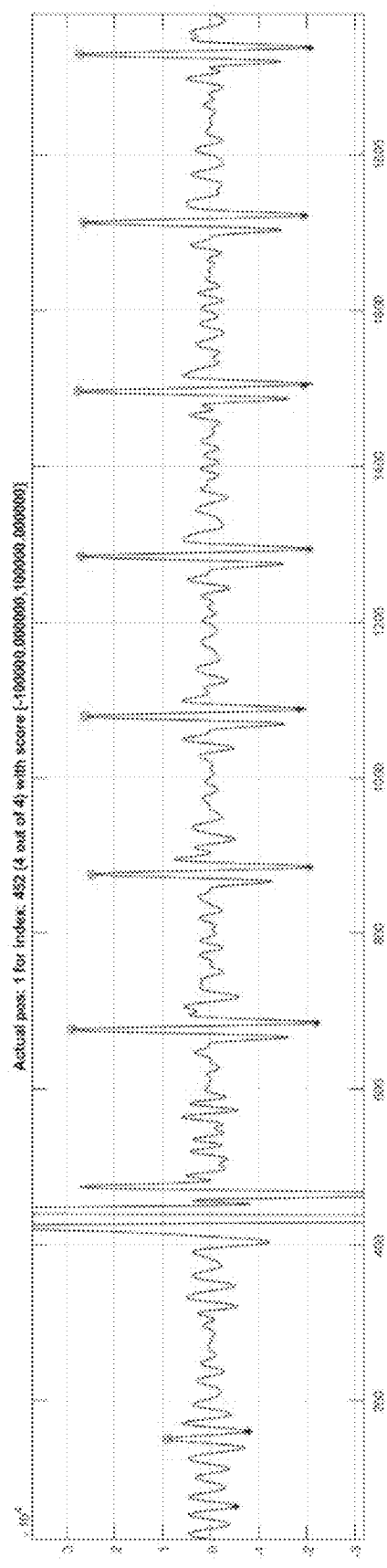
Figure 22A:
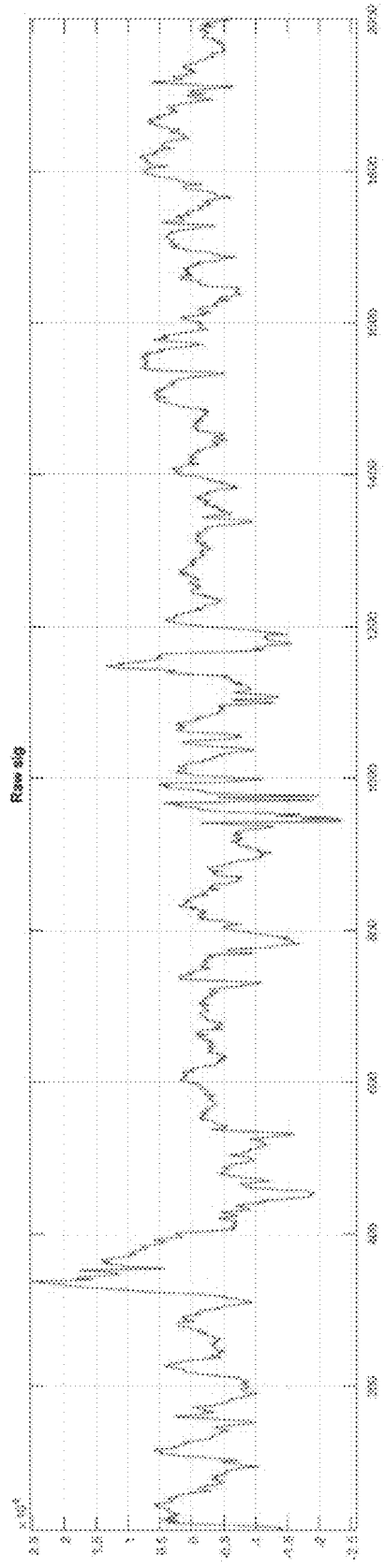
FIGS. 22A and 22B are illustrative live and generic ECG signals showing a low degree of agreement indicative of a lack of live user authentication compliance, in accordance with one embodiment.
Figure 22B:
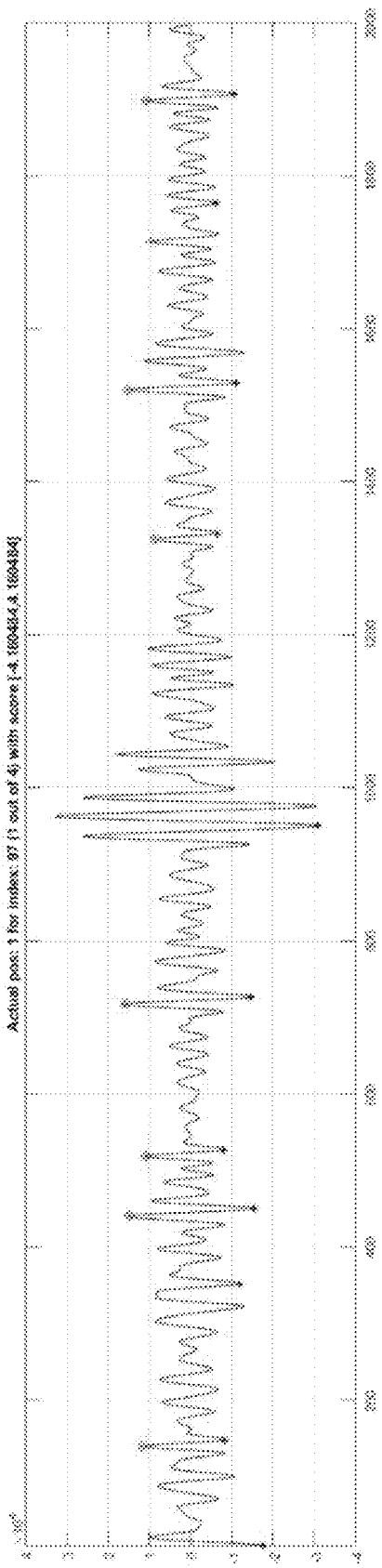

As noted above, in order to substantiate a certain level of confidence in comparing an acquired ECG or like physiological signal at authentication with a generic profile, different methods may be employed. In one particular example, the acquired ECG is compared with a generic profile to determine, within a designated degree of confidence, whether this signal corresponds with a well-characterized pulsatile waveform and/or frequency range. In FIGS. 20A and 20B, a sample ECG signal (FIG. 20A) is processed to detect peaks based on a stored ECG template, showing a good agreement and thus, indicating that the ECG signal was likely acquired in accordance with design specifications. In FIG. 21A, a somewhat less clear ECG signal is tested, in this case again showing sufficient agreement in FIG. 21B with a stored generic ECG template. In FIG. 22A, however, an ECG signal acquired in accordance with the prescribed authenticated user configuration nonetheless exhibits insufficient agreement with the template (FIG. 22B) resulting in the identification of aperiodic or inconsistent peaks. As a result, an ECG signal acquired during authentication as shown in FIGS. 20A and 21A would, depending on a prescribed level of confidence required by a given application, likely succeed in confirming an authenticated live user presence during authentication, whereas that shown in FIG. 22A would likely fail.

This approach may equally apply for embodiments in which distinct physiological sensors are used concurrently at authentication. For example, two or more ECG probes may be collocated with a fingerprint sensor so to form respective or a joint ECG contact(s) and/or circuits with one or more corresponding wrist probes. In doing so, where respective ECG circuits are formed to acquire respective ECG signals, then successful authentication will only result, in some embodiments, provided all ECG signal can satisfyingly compare with a stored generic profile. Similarly, distinct ECG probe pairs disposed at other locations around the wearable device may also require that each acquired ECG signal satisfy preset ECG signal requirements. For example, one or more additional finger/wrist ECG probe pairs can be provided along a wrist band to complement a pair collocated with the fingerprint scanner, for example, such as to have both a thumb/wrist ECG and finger/wrist ECG acquired upon the authorised user wearing the band and forming a C-shaped gesture around the band with their thumb and index to concurrently interface with each ECG probe pair and fingerprint scanner. Other one-handed gestures/configurations may also be contemplated, as can other non-wrist born embodiments considered without departing from the general scope and nature of the present disclosure. Interference or noise introduced by an authorized contact with any one or more of the ECG probes can, otherwise, in some embodiments, degrade a quality of the ECG signal and thus, potentially result in a failure to satisfy live user authentication requirements.

Accordingly, the physiological signal can be effectively analyzed, within a certain degree of confidence, to determine whether the finger from which the primary biometric feature was captured was the same finger from which the physiological signal was captured. In one such embodiment, as discussed above, when determining if a fingerprint came from a genuine living human user, ECG data from the physiological sensor is compared to one or more stored generic, synthetic, and/or representative ECG profiles. If the finger from which the primary biometric feature was captured was also used to capture an ECG (knowable because the biometric features are captured at the same time and from the same location on the wearable authentication device), and if the captured ECG matches one or more stored ECG profiles within a given confidence level, then the captured fingerprint was likely captured from the wearer of the authentication device, and the control flows to block 708. Otherwise, control flows to a return block to return control to a calling process.

At block 708, in at least one of the various embodiments, the primary biometric data may be processed and compared with one or more biometric profiles for correlating the biometric data to a user. In at least one of the various embodiments, to preauthorize the wearable authentication device subsequent to initialization, primary biometric data is received from the wearable authentication device and is authenticated on the authentication device or in some embodiments on the registration application. In either case, the primary biometric data may be authenticated based on a biometric profile that may be stored on the authentication device or in some embodiments, on the registration application. In at least one of the various embodiments, the primary biometric signal obtained is then compared to the previously obtained biometric profile to perform a biometric matching. In at least one of the various embodiments, the secondary biometric feature is also used to confirm the identity of the wearer.

At block 710, in at least one of the various embodiments, the authentication status, based in part on the result of matching the primary biometric signal, may be communicated from the registration application to the authentication device. Alternatively, in at least one of the various embodiments, an authorization key may be generated on the authentication device and communicated to the registration application. In at least one of the various embodiments, the authorization key may be used by the registration application to decrypt user profile information that may correlate the user with the authentication device. Accordingly, in some embodiments, the registration application may authenticate the user without directly receiving biometric signals or biometric data.

Accordingly, in at least one of the various embodiments, if the primary biometric signal matches the user's biometric profile, the authentication device may be set into a pre-authorized state. In at least one of the various embodiments, the registration application may communicate a control signal to the authentication device signalling that authentication device should enter the pre-authorized state. Or, in at least one of the various embodiments, the authorization key provided by the authentication device may enable the registration application to decrypt the biometric profile of the user enabling the registration application to preauthorize the authentication device.

In at least one of the various embodiments, at this point the authentication device is authenticated as being worn by the user that corresponds to the matched biometric profile and is preauthorized for enabling access to one or more access points. Next, control may be returned to a calling process.

In at least one of the various embodiments, once successful authentication is achieved, the application on the registration application communicates back to the wearable device and preauthorizes it for the user. The authentication device remains in a preauthorized state until it is removed from the user or separated from the user.

In some embodiments, the preauthorization of the wearable authentication device may be performed twice per day, once per day, or even less frequently, such as every two days, every three days, every four days, every five days, every six days, or once per week.

Also, in at least one of the various embodiments, once the authentication device is preauthorized, the registration application does not need to be within wireless range of the wearable authentication device to enable the user to transmit a control signal to an access point in order to obtain access to a physical or logical access point. Further interaction between the wearable and the registration application is not required to obtain access to access points.

In at least one of the various embodiments, the wearable authentication device may further be trusted to remain associated with the same person during later transactions by detecting device removal from the user. In this way, the wearable device is able to transmit an authenticated control signal that serves as a proxy for user identity authentication. In essence, the wearable authentication device becomes a trusted arbiter or proxy of identity for every other device, access point and system that the user interacts with. Although the wearable authentication device is able to transmit a biometric signal as the control signal at an access point, the biometric preauthorization of the wearable device via the registration application enables the control signal to be other than a biometric signal.

Figure 8:
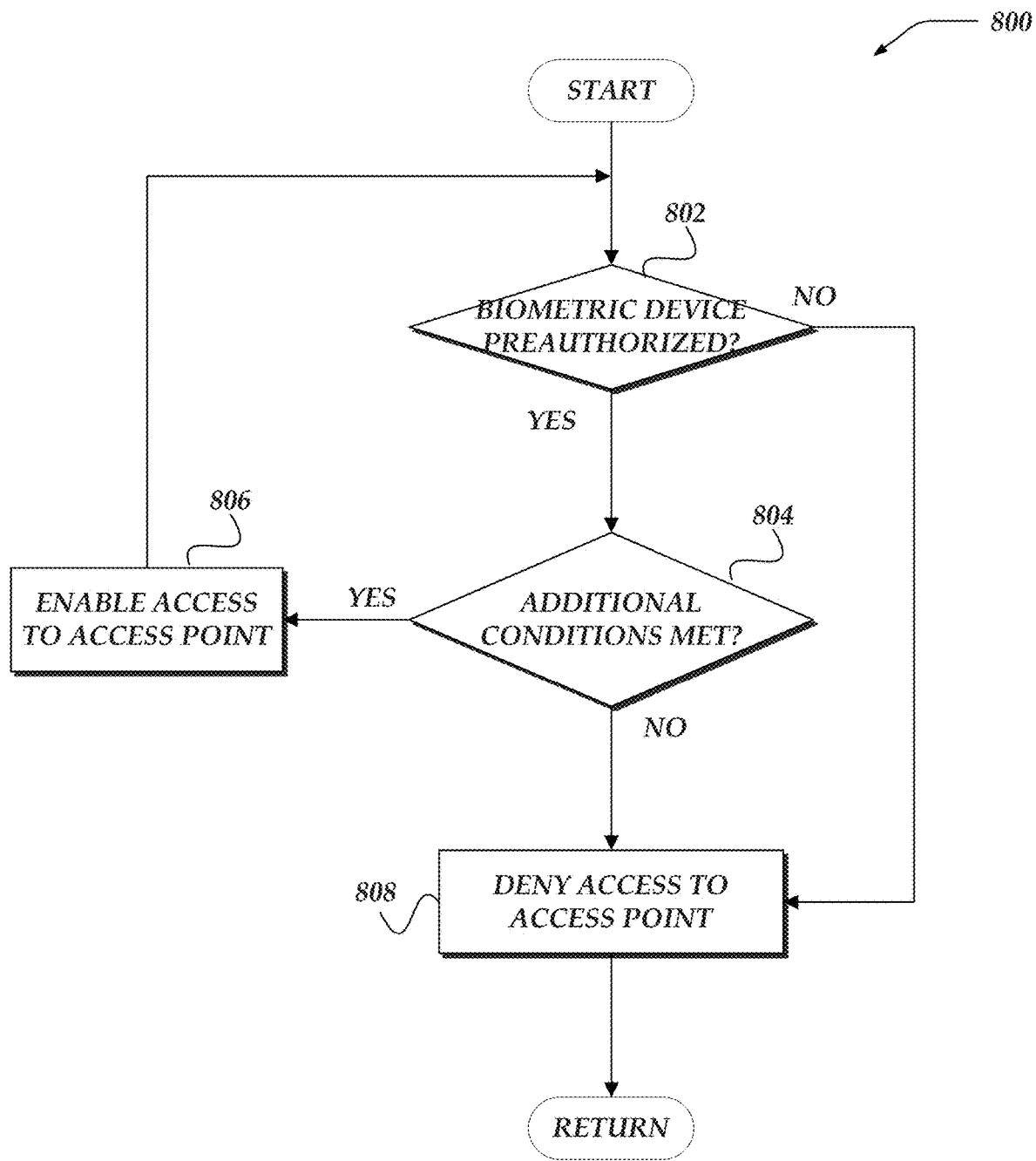
FIG. 8 is a flowchart for a process for authenticating a user with one or more access points in accordance with at least one of the various embodiments.

FIG. 8 shows an overview flowchart for process 800 for authenticating a user with one or more access points in accordance with at least one of the various embodiments. After a start block, at decision block 802, in at least one of the various embodiments, if a preauthorized authentication device in range of an access point, control may flow to block 804; otherwise control may flow to block 808.

At decision block 804, in at least one of the various embodiments, if one or more additional conditions (if any) are met, control may flow to block 806; otherwise control may flow to block 808. As discuss below, the authentication device, or the access point may be configured to require additional information before enabling access to the access point. In at least one of the various embodiments, additional security factors may be required to increase security, such as requiring one or more additional biometric features to authenticate the user, or requiring a password to be entered into the registration application. Such a password may be alphanumeric, or may be gestural or postural (finger tapping/swiping), captured by the wearable authentication device by the one or more sensors on the wearable device. Such additional security factors may be added to systems with high security requirements.

Also, in at least one of the various embodiments, additional conditions may be required based on information included in the user's profile. For example, the user profile may be configured to limit access to certain times of day or a certain number of times per day, and so on. See, FIG. 14 for a more detailed explanation of user profiles and their configuration.

Further, in at least one of the various embodiments, additional conditions may be required based on information included in the access point's profile. For example, the access profile may be configured to limit the number of preauthorized users that may obtain access to the access point each day, and so on. See, FIG. 15 for a more detailed explanation of access profiles and their configuration. Further, in at least one of the various embodiments, a condition may be membership of the user into one or more associations or groups, such as, employees, customers, VIP's, security, or the like, or combination thereof.

Also, in at least one of the various embodiments, the authentication device may include keys or other identifiers that may be associated with one or more groups or associations that may have issued the authentication device to the user. Accordingly, to meet the access conditions the authentication device may need to be authenticated and preauthorized as well as including the additional information indicating the authentication device associated with the correct group.

Moreover, in at least one of the various embodiments, an additional condition may be the requirement for one or more particular users to be sensed and authorized by the access point in addition the users attempting to obtain access. For example, one or more access points may be disabled from allowing any user access unless an authenticated supervisor user is sensed by the access point. In this example, an access point profile may be configured to disable other users unless a supervisor user is simultaneously sensed by the access point. Or, in at least one of the various embodiments, an access point may be configured to always require a certain number of authenticated users (e.g., 2, 3, 5) to be present and preauthorized before allowing any user to obtain access. For example, an access point configured to require two users to be present may be incorporated into an industrial machine that requires two authenticated operators for safety and/or security reasons.

At block 806, in at least one of the various embodiments, access to one or more access points may be enabled for the user that has the authentication device. Next, control may loop back to decision block 802. At block 808, in at least one of the various embodiments, access to one or more access points may be disabled. Next, control may be returned to a calling process.

In at least one of the various embodiments, user access to physical and logical access points may be controlled by a transmission of a control signal from the wearable authentication device to the access point. For example, in at least one of the various embodiments, one method of gaining entry at an access point may be to determine whether a wearable authentication device has been preauthorized and if that wearable authentication device is within an allowable range of the access point. If the answer is affirmative for both authorization and range to access point, the wearable authentication device may be arranged to transmit a control signal to the access point that affirmatively confirms that the authentication device is preauthorized. Accordingly, the user may obtain access to the access point. Further, authorization for access to an access point may be enabled by the wearable device at multiple access points subsequent to a single authorization by the registration application.

For example, in at least one of the various embodiments, user may access various access points through the course of a day with a single biometric authentication/preauthorization, such as, security doors at home, security doors at work, point-of-sale devices (e.g., to purchase coffee), wireless password entry to a personal electronic devices, gym or change-room security doors, transit payments, or the like. Accordingly, multiple secure transactions which traditionally have each required a unique security card or proof of identity may each be accessed using the same preauthorized authentication device employing a control signal affirmatively confirming that the authentication device is preauthorized.

In at least one of the various embodiments, if the wearable authentication device is in an authenticated mode, it may communicate this status information by wirelessly transmitting the control signals to devices and systems, such as, access points, that may be in the user's environment. Therefore, the presence of the user with the preauthorized authentication device within the range of a smart-connected access point device may be sufficient for unlocking and/or enabling access to the device. One method of determining proximity to access points is via measuring Bluetooth energy levels.

In at least one of the various embodiments, a preauthorized wearable authentication device may then be used to access/unlock the wearer's smartphone, tablet, online accounts, vehicle, and physical spaces, as well as provide personalization for smart environments, and allow third parties to detect their presence (e.g., office, club, retail environments, or the like).

In one or more of the various embodiments, since a preauthorized wearable authentication device remains authorized while a confirmed genuine user is wearing the biometric device, one or more actions on one or more access points or access terminals may be associated with the confirmed genuine user without the need of an additional or subsequent explicit action for authentication.

In at least one of the various embodiments, another example of a logical access point is a paired device. For example, if a wearable authentication device has been preauthorized, other paired devices such as smartphones, computer terminals, tablets, laptops, environmental control systems which do not have the capability to authorize the wearable authentication device, but which would be otherwise locked, may be accessed via a control signal transmitted by the preauthorized wearable authentication device.

In at least one of the various embodiments, transmission of entry authorization signals from the preauthorized wearable authentication device to the desired access point by way of the control signal is preferably accomplished wirelessly. Some non-limiting examples of wireless technologies that may be used are Bluetooth, WIFI, NFC, or the like. In some embodiments, a wearable authentication device may be arranged to include more than one type of transmitter or transmitting means to accommodate the range of receivers that may be used at various access points. Additionally, in some embodiments, the wearable authentication device may be arranged to include more than one type of receiver or receiving technology. In this way, access points already in place may be accessed by incorporating the corresponding communication technology into the wearable authentication device.

In at least one of the various embodiments, if a person is wearing a preauthorized wearable authentication device, they may subsequently access devices and accounts in their environment that are configured as access point (e.g., they include access point applications for controlling access). In the preferred embodiment a device or system acts as an access point that grants access to the user when the preauthorized wearable authentication device is detected to be in close proximity and when an authenticating control signal is received. In addition, access control may be further conditioned by requiring one or more of a determination of proximity/range of the wearable authentication device to the access point, the detection of a gestural input by the wearable authentication device, and additional skin or body contact detection by the wearable authentication device such as with a finger (tapping), password, PIN's voice commands, or the like, or combination thereof.

In a different embodiment a user may indicate an intent to access an access point using gesture control. Accordingly, in at least one of the various embodiments, the authentication device may be arranged for collecting, processing and matching motion or gestural signals to pre-defined or user-defined gestures. In one example, if an "unlock" gesture is performed by the user and detected by the authenticated wearable authentication device, an "access" control signal may be transmitted to the device or system comprising the access point that the user intends to access.

In at least one of the various embodiments, a user may indicate intent to access a device or system comprising an access point by touching or tapping the wearable authentication device with a body part, and/or making skin contact with the device. For example, to access a smartphone, the wearable authentication device may transmit a control signal to the smartphone indicating that the wearable authentication device is preauthorized, and is also within proximity to the device or system to be unlocked or accessed. Following that, the smartphone may be unlocked when user double taps the authentication device.

In another example, user intent with skin contact may be detected with a signal that is transmitted from the wearable authentication device to the access point that the user desires access through the human body. In at least one of the various embodiments, the wearable authentication device may be arranged to include a transmitter of a unique sequence and the accessing device is equipped with a receiver. Capacitive or galvanic coupling may be employed for the transmission of the signal through the body.

Figure 9:
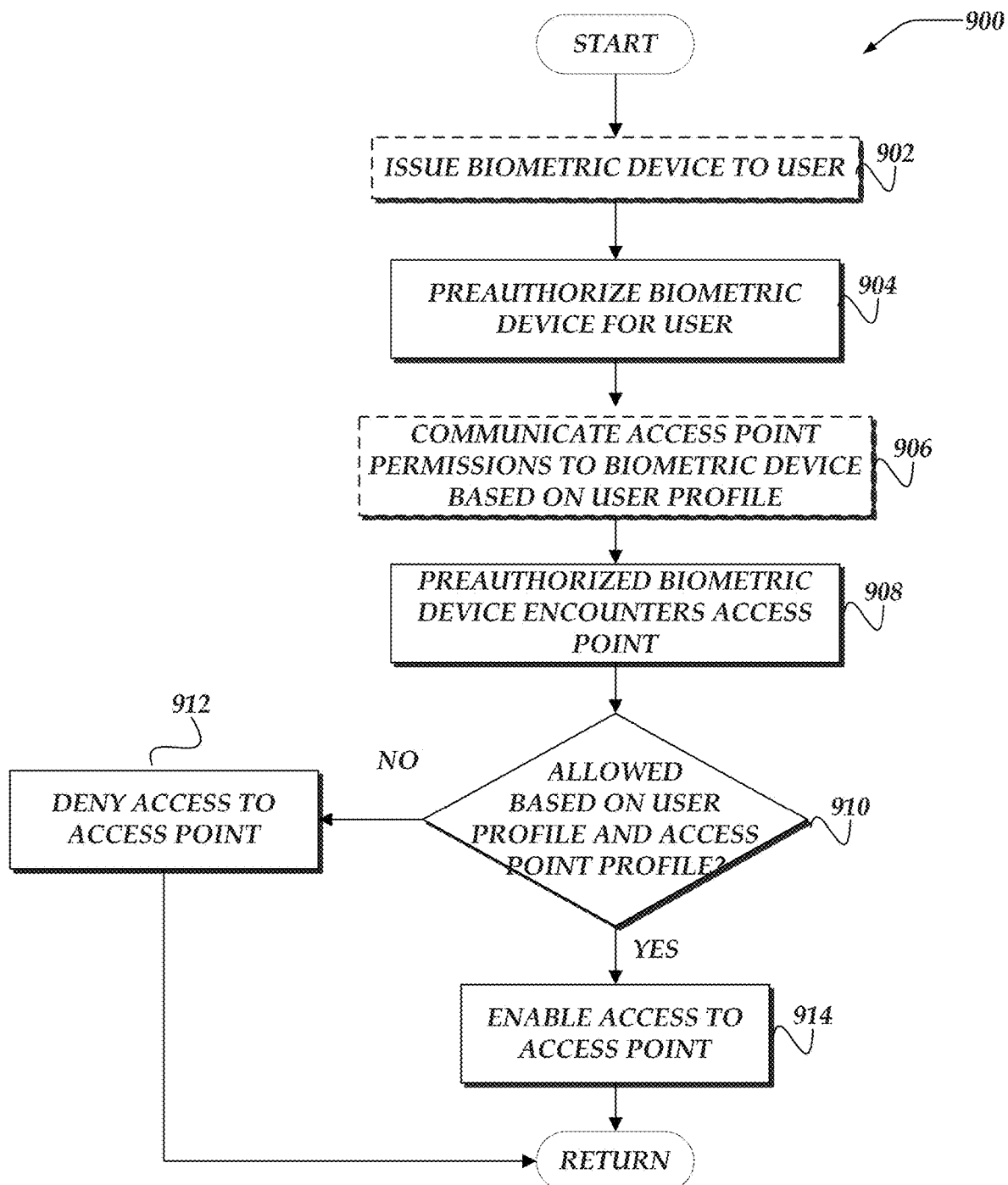
FIG. 9 is a flowchart for a process for authenticating a user with one or more access points in accordance with at least one of the various embodiments.

FIG. 9 shows an overview flowchart for process 900 for authenticating a user with one or more access points in accordance with at least one of the various embodiments. After a start block, at block 902, in at least one of the various embodiments, optionally, a authentication device may be issued to a user. In at least one of the various embodiments, an organization, such as, an employer, school, entertainment provide, amusement park, or the like, may provide authentication devices to users that may be associated with the organization. In other cases, a user may have their own authentication device.

At block 904, in at least one of the various embodiments, a authentication device may be authenticated for a particular user. Also, in at least one of the various embodiments, as discussed above, a authentication device may be enrolled and preauthorized for a user.

At block 906, in at least one of the various embodiments, access point permission information may be communicated to the authentication device based on the user's profile. In at least one of the various embodiments, during the authorization of the authentication device the registration application may be arranged to retrieve information about which access points the user may be enabled to access. In at least one of the various embodiments, the information may be in the form of a list of restricted access points, or it may be a list of accessible access points, or a combination thereof.

In at least one of the various embodiments, the permission information may be configured and stored on a authentication server, a registration application, or the like. In at least one of the various embodiments, permissions may be assigned or allocated on a per user basis, or based on user groups, user roles, or other user properties. In at least one of the various embodiments, the permissions may be included as part of a biometric profile for a user.

In at least one of the various embodiments, the permission information may enable an administrator to configure which users may be enabled to access certain access points. See, FIGS. 13-15. Importantly, in at least one of the various embodiments, the permissions may be managed outside of the access point. Accordingly, in at least one of the various embodiments, the access point may be relieved of any responsibility to manage if an authorized/identified user actually has permission to access a particular access point.

At block 908, in at least one of the various embodiments, the authenticated authentication device encounters an access point. In at least one of the various embodiments, the authentication device and the access point may recognize each other's presence. For example, in at least one of the various embodiments, a wireless protocol such as Bluetooth's advertising protocol may be employed to enable the authentication device and the access point to identify each other.

In at least one of the various embodiments, the authentication device and the access point may begin a handshaking protocol (e.g., exchanging control signals) for determining if the authentication device is authenticated with its wearer and preauthorized.

At decision block 910, in at least one of the various embodiments, if access to the access point is allowed based on the user profile and the access point profile, control may flow to block 914; otherwise, control may flow to block 912. In at least one of the various embodiments, before the authentication device communicates its authentication status to the access point, the permission information onboard the authentication device may be checked to determine if the user wearing the authentication device should be enabled to access the access point. In at least one of the various embodiments, the authentication device and/or the access point may employ the user's profile or the access point's profile (if any) for determining if the authenticated and preauthorized user can obtain access to the access point.

In at least one of the various embodiments, the user profile information, or a portion of it, may be located on the authentication device, or stored on a authentication server accessible over a network. Likewise, in at least one of the various embodiments, the access point profile information, or a portion of it, may be located on the access point, or stored on a authentication server accessible over a network. In at least one of the various embodiments, user profile information and/or access point profile information may be accessible from a cloud based service.

In at least one of the various embodiments, the authenticated authentication device authenticates the identity of the user that is wearing the device, but it may also indicate if that particular user is allowed access to the access point.

In at least one of the various embodiments, the access point may maintain permission information regarding the authenticated users that may be enabled access. However, for some access points, especially those designed to be low powered and/or without network connectivity, they may not have facilities sufficient for determining if a user, even though authenticated by the wearable biometric, is authorized to access the access point.

For example, in at least one of the various embodiments, each member of a family comprising adult and children may use wearable authentication device. The authentication devices may authenticate the identification each member of the family, adult and child alike. However, in this example, it may be important to restrict the children from accessing particular access points. For example, an access point like an automobile door or an automobile ignition may be restricted to just the authenticated adults.

Accordingly, rather than requiring the automobile access points to maintain an access control list that distinguishes among family members, the authentication device for the children may maintain the permission information. This permission information may be updated for an individual each time a user authenticates with given authentication device. Returning to the last example, if a child obtains his or her driver's license the parents may update the child's permission information, enabling them to use their authentication device to enable access the automobile. Note, this may be accomplished without directly updating the automobile access point.

At block 912, in at least one of the various embodiments, since the access point is not accessible to the user, access to the access point may be denied for the user. Next, control may flow to a return block to return control to a calling process. During the handshaking between the authentication device and the access point, the authentication device rejects the access point control signals, or it may be arranged to refrain from sending an "authenticated" status to the access point. At block 914, in at least one of the various embodiments, since access to the access point is permitted, or otherwise not barred for the user, access to the access point may be enabled. Next, control may be returned to a calling process.

Figure 10:
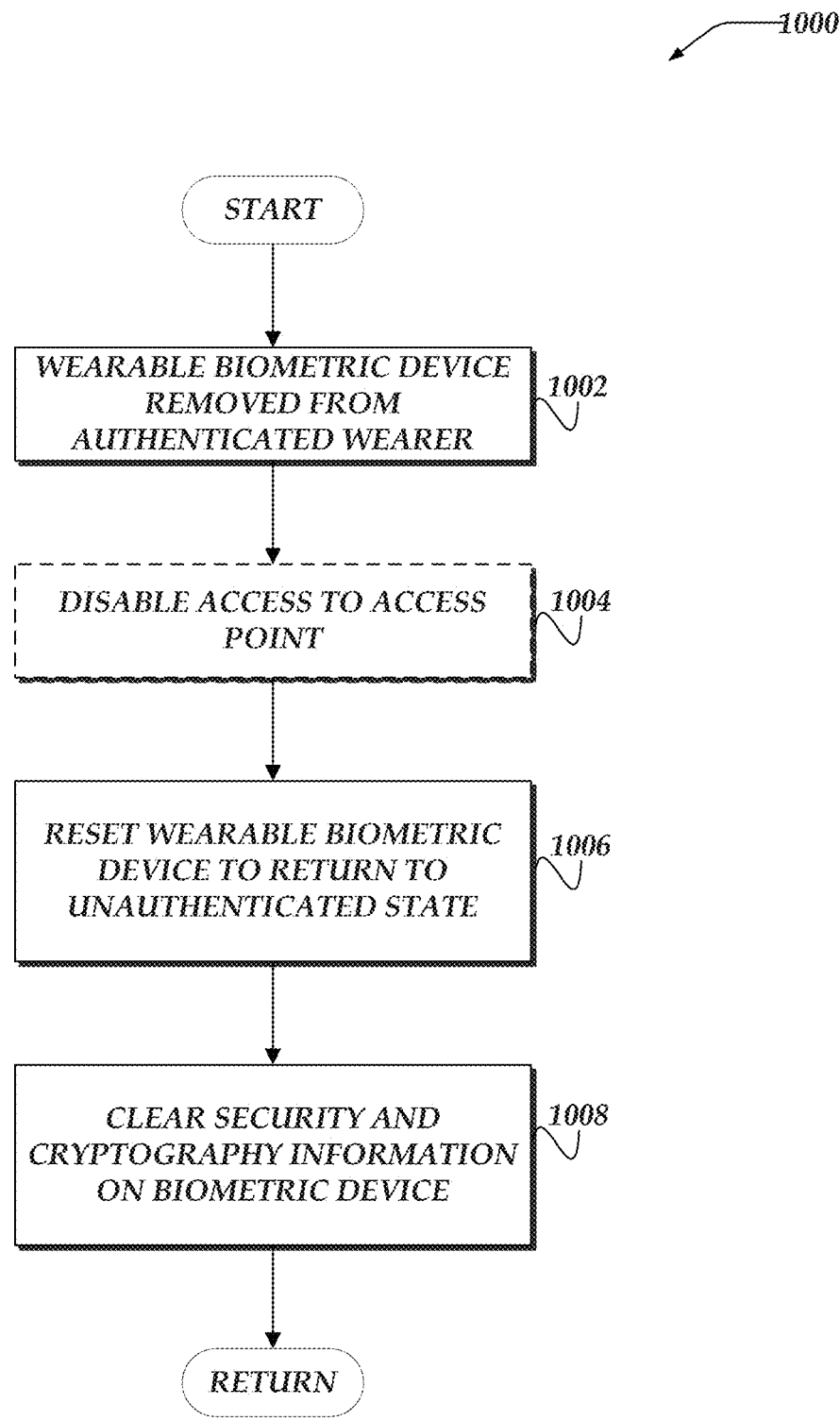
FIG. 10 is a flowchart for a process for de-authenticating a biometric device when it is removed from a wearer in accordance with at least one of the various embodiments.

FIG. 10 shows an overview flowchart for process 1000 de-authenticating a authentication device when it is removed from a wearer in accordance with at least one of the various embodiments. After a start block, at block 1002, in at least one of the various embodiments, a wearable authentication device is removed from an authenticated wearer. In at least one of the various embodiments, the authentication device may detect that has been removed, or is about to be removed (e.g., clasp opening) from the authenticated user as described above. Also, in at least one of the various embodiments, the authentication device may include a lanyard attached by a clasp such that removing the lanyard from the authentication device resets (deauthorizes/deauthenticates) the authentication device. As noted above, break of contact with an onboard physiological sensor may also trigger user authentication/authorization to be revoked.

In at least one of the various embodiments, the authentication device may remain preauthorized and authenticated as long it remains within a defined range/proximity of the user. Additional sensors or radios on the user's person may be employed to determine if the authentication device is within an allowed range of user. For example, a user may preauthorize a handheld tool or device using biometric features. Then as long as the preauthorized device remains within a range defined range of the user it will remain preauthorized—enabling the tool to be used by the user.

At block 1004, in at least one of the various embodiments, optionally, access to one or more access points may be disabled. In at least one of the various embodiments, if the authentication device is being employed to enable the user to access an access point, the access point may be configured to automatically disable access to the access point. In at least one of the various embodiments, in some cases, such as, an operating automobile, the access point may be configured to continue operating until it is safe to disable operation. In other cases, such as, accessing a secure terminal the access point may immediately disable access for the current user. In at least one of the various embodiments, other configuration may include starting a countdown timer before disabling access. Also, the access point may be configured to generate a log entry and/or generate a notification upon removal of the authentication device. Note, in at least one of the various embodiments, this block may be considered optional because the user may not be accessing an access point when the authentication device is removed.

At block 1006, in at least one of the various embodiments, the wearable authentication device may be reset and set to an unauthenticated state. In at least one of the various embodiments, as discussed above, resetting the authentication device will require a user to authenticate the authentication device again by providing biometric information to the registration application, satisfying, via a secondary biometric feature, that the wearable authentication device is worn by the user providing the primary biometric feature, and matching the biometric profile that corresponds to the user before the authentication device is returned to an authenticated state. At block 1008, in at least one of the various embodiments, further to resetting the wearable authentication device, security and cryptographic information related to the operation and/or authentication of the authentication device may be cleared or otherwise erased from the authentication device. Next, control may be returned to a calling process.

Figure 11:
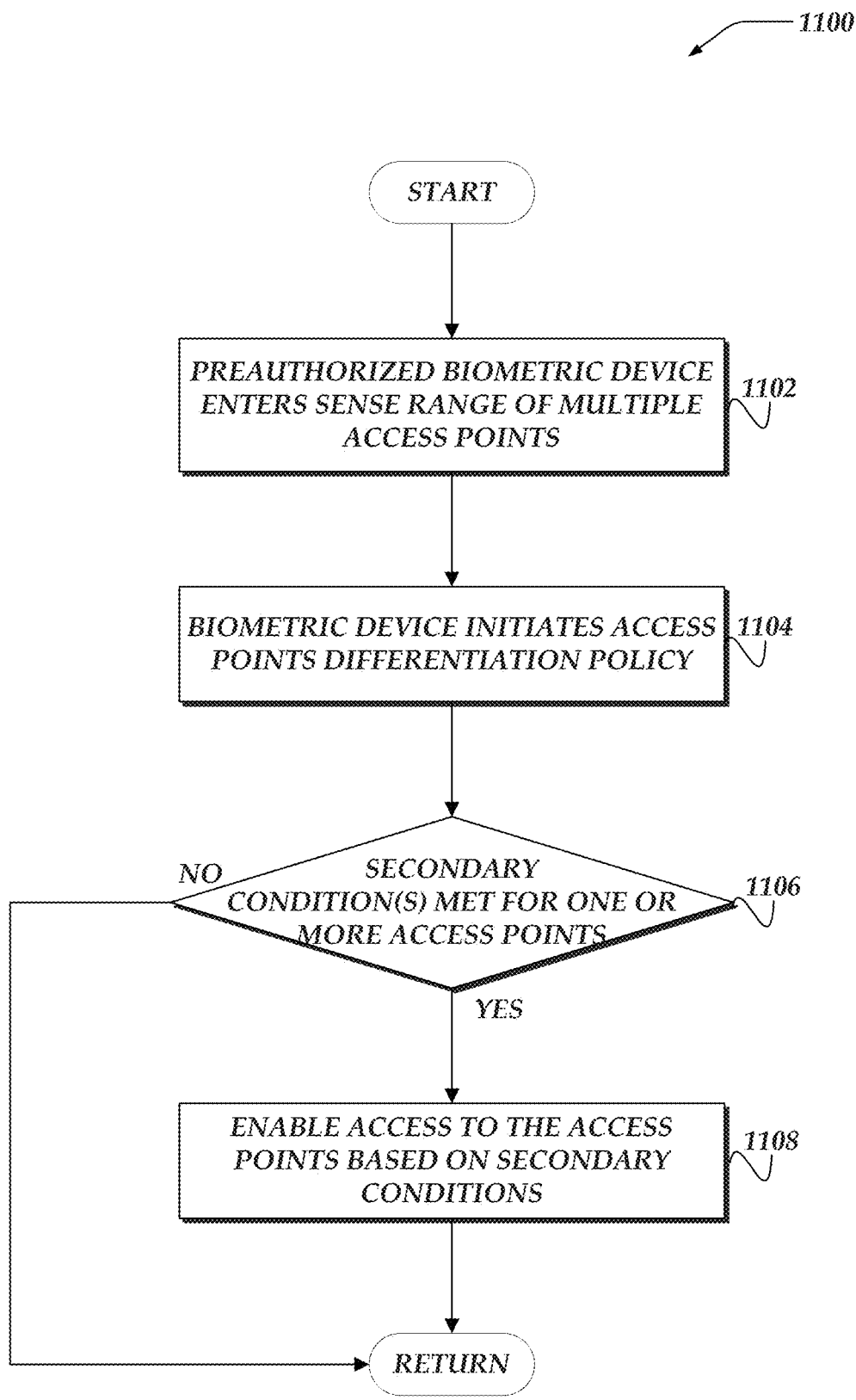
FIG. 11 is a flowchart for a process that manages if a biometric device encounters multiple access points in accordance with at least one of the various embodiments.

FIG. 11 shows an overview flowchart for process 1100 that manages if a authentication device encounters multiple access points in accordance with at least one of the various embodiments. After a start block, at block 1102, in at least one of the various embodiments, an authenticated authentication device enters the sensing range of multiple access points. In at least one of the various embodiments, a user wearing an authenticated authentication device may walk into a room with several access points that he or she may be enabled to access. For example, in at least one of the various embodiments, a supervisor that enters a room with several access points may not want multiple access points in range of the wearable authentication device to enable access at the same time.

At block 1104, in at least one of the various embodiments, the authentication device initiates one or more access differentiation policies. In at least one of the various embodiments, since the authentication device has sensed multiple access points at the same time it may be configured to execute one or more differentiation policies.

In at least one of the various embodiments, differentiation policies may be configured to have different rules for different classifications of access points. In some embodiments, for some types of access points, it may be unnecessary to distinguish between them. For example, if the multiple access points correspond to room light switches it may be harmless and/or desirable to turn all the switches on when a user wearing an authenticated authentication device enters a room. However, in other cases, such as, computer terminals it may be undesirable to unlock and enable access to each detected terminal at the same time.

Accordingly, in at least one of the various embodiments, the differentiation policy may include rules and filters that may be associated with the various access point that may be encountered. In at least one of the various embodiments, the differentiation policies may be established one or more secondary conditions that must be met to differentiate among certain multiple access points.

In at least one of the various embodiments, secondary conditions may be similar to those described above, such as, requiring PINs, passwords, proximity requirements, gestures, or the like, with respect to the particular access point the user wants to access.

At decision block 1106, in at least one of the various embodiments, if one or more secondary conditions are met for differentiating among access points, control may flow to block 1108; otherwise, control may flow to a return block. In at least one of the various embodiments, if the secondary conditions are not met, access to those access points requiring the secondary conditions may remain disabled. At block 1108, in at least one of the various embodiments, access to one or more access points may be enabled based on the secondary conditions that may have been met. Next, control may be returned to a calling process.

Figure 12:
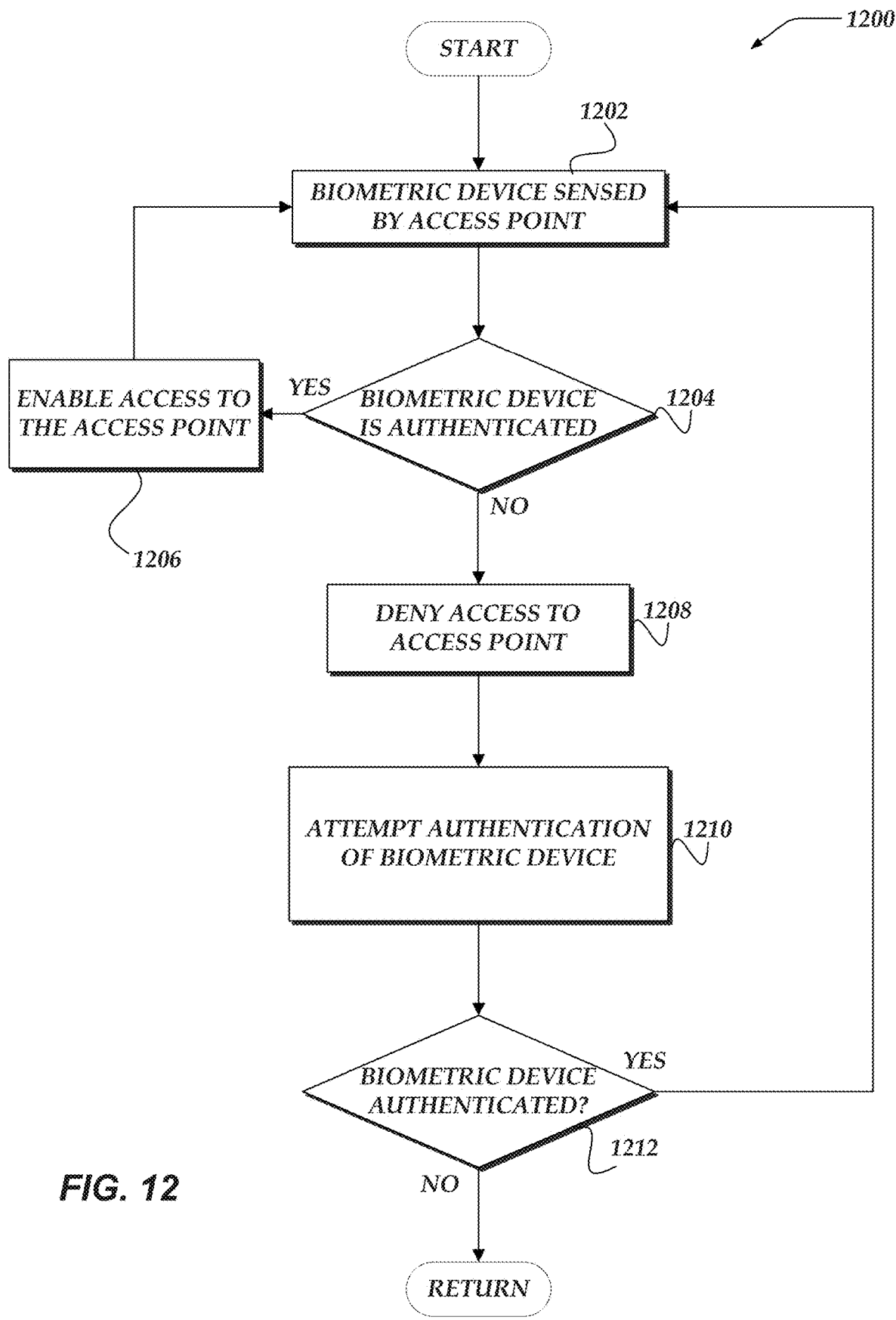
FIG. 12 is a flowchart for a process for authenticating a biometric device during encounters with access points in accordance with at least one of the various embodiments.

FIG. 12 shows an overview flowchart for process 1200 for authenticating a authentication device during encounters with access points in accordance with at least one of the various embodiments. After a start block, at block 1202, in at least one of the various embodiments, a authentication device may be sensed by an access point. Further, in at least one of the various embodiments, the authentication device may sense one or more access points that are within range of its radios. As discussed above, one or more features of radios and/or wireless facilities on the authentication devices and the access points may be employed for sensing each other's presence. For example, one or more wireless advertising protocols may be employed by the authentication devices and/or the access points. Accordingly, each time a user with an active authentication device encounters an access point control signals may be exchanged between the authentication device and the access point.

At decision block 1204, in at least one of the various embodiments, if an authentication device is authenticated, control may flow to block 1206; otherwise control may flow to block 1208. In at least one of the various embodiments, if the authentication device is preauthorized for the user, the access point may assume that the authentication device is authenticated and authorized for the user and enable access to the access point (e.g., confirming that the authentication device is in an authenticated state). Note, access to the access point may be enabled without having to capture additional biometric signals or information from the user. Thus, in at least one of the various embodiments, the user may be enabled to access multiple access points at different times as long as the authentication device remains in an authenticated state (e.g., as long as the authentication device has not been removed or separated from the authenticated user).

At block 1206, in at least one of the various embodiments, access to the encountered access point may be enabled. Next, control may loop back to block 1202. Accordingly, in at least one of the various embodiments, process 1200 may continue sensing access points and enabling access to them based on the authenticated status of the preauthorized authentication device.

At block 1208, in at least one of the various embodiments, since the authentication device is not authenticated or preauthorized, access to the encountered access point may be denied. In at least one of the various embodiments, as discussed above an authentication device may become unauthenticated if a previously authenticated user removes the preauthorized authentication device. Also, as discussed above, in at least one of the various embodiments, an authentication device may be configured to require periodic re-authentication even though the user has not removed the device.

At block 1210, in at least one of the various embodiments, the authentication device may attempt to authenticate using a registration application and one or more primary biometric signals captured from the user and one or more secondary signals captured from the user, as discussed in detail above. In at least one of the various embodiments, since the authentication device is not authenticated with the user, the user may proceed to perform the actions to put the authentication device into an authenticated state and preauthorized status, as discussed in detail above.

At decision block 1212, in at least one of the various embodiments, if the attempt to authenticate and preauthorize the authentication device succeeds, control may flow to block 1202; otherwise, process 1200 may exit, returning control to a calling process. Assuming that the authentication device is preauthorized and authenticated by the user, process 1200 may loop back to block 1202 to continue sensing access points.

Figure 13:
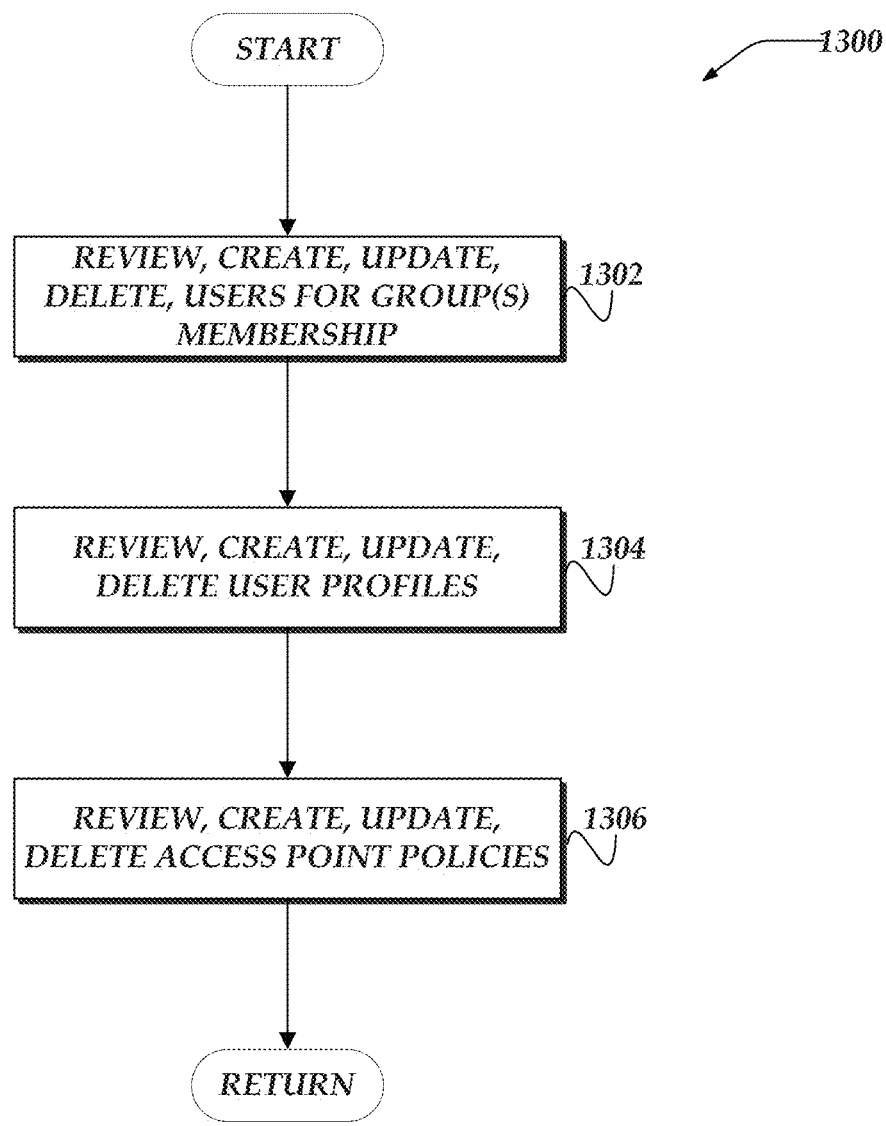
FIG. 13 is a flowchart for a process for configuring profiles for users and access points in accordance with at least one of the various embodiments.

FIG. 13 shows an overview flowchart for process 1300 for configuring profiles for users and access points in accordance with at least one of the various embodiments. After a start block, at block 1302, in at least one of the various embodiments, an administrative user may review, create, update, or delete users associated with one or more groups. At block 1304, in at least one of the various embodiments, the administrative user may review, create, update, or delete, one or more of the user profiles. At block 1306, in at least one of the various embodiments, the administrative user may review, create, update, or delete, one or more access points. Next, control may be returned to a calling process.

In at least one of the various embodiments, authentication devices may be employed to authenticate the identity of users wearing or otherwise in control of the authentication device. Further, an organization, such as, an employer, an entertainment vendor, amusement park operator, or the like, may provide or issue biometric metrics to users, such as, employees, visitors, customers, or the like. Also, in at least one of the various embodiments, a head of household for a family may issue authentication devices for each member of the family.

Accordingly, in at least one of the various embodiments, administrative users may generate user profiles that include configuration rules or other information that may be employed for determining if an authenticated and/or preauthorized user may indeed be allowed to obtain access to an access point. For example, in at least one of the various embodiments, if each member of a family has been issued authentication devices, it follows that in many cases, not each family will have the access to same access points as each. For example, underage children of the family may be disabled from accessing certain access points, such as, the family automobile or banking information. Likewise, in at least one of the various embodiments, employers that issue authentication devices to their employees may employ user profiles and/or access profiles to control access to access points for employees. Further, in at least one of the various embodiments, amusement park operators may issue authentication devices that may be employed to enable or disable customers from obtaining access to various rides, events, attractions, and so on that may be hosted at the amusement park.

In at least one of the various embodiments, profile information may be generated using one or more predefined forms and/or property sheets. Also, in at least one of the various embodiments, profile information may include customized rules that may be comprised of one or more regular expression, computer software programming languages, scripts, or the like, or combination thereof.

Figure 14:
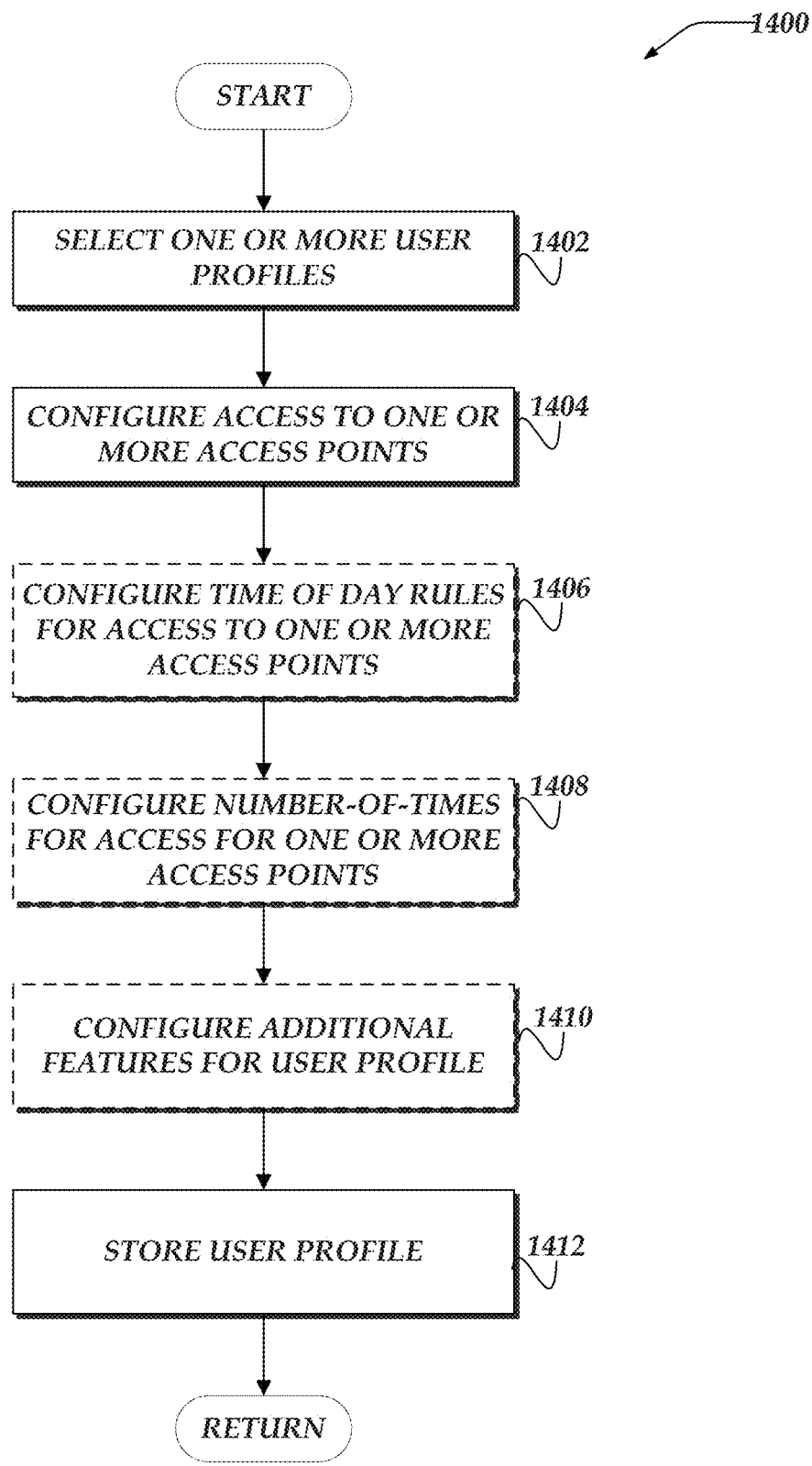
FIG. 14 is a flowchart for a process for configuring profiles for users in accordance with at least one of the various embodiments.

FIG. 14 shows an overview flowchart for process 1400 for configuring profiles for users in accordance with at least one of the various embodiments. After a start block, at block 1402, in at least one of the various embodiments, an administrative user may select one or more user profiles. In at least one of the various embodiments, user profiles may be selected individually or in groups using bulk selections, filters, or the like. Also, in at least one of the various embodiments, portions of one or more user profiles may be shared by one or more user points. For example, a global user profile may provide base configuration information each employee in a company.

At block 1404, in at least one of the various embodiments, the user profile may be configured to enable access for the user to one or more access points. In at least one of the various embodiments, individual access point and/or groups of access points may be black listed or white lists for one or more users. This information may be included in, or associated with, the user profile for each user.

At block 1406, in at least one of the various embodiments, optionally, the user profile may be configured to enable access for the user to one or more access points based on date, time of day, day-of-week, or the like, or combination thereof.

At block 1408, in at least one of the various embodiments, optionally, the user profile may be configured to define one or more count based limits for enabling the user access to one or more access points. In at least one of the various embodiments, these may be numerical limits to control the number of times an individual may access an access point. In other embodiments, the limits may be constrained to one or more time periods or time ranges. For example, a user may be restricted to accessing a particular access point one time during a defined period of time while the same user may be configured for unlimited access at other times.

At block 1410, in at least one of the various embodiments, optionally, the user profile may be configured to enable or disable one or more additional features related enabling the user access one or more access points. For example: a user may be restricted or enabled access to access points based on geolocation; a number of other users currently accessing the same or different access points exceeding a threshold; a number of other users that have accessed the same or different access points in a defined time period exceeding a threshold; or the like; or combination thereof.

At block 1412, in at least one of the various embodiments, the configured user profile may be stored. In at least one of the various embodiments, the configured user profiles may be stored in one or more computers, such as, biometric authentication service computer 116, a compute and/or storage instance (e.g., virtual machine) in cloud service and/or cloud environment, or the like. One of ordinary skill the art will appreciate that user profile configuration rules may include enabling and disabling access to access points for the user based on numerous features and/or conditions beyond those described herein. Such configuration rules are in envisaged, however, in the interest of brevity and clarity the examples are limited herein. However, the example are sufficient for enabling one of ordinary skill in the art to understand and practice the innovations included herein. Next, control may be returned to a calling process.

Figure 15:
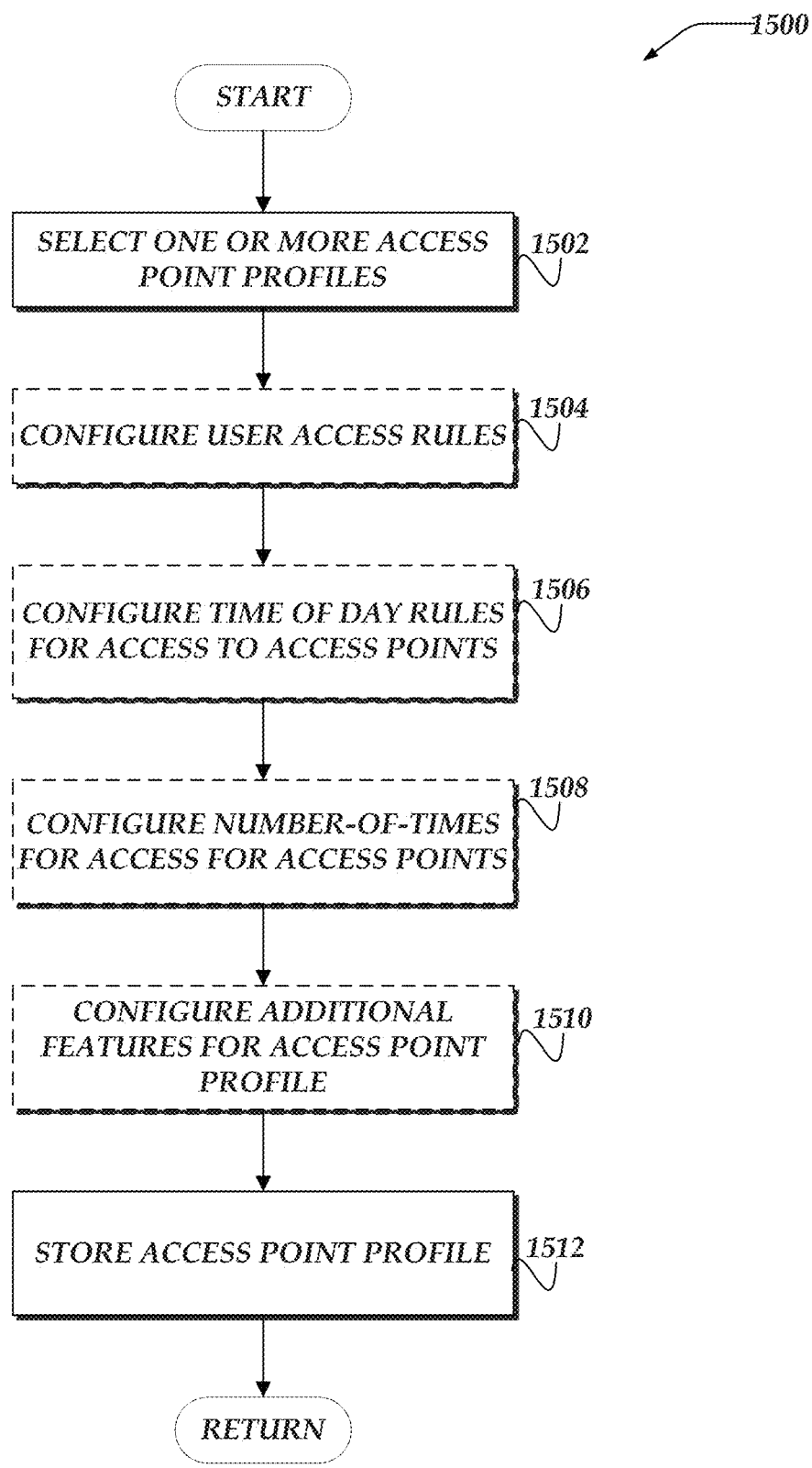
FIG. 15 is a flowchart for a process for configuring profiles for access points in accordance with at least one of the various embodiments.

FIG. 15 shows an overview flowchart for process 1500 for configuring profiles for access points in accordance with at least one of the various embodiments. After a start block, at block 1502, an administrative user may select one or more access point profiles. In at least one of the various embodiments, access point profiles may be selected individually or in groups using bulk selections, filters, or the like. Also, in at least one of the various embodiments, one or more access point profiles may be shared by one or more access points.

At block 1504, in at least one of the various embodiments, optionally, the administrative user may configure rules for determining which users may access the access points. In at least one of the various embodiments, users may be whitelisted or black listed based on individual identity, filters, group rules, or the like. In at least one of the various embodiments, filters may be inclusive or exclusive. Further, in some embodiments filters may be targeted to one or more of the various properties of users and/or user profiles, such as, name, age, access level, security clearance, frequency of access, or the like, or combination thereof.

At block 1506, in at least one of the various embodiments, optionally, the administrative user may configure time of day rules for the access points. Similar as described for block 1406 in FIG. 14. Likewise, at block 1508, in at least one of the various embodiments, optionally, the administrative user may configure policy rules for access based on number-of-times, similar as described for block 1408 in FIG. 14. At block 1510, in at least one of the various embodiments, optionally, the administrative user may configure one or more additional policy rules based on one or more other features/properties associated with the access points—similar to block 1410 in FIG. 14.

At block 1512, in at least one of the various embodiments, optionally, the administrative user may store the access point profiles. In at least one of the various embodiments, the configured access point profiles may be stored in one or more computers, such as, biometric authentication service computer 116, a compute and/or storage instance (e.g., virtual machine) in cloud service and/or cloud environment, or the like. One of ordinary skill the art will appreciate that access point profile configuration rules may include enabling and disabling access to access points for users based on numerous features and/or conditions beyond those described herein. These and other additional configuration rules are envisaged, however, in the interest of brevity and clarity the examples include herein are limited in number. However, the provided examples are sufficient for enabling one of ordinary skill in the art to understand and practice these innovations. Next, control may be returned to a calling process.

It will be understood that each block of the flowchart illustration, and combinations of blocks in the flowchart illustration, may be implemented by computer program instructions. These program instructions may be provided to a processor to produce a machine, such that the instructions, which execute on the processor, create means for implementing the actions specified in the flowchart block or blocks. The computer program instructions may be executed by a processor to cause a series of operational steps to be performed by the processor to produce a computer-implemented process such that the instructions, which execute on the processor to provide steps for implementing the actions specified in the flowchart block or blocks. The computer program instructions may also cause at least some of the operational steps shown in the blocks of the flowchart to be performed in parallel. These program instructions may be stored on some type of machine readable storage media, such as processor readable non-transitive storage media, or the like. Moreover, some of the steps may also be performed across more than one processor, such as might arise in a multi-processor computer system. In addition, one or more blocks or combinations of blocks in the flowchart illustration may also be performed concurrently with other blocks or combinations of blocks, or even in a different sequence than illustrated without departing from the general scope or spirit of the present disclosure.

Accordingly, blocks of the flowchart illustration support combinations of means for performing the specified actions, combinations of steps for performing the specified actions and program instruction means for performing the specified actions. It will also be understood that each block of the flowchart illustration, and combinations of blocks in the flowchart illustration, may be implemented by special purpose hardware-based systems, which perform the specified actions or steps, or combinations of special purpose hardware and computer instructions. The foregoing example should not be construed as limiting and/or exhaustive, but rather, an illustrative use case to show an implementation of at least one of the various embodiments of the invention.

Illustrative Use Cases

Figure 16:
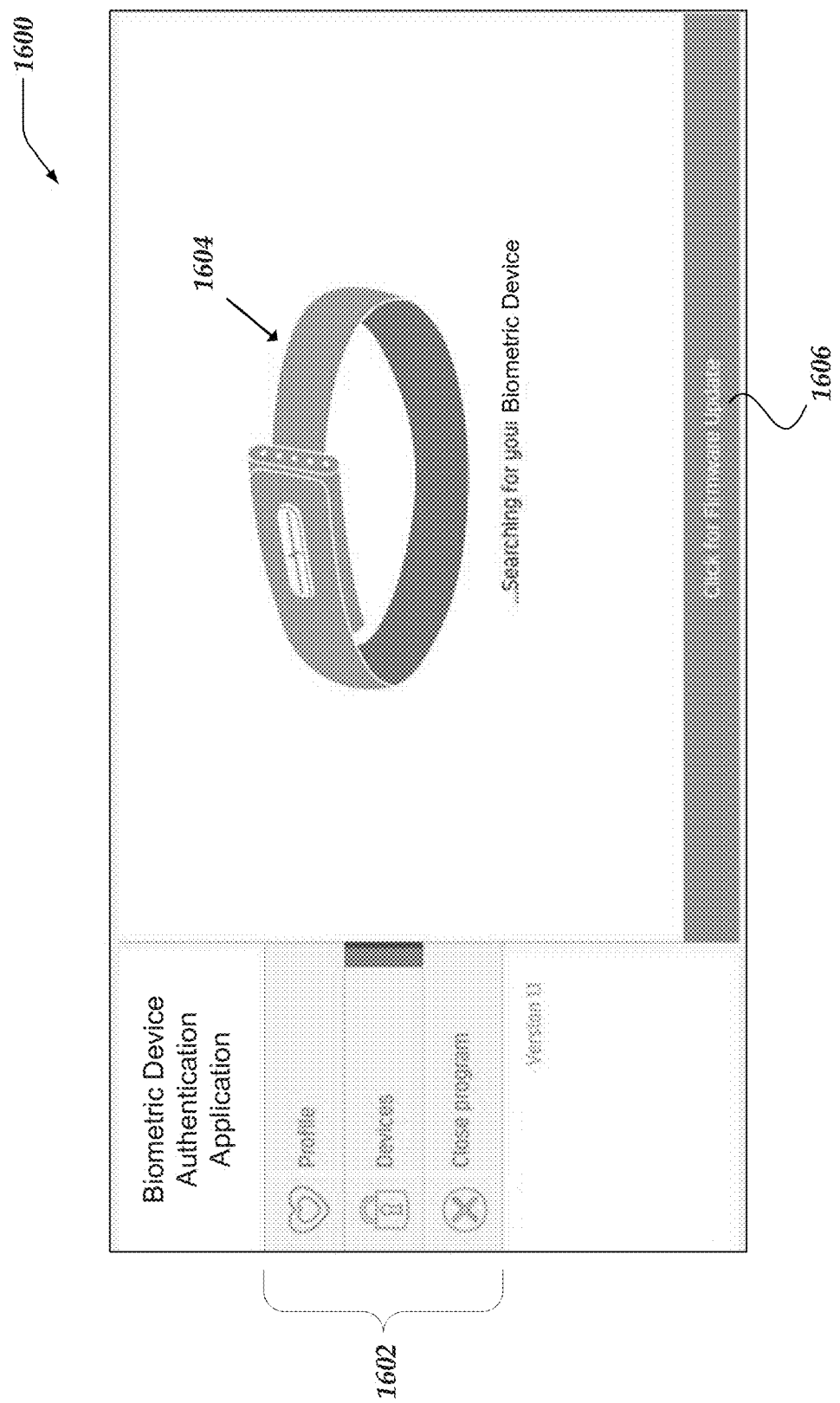
FIG. 16 is an exemplary screenshot of a graphical user interface for enrolling and/or configuring an authentication/access authorization device, such as a multimodal biometric device, in accordance with at least one of the various embodiments.

FIG. 16 illustrates a portion of user interface 1600 for enrolling and/or configuring a authentication device in accordance with at least one of the various embodiments. In at least one of the various embodiments, a registration application and/or a authentication server may be arranged to include one or more user interfaces that enable a user to enroll and/or configure their authentication devices. In at least one of the various embodiments, user interface 1600 may include a representation of the authentication device(s) such as authentication device image 1602, as well as one or more menu items for configuration such devices, such as, menu items 1604. Further, in some embodiments, a user may be enabled to update the software and/or firmware for their authentication devices by activating a user interface input, such as, button 1606.

In at least one of the various embodiments, the user interface layout and features may be arranged to accommodate different platforms, such as, client computers, network computers, mobile computers, tablet computers, smart phones, or the like. Further, in at least one of the various embodiments, user interfaces may include more or less elements as shown herein and remain within the scope of the envisaged innovations.

Figure 17:
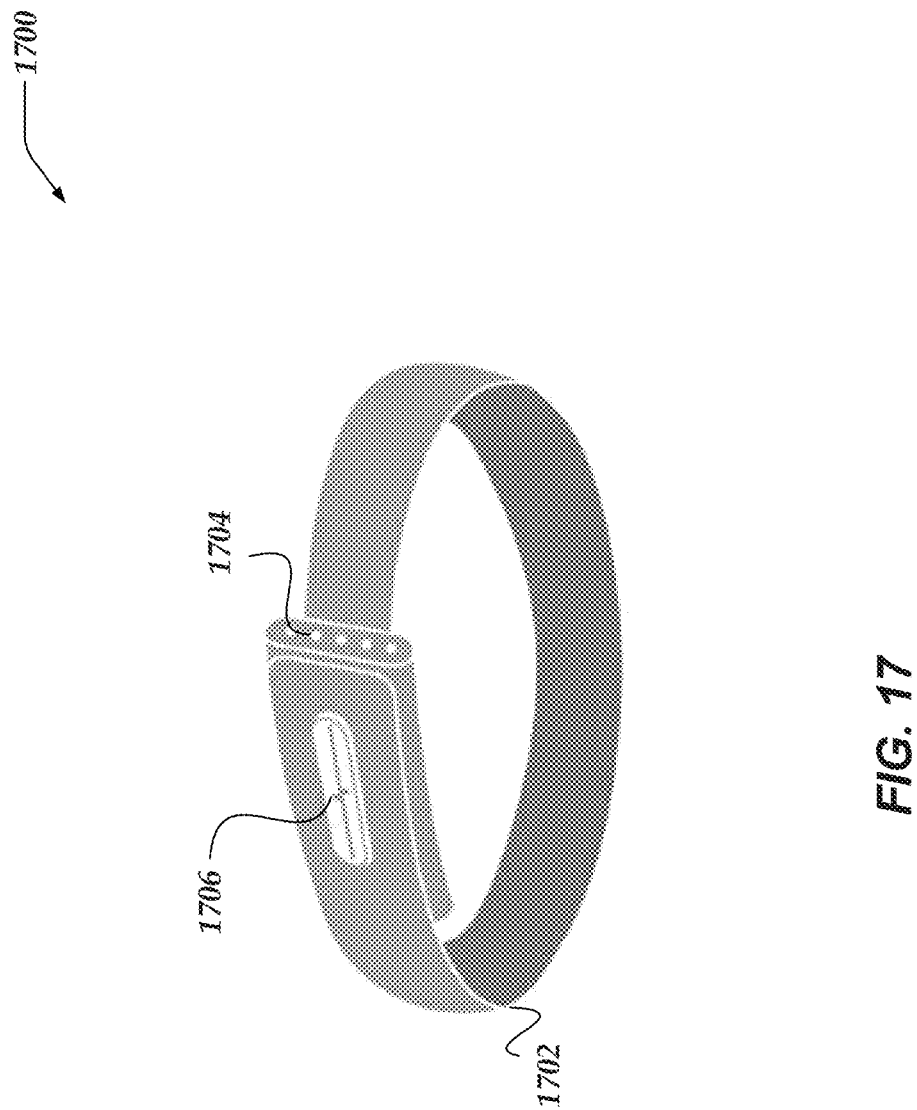
FIG. 17 is a perspective view of a wearable authentication/access authorization device, such as a multimodal biometric device, in accordance with at least one of the various embodiments.

FIG. 17 illustrates wearable authentication device 1700 in accordance with at least one of the various embodiments. In at least one of the various embodiments, authentication device 1700 may be arranged in the form a wristband, such as, wristband 1702. Also, in at least one of the various embodiments, authentication device 1700 may include LED's 1704 arranged such that they are visible to a wearer.

In at least one of the various embodiments, LEDs 1704 may be arranged to flash in different patterns and/or colors. In some embodiments, the different patterns of flashing and/or colors may correspond to particular operations, states, actions, or the like. For example, unique flashing or light patterns may be established to represent if the authentication device is capturing and/or transmitting biometric signals/data. Also, for example, a particular LED pattern may indicate if the authentication device is authenticated, preauthorized, in the range of one or more access points, or the like.

In at least one of the various embodiments, contact 1706 may be a button, sensor, electrode, or the like, or combination thereof. In some embodiments, contact 1706 may be a sensor similar to sensor 504 and/or sensor 506 of FIG. 5. In at least one of the various embodiments, contact 1706 may be arranged to be sensitive to receiving user inputs such as finger tapping, finger swiping, touching, or the like, or combination thereof.

While the present disclosure describes various embodiments for illustrative purposes, such description is not intended to be limited to such embodiments. On the contrary, the applicant's teachings described and illustrated herein encompass various alternatives, modifications, and equivalents, without departing from the embodiments, the general scope of which is defined in the appended claims. Except to the extent necessary or inherent in the processes themselves, no particular order to steps or stages of methods or processes described in this disclosure is intended or implied. In many cases the order of process steps may be varied without changing the purpose, effect, or import of the methods described.

Information as herein shown and described in detail is fully capable of attaining the above-described object of the present disclosure, the presently preferred embodiment of the present disclosure, and is, thus, representative of the subject matter which is broadly contemplated by the present disclosure. The scope of the present disclosure fully encompasses other embodiments which may become apparent to those skilled in the art, and is to be limited, accordingly, by nothing other than the appended claims, wherein any reference to an element being made in the singular is not intended to mean "one and only one" unless explicitly so stated, but rather "one or more." All structural and functional equivalents to the elements of the above-described preferred embodiment and additional embodiments as regarded by those of ordinary skill in the art are intended to be encompassed by the present claims. Moreover, no requirement exists for a system or method to address each and every problem sought to be resolved by the present disclosure, for such to be encompassed by the present claims. Furthermore, no element, component, or method step in the present disclosure is intended to be dedicated to the public regardless of whether the element, component, or method step is explicitly recited in the claims. However, that various changes and modifications in form, material, work-piece, and fabrication material detail may be made, without departing from the spirit and scope of the present disclosure, as set forth in the appended claims, as may be apparent to those of ordinary skill in the art, are also encompassed by the disclosure.

What is claimed is:

1. A digital user authentication device to authenticate an authorized user, the device comprising:
a wearable user authentication interface to be worn by the authorized user and operable to receive as input, via an authorized user finger contact, unique user identification data required to execute a digital user authentication process, wherein said wearable user authentication interface is operable to capture a user finger image via said authorized user finger contact as input for said unique user identification data;
a distinct physiological sensor operable to interface with the authorized user via a same user finger contact and a distinct physiological interface formed at a distinct wearable user contact location, to simultaneously acquire, via said same user finger contact and said distinct physiological interface upon the device being worn by said authorized user, a physiological signal comprising a time-variable waveform from the authorized user to automatically confirm a live user presence during said user authentication process; and
a digital data processor and computer-readable memory operable to execute computer-readable instructions to invoke said user authentication process based on said unique user identification data while confirming said live user presence based on said physiological signal such that a successful user authentication is only concluded upon confirmation of said live user presence during said authentication process, wherein said digital data processor and computer-readable memory are further operable to invoke comparison of said time-variable waveform with a generic non-user-specific physiological signal profile to confirm said live user presence irrespective of user identity upon said time-variable waveform matching said generic non-user-specific physiological signal profile and denying said live user presence upon said comparison automatically determining that said time-variable waveform is attenuated or corrupted relative to said generic non-user-specific physiological signal profile.

2. The digital user authentication device of claim 1, wherein said distinct wearable user contact location comprises a user wrist contact location.

3. The digital user authentication device of claim 1, wherein said physiological sensor is a heart-related sensor operable to acquire a heart-related signal between said user finger contact and said distinct wearable user contact location only upon said user finger contact and said distinct wearable user contact location corresponding to a same user, wherein said distinct physiological sensor comprises an ECG sensor.

4. The digital user authentication device of claim 1, wherein said wearable user authentication interface comprises a fingerprint sensor or a finger-vein sensor.

5. The digital user authentication device of claim 1, wherein said distinct physiological sensor comprises a physiological sensor probe disposed on, forming part or consisting of a bezel or ring at least partially surrounding said wearable user authentication interface.

6. The digital user authentication device of claim 1, further comprising a wireless communication interface operable to communicate with a wireless access point to wirelessly authorize the user authenticated access to a resource operatively associated with said wireless access point once successfully authenticated, wherein said user authentication process consists of an onboard authentication process to pre-authorize the user authenticated access, and wherein said authenticated access is authorized upon the device wirelessly communicating an authenticated user signal to said access point.

7. The digital user authentication device of claim 1, wherein said distinct physiological sensor or a further physiological sensor is operable post-authentication to automatically interface with the user to acquire a post-authentication physiological signal at or near said distinct wearable user contact location, and wherein said instructions are further executable to revoke said successful user authentication upon identifying a designated lapse in said post-authentication physiological signal post-authentication, wherein said distinct physiological signal comprises an ECG signal, wherein said post-authentication signal comprises a bioimpedance signal, and wherein said wearable user authentication interface comprises a fingerprint sensor.

8. The digital user authentication device of claim 1, further comprising a device removal sensor operable to cause revocation of said successful user authentication upon identifying removal of said wearable user authentication interface from the user.

9. The digital user authentication device of claim 1, wherein said distinct physiological sensor comprises multiple physiological sensors, and wherein said distinct physiological interface comprises distinct wearable user contact locations such that distinct physiological signals are acquired via said same user finger contact of the authorized user providing said authorized user finger contact.

10. The digital user authentication device of claim 1, wherein said generic non-user-specific physiological signal profile comprises a synthetic or representative profile, and wherein said matching comprises matching said generic non-user-specific physiological signal profile within a designated level of confidence.

11. A digital user authentication system for authenticating an authorized user, the system comprising:
a wearable wireless digital user authentication device comprising:
a wearable user authentication interface to be worn by the authorized user and operable to receive as input, via an authorized user finger contact, unique user identification data required to execute a digital user authentication process, wherein said wearable user authentication interface is operable to capture a user finger image via said authorized user finger contact as input for said unique user identification data;
a distinct physiological sensor operable to interface with the authorized user via a same user finger contact and a distinct physiological interface formed at a distinct wearable user contact location, to simultaneously acquire, via said same user finger contact and said distinct physiological interface upon the device being worn by said authorized user, a physiological signal comprising a time-variable waveform from the authorized user to automatically confirm a live user presence during said user authentication process;

a digital data processor and computer-readable memory operable to execute computer-readable instructions to invoke said user authentication process based on said unique user identification data while confirming said live user presence based on said physiological signal such that a successful user authentication is only concluded upon confirmation of said live user presence during said user authentication process, wherein said digital data processor and computer-readable memory are further operable to invoke comparison of said time-variable waveform with a generic non-user-specific physiological signal profile to confirm said live user presence irrespective of identity upon said time-variable waveform matching said generic non-user-specific physiological signal profile and denying said live user presence upon said comparison automatically determining that said time-variable waveform is attenuated or corrupted; and a wireless communication interface operable to communicate an authenticated user signal to a wireless access point once successfully authenticated; and a wireless access point operable to wirelessly receive said authenticated user signal from said wireless digital user authentication device to authenticate the authorized user based on said successful authentication.

12. The system of claim 11, wherein said wireless access point is operatively associated with the designated resource, and wherein access to the designated resource is authorized via said access point upon receipt thereof of said authenticated user signal, wherein said user authentication process consists of an onboard authentication process to pre-authorize the user authenticated access to the resource, and wherein said authenticated access is authorized upon the device wirelessly communicating an authenticated user signal to said access point.

13. The system of claim 11, wherein said physiological sensor is a heart-related sensor operable to acquire a heart-related signal between said user finger contact and said distinct wearable user contact location only upon said user finger contact and said distinct wearable user contact location correspond to a same user, wherein said distinct physiological sensor comprises an ECG sensor.

14. The system of claim 11, wherein said wearable user authentication interface comprises a fingerprint sensor or a finger-vein sensor.

15. The system of claim 11, wherein said generic non-user-specific physiological signal profile comprises a synthetic or representative profile, and wherein said matching comprises matching said generic non-user-specific physiological signal profile within a designated level of confidence.

16. A computer-implemented digital user authentication process, comprising:
receiving via an authorized user finger contact as input at a wearable user authentication interface, said interface to be worn by an authorized user, unique user identification data to invoke a digital user authentication process, wherein said wearable user authentication interface is operable to capture a user finger image via said authorized user finger contact as input for said unique user identification data;

receiving simultaneously as further input via a same user finger contact and a distinct physiological interface formed at a distinct wearable user contact location of said wearable user authentication interface a physiological signal comprising a time-variable waveform to automatically confirm a live user presence of said authorized user during said user authentication process; and using one or more digital data processors, invoking said user authentication process based on said unique user identification data while confirming said live user presence based on said physiological signal such that a successful user authentication is only concluded upon confirmation of said live user presence during said user authentication process, wherein said live user presence is confirmed upon successfully matching said time-variable waveform with a generic non-user-specific physiological signal profile within a designated level of confidence, and denied upon said matching automatically determining that said time-variable waveform is attenuated or corrupted.

17. The process of claim 16, further comprising wirelessly communicating authentication data from said wearable user authentication interface with a wireless access point or a remote authentication server associated therewith to wirelessly authorize the user authenticated access to a resource operatively associated with said wireless access point once successfully authenticated, wherein said user authentication process is implemented by said wearable user authentication interface to pre-authorize the user authenticated access, and wherein said authenticated access is authorized upon wirelessly communicating an authenticated user signal to said access point.

18. The process of claim 16, wherein a post-authentication physiological signal is received as input post-authentication, the process further comprising revoking said successful user authentication upon identifying a designated lapse in said post-authentication physiological signal post-authentication.

19. The process of claim 16, further comprising detecting a proximity of said wearable user authentication interface to a designated access point, and revoking said authorized user authenticated access upon said proximity exceeding a designated proximity threshold.

20. The process of claim 16, further comprising detecting removal of said wearable user authentication interface, and automatically revoking said authorized user authenticated access.

21. The process of claim 16, wherein said generic non-user-specific physiological signal profile comprises a synthetic or representative profile, and wherein said matching comprises matching said generic non-user-specific physiological signal profile within a designated level of confidence.

* * * * *